United States Patent
Edwards et al.

(10) Patent No.: US 7,923,451 B2
(45) Date of Patent: Apr. 12, 2011

(54) 2-AMINOPYRIMIDINE MODULATORS OF THE HISTAMINE $H_4$ RECEPTOR

(75) Inventors: James P. Edwards, San Diego, CA (US); Brad M. Savall, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 41 days.

(21) Appl. No.: 12/070,051

(22) Filed: Feb. 14, 2008

(65) Prior Publication Data
US 2008/0194577 A1   Aug. 14, 2008

Related U.S. Application Data

(60) Provisional application No. 60/889,798, filed on Feb. 14, 2007.

(51) Int. Cl.
*A61K 31/505* (2006.01)
(52) U.S. Cl. ........................ 514/275; 548/557
(58) Field of Classification Search ................. 514/275; 548/557
See application file for complete search history.

(56) References Cited

U.S. PATENT DOCUMENTS

| | | |
|---|---|---|
| 3,907,801 A | 9/1975 | Wu et al. |
| 4,980,350 A | 12/1990 | MacCoss et al. |
| 5,077,290 A | 12/1991 | Fisher et al. |
| 5,124,328 A | 6/1992 | Fisher et al. |
| 5,223,505 A | 6/1993 | Hargreaves et al. |
| 5,470,976 A | 11/1995 | Humphrey et al. |
| 5,614,524 A | 3/1997 | Matassa et al. |
| 5,681,957 A | 10/1997 | Wolters et al. |
| 5,696,266 A | 12/1997 | Humphrey et al. |
| 5,760,623 A | 6/1998 | Hastings |
| 5,777,134 A | 7/1998 | Bakshi et al. |
| 5,817,802 A | 10/1998 | Humphrey et al. |
| 5,859,041 A | 1/1999 | Liverton et al. |
| 5,880,139 A | 3/1999 | Chang |
| 5,955,480 A | 9/1999 | Chang |
| 5,998,464 A | 12/1999 | Bakshi et al. |
| 6,369,084 B1 | 4/2002 | Lacombe et al. |
| 6,410,526 B1 | 6/2002 | Duggan et al. |
| 6,465,462 B1 | 10/2002 | Carling et al. |
| 7,253,200 B2 | 8/2007 | Buzard et al. |
| 7,405,221 B2 | 7/2008 | Kopka et al. |
| 2001/0027196 A1 | 10/2001 | Borroni et al. |
| 2002/0107245 A1 | 8/2002 | Wagle et al. |
| 2002/0137746 A1 | 9/2002 | Carl et al. |
| 2006/0051616 A1 | 3/2006 | Suzuki et al. |
| 2006/0281749 A1 | 12/2006 | Wagle et al. |
| 2006/0293339 A1 | 12/2006 | Chakravarty et al. |
| 2007/0065443 A1 | 3/2007 | Tobia et al. |
| 2007/0185075 A1 | 8/2007 | Bell et al. |
| 2009/0209571 A1 | 8/2009 | Cote et al. |
| 2009/0233896 A1 | 9/2009 | Arrington et al. |
| 2009/0286772 A1 | 11/2009 | Chau et al. |

FOREIGN PATENT DOCUMENTS

| | | |
|---|---|---|
| EP | 200968 A1 | 11/1986 |
| EP | 200968 B1 | 8/1990 |
| EP | 1437348 | 7/2004 |
| EP | 1505064 | 2/2005 |
| EP | 1767537 | 3/2007 |
| WO | WO 01/47897 | 7/2001 |
| WO | WO 01/47921 | 7/2001 |
| WO | WO 01/62233 | 8/2001 |
| WO | 0222584 | 3/2002 |
| WO | WO 03/089601 | 10/2003 |
| WO | WO 2004/052862 | 6/2004 |
| WO | WO 2005/054239 | 6/2005 |
| WO | WO 2006/034446 | 3/2006 |
| WO | WO 2006/053109 | 5/2006 |
| WO | WO 2006/065590 | 6/2006 |
| WO | WO 2006/123165 | 11/2006 |
| WO | WO 2007/031529 | 3/2007 |
| WO | WO 2007/090852 | 8/2007 |
| WO | WO 2007/090853 | 8/2007 |
| WO | WO 2007/090854 | 8/2007 |
| WO | WO 2008/008359 | 1/2008 |
| WO | WO 2008/031556 | 3/2008 |
| WO | WO 2008/060766 | 5/2008 |
| WO | WO 2009/068512 | 6/2009 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Lespagnol, A. et al. Chim. Therap. 1965, 1, 26-31.
Lespagnol, A. et al. Chim. Therap. 1971, 6(2), 105-108.
Libby, P. Inflammation in atherosclerosis. Nature 2002, 420, 868-874.
Ling, P. et al. Histamine $H_4$ receptor mediates eosinophil chemotaxis with cell shape change and adhesion molecule upregulation. Br. J. Pharmacol. 2004, 142(1), 161-171.
Lippert, U. et al. Human Skin Mast Cells Express H2 and H4, but not H3 Receptors. J. Invest. Dermatol. 2004, 123(1), 116-123.
Liu, C. et al. Cloning and Pharmacological Characterization of a Fourth Histamine Receptor ($H_4$) Expressed in Bone Marrow. Mol. Pharmacol. 2001, 59(3), 420-426.
Mashikian, V.M. et al. Identification of IL-16 as the lymphocyte chemotactic activity in the bronchoalveolar lavage fluid of histamine-challenged asthmatic patients. J. Allergy Clin. Immunol. 1998, 101 (6, Part 1), 786-792.
Morse, K.L. et al. Cloning and Characterization of a Novel Human Histamine Receptor. J. Pharmacol. Exp. Ther. 2001, 296(3), 1058-1066.
Nathan, C. Points of control in inflammation. Nature 2002, 420(6917), 846-852.
Ohki, E. et al. Expression of Histamine H4 Receptor in Synovial Cells from Rheumatoid Arthritic Patients. Biol. Pharm. Bull. 2007, 30(11), 2217-2220.
O'Reilly, M. et al. Identification of a $H_4$ Receptor on Human Eosinophils—Role in Eosinophil Chemotaxis. J. Recept. Signal Transduction 2002, 22(1-4), 431-448.

(Continued)

*Primary Examiner* — James O Wilson
*Assistant Examiner* — Douglas M Willis

(57) ABSTRACT

2-Aminopyrimidine compounds are described, which are useful as $H_4$ receptor modulators. Such compounds may be used in pharmaceutical compositions and methods for the treatment of disease states, disorders, and conditions mediated by $H_4$ receptor activity, such as allergy, asthma, autoimmune diseases, and pruritis.

5 Claims, No Drawings

OTHER PUBLICATIONS

Ostercamp, D.L. et al. Rigid Core Vinamidinium Salts and Their N,N'-Rotamers. J. Org. Chem. 2003, 68, 3099-3105.

Pietrzycki, W. et al. Tautomerism and Rotamerism in 2-Methylamino-, 2-Anilino-, 2-Acetamido-, and 2-Benzamidopyridines. Bull. Soc. Chim. Belg. 1993, 102(11-12), 709-717.

Slater, A. et al. Increase in epithelial mast cell numbers in the nasal mucosa of patients with perennial allergic rhinitis. J. Laryngol. Otol. 1996, 110, 929-933.

Steinberg, D. Atherogenesis in perspective: Hypercholesterolemia and inflammation as partners in crime. Nature Med. 2002, 8(11), 1211-1217.

Takeshita, K. et al. Critical Role of Histamine $H_4$ Receptor in Leukotriene $B_4$ Production and Mast Cell-Dependent Neutrophil Recruitment Induced by Zymosan in Vivo. J. Pharmacol. Exp. Ther. 2003, 307(3), 1072-1078.

Thurmond, R.L. et al. A Potent and Selective Histamine H4 Receptor Antagonist with Anti-Inflammatory Properties. J. Pharmacol. Exp. Ther. 2004, 309(1), 404-413.

Thurmond, R.L. et al. The role of histamine H1 and H4 receptors in allergic inflammation: the search for new antihistamines. Nat. Rev. Drug Disc. 2008, 7, 41-53.

Tracey, K.J. The inflammatory reflex. Nature 2002, 420(6917), 853-859.

Varga, C. et al. Inhibitory effects of histamine $H_4$ receptor antagonists on experimental colitis in the rat. Eur. J. Pharmacol. 2005, 522(1-3), 130-138.

Voehringer, D. et al. Type 2 Immunity Reflects Orchestrated Recruitment of Cells Committed to IL-4 Production. Immunity 2004, 20(3), 267-277.

Weiner, H.L. et al. Inflammation and therapeutic vaccination in CNS diseases. Nature 2002, 420(6917), 879-884.

Willecomme, B. Annales de Chimie 1969, 4(6), 405-428.

Zhang, M. et al. The Histamine H4 Receptor: A Novel Mediator of Inflammatory and Immune Disorders. Pharmacol. Ther. 2007, 113, 594-606.

Zhang, M. et al. The Histamine H4 Receptor in Autoimmune Disease. Expert Opin. Investig. Drugs 2006, 15(11), 1443-1452.

Amin, K. et al. Inflammation and Structural Changes in the Airways of Patients with Atopic and Nonatopic Asthma. Am. J. Resp. Crit. Care Med. 2000, 162(6), 2295-2301.

Becker, I. J. Het. Chem. 2005, 42(7), 1289-1295.

Bell, J.K. et al. Involvement of histamine $H_4$ and $H_1$ receptors in scratching induced by histamine receptor agonists in BalbC mice. Br. J. Pharmacol. 2004, 142(2), 374-380.

Benoist, C. et al. Mast cells in autoimmune disease. Nature 2002, 420(6917), 875-878.

Buckland, K.F. et al. Histamine induces cytoskeletal changes in human eosinophils via the $H_4$ receptor Br. J. Pharmacol. 2003, 140(6), 1117-1127.

Cholli, A.L. et al. Necessary Conditions for the Welectron Delocalization in Enamino-Type Muscle Relaxants. J. Pharm. Sci. 1993, 82(12), 1275-1280.

Coge, F. et al. Structure and Expression of the Human Histamine $H_4$-Receptor Gene. Biochem. Biophys. Res. Commun. 2001, 284(2), 301-309.

Cohen, J. The immunopathogenesis of sepsis. Nature 2002, 420(6917), 885-891.

Coussens, L.M. et al. Inflammation and cancer. Nature 2002, 420(6917), 860-867.

Crimi, E. et al. Increased numbers of mast cells in bronchial mucosa after the late-phase asthmatic response to allergen. Am. Rev. Respir. Dis. 1991, 144(6), 1282-1286.

de Esch, I.J.P. et al. The histamine $H_4$ receptor as a new therapeutic target for inflammation. Trends Pharmacol. Sci. 2005, 26(9), 462-469.

Dunford, P.J. et al. Histamine H4 receptor antagonists are superior to traditional antihistamines in the attenuation of experimental pruritus. J. Allergy Clin. Immunol. 2007, 119(1), 176-183.

Fokkens, W.J. et al. Dynamics of mast cells in the nasal mucosa of patients with allergic rhinitis and non-allergic controls: a biopsy study. Clin. Exp. Allergy 1992, 22(7), 701-710.

Fung-Leung, W.-P. et al. Histamine H4 receptor antagonists: The new antihistamines? Curr. Opin. Invest. Drugs 2004, 5(11), 1174-1183.

Gantner, F. et al. Histamine $H_4$ and $H_2$ Receptors Control Histamine-Induced Interleukin-16 Release from Human $CD8^+$ T Cells. J. Pharmacol. Exp. Ther. 2002, 303(1), 300-307.

Garner, J. et al. Identification of Aminopyrimidine Regioisomers via Line Broadening Effects in 1H and 13C NMR Spectroscopy. Aust. J. Chem. 2004, 57, 1079-1083.

Gauvreau, G.M. et al. Increased Numbers of Both Airway Basophils and Mast Cells in Sputum after Allergen Inhalation Challenge of Atopic Asthmatics. Am. J. Resp. Crit. Care Med. 2000, 161(5), 1473-1478.

Graton, J. et al. Hydrogen-bond basicity $pK_{HB}$ scale of secondary amines. J. Chem. Soc., Perkin Trans. 2, 2001, 2130-2135.

Gutzmer, R. et al. Histamine $H_4$ Receptor Stimulation Suppresses IL-12p70 Production and Mediates Chemotaxis in Human Monocyte-Derived Dendritic Cells. J. Immunol. 2005, 174(9), 5224-5232.

Hofstra, C.L. et al. Histamine $H_4$ Receptor Mediates Chemotaxis and Calcium Mobilization of Mast Cells. J. Pharmacol. Exp. Ther. 2003, 305(3), 1212-1221.

Ikawa, Y. et al. Histamine $H_4$ Receptor Expression in Human Synovial Cells Obtained from Patients Suffering from Rheumatoid Arthritis. Biol. Pharm. Bull. 2005, 28(10), 2016-2018.

Kassel, O. et al. Local increase in the number of mast cells and expression of nerve growth factor in the bronchus of asthmatic patients after repeated inhalation of allergen at low-dose. Clin. Exp. Allergy 2001, 31(9), 1432-1440.

Kemnitz, C.R. et al. "Amide Resonance" Correlates with a Breadth of C-N Rotation Barriers. J. Am. Chem. Soc. 2007, 129, 2521-2528.

Kirby, J.G. et al. Bronchoalveolar cell profiles of asthmatic and nonasthmatic subjects. Am. Rev. Respir. Dis. 1987, 136(2), 379-383.

Krug, N. et al. Interleukin 16 and T-cell Chemoattractant Activity in Bronchoalveolar Lavage 24 Hours after Allergen Challenge in Asthma. Am. J. Resp. Crit. Care Med. 2000, 162(1), 105-111.

Altenbach, Robert et al., Structure-Activity Studies on a Series of a 2-Aminopyrimidine-Containing Histamine H4 Receptor Ligands, Jour. Med. Chem. (2008), 51(20), pp. 6571-6580.

Ge, Hai-Xia et al., Synthesis and bioactivity of aripiprazole derivatives. Arzneimittel Forschung, (2006), 56(10, pp. 673-677.

Dunford, P.J. et al. The histamine H4 receptor mediates allergic airway inflammation by regulating the activation of CD4+ T cells. Journal of Immunology, 2006. vol. 176(11) , 7062-7070.

Horr et al. STAT1 phosphorylation and cleavage is regulated by the histamine (H4) receptor in human atopic and non-atopic lymphocytes. International Immunopharmacology 2006, vol. 6 (10), 1577-1585.

Jablonowski, J. et al., The first potent and selective non-imidazole human histamine H4 receptor antagonists. Journal of Medicinal Chemistry, 2003. vol. 46(19), 3957-3960.

Jiang et al. Cloning and pharmacological characterization of the dog histamine H-4 receptor. European Journal of Pharmacology, 2008. vol. 592(1-3), 26-32.

Jokuti et al. Histamine H4 receptor expression is elevated in human nasal polyp tissue, Cell Biology International. 2007. vol. 31(11) 1367-1370.

Kiss, R. et al. Histamine H4 receptor ligands and their potential therapeutic applications. Expert Opin. Ther. Patents, 2009, vol. 19(2), 119-135.

Lee-Dutra, A. et al., Identification of 2-arylbenzimidazoles as potent human histamine H-4 receptor ligands, Bioorganic & Medicinal Chemistry Letters 2006. vol. 16(23), 6043-6048.

Leite-de-Moraes, Cutting edge: histamine receptor H4 activation positively regulates in vivo IL-4 and IFN-gamma production by invariant NKT cells. Journal of Immunology, 2009. 182(3):1233-1236.

Lim, H. et al., Evaluation of histamine H-1-, H-2-, and H-3-receptor ligands at the human histamine H-4 receptor: Identification of 4-methylhistamine as the first potent and selective H-4 receptor agonist. Journal of Pharmacology & Experimental Therapeutics, 2005, vol. 314(3), 1310-1321.

Smits, R.A. et al. Major advances in the development of histamine H4 receptor ligands. Drug Discovery Today, 2009, vol.14(15-16):745-753.

Venable, J.D. et al. Preparation and biological evaluation of indole, benzimidazole, and thienopyrrole piperazine carboxamides: Potent human histamine $H_4$ antagonists. Journal of Medicinal Chemistry, 2005. vol. 48(26), 8289-8298.

International Search Report dated Jul. 10, 2008 for International Appln. No. PCT/US08/01950.

Andrei et al. "New Pyrimidines 2-amino-6-methyl-4-amino-substitutes, supposed to be biologically actives." Annals of West University of Timisoara, vol. 14 (2), 2005, pp. 125-130.

European Extended Search Report dated Mar. 3, 2010 for European Appln. No. 08725564.2.

* cited by examiner

2-AMINOPYRIMIDINE MODULATORS OF THE HISTAMINE $H_4$ RECEPTOR

This application claims the benefit of U.S. provisional patent application Ser. No. 60/889,798, filed on Feb. 14, 2007, which is incorporated herein by reference.

FIELD OF THE INVENTION

The present invention relates to certain 2-aminopyrimidine compounds, pharmaceutical compositions containing them, methods of making them, and methods of using them for the modulation of the histamine $H_4$ receptor and for the treatment of disease states, disorders, and conditions mediated by histamine $H_4$ receptor activity.

BACKGROUND OF THE INVENTION

The histamine $H_4$ receptor ($H_4R$) is the most recently identified receptor for histamine (for reviews, see: Fung-Leung, W.-P., et al., Curr. Opin. Invest. Drugs 2004, 5(11), 1174-1183; de Esch, I. J. P., et al., Trends Pharmacol. Sci. 2005, 26(9), 462-469; Zhang, M. et al. Pharmacol. Ther. 2007, 113, 594-606; Thurmond, R. L. et al. Nat. Rev. Drug Disc. 2008, 7, 41-53; Zhang, M. et al. Expert Opin. Investig. Drugs 2006, 15(11), 1443-1452). The receptor is found in the bone marrow and spleen and is expressed on eosinophils, basophils, mast cells (Liu, C., et al., Mol. Pharmacol. 2001, 59(3), 420-426; Morse, K. L., et al., J. Pharmacol. Exp. Ther. 2001, 296(3), 1058-1066; Hofstra, C. L., et al., J. Pharmacol. Exp. Ther. 2003, 305(3), 1212-1221; Lippert, U., et al., J. Invest. Dermatol. 2004, 123(1), 116-123; Voehringer, D., et al., Immunity 2004, 20(3), 267-277), $CD8^+$ T cells (Gantner, F., et al., J. Pharmacol. Exp. Ther. 2002, 303(1), 300-307), dendritic cells, and human synovial cells from rheumatoid arthritis patients (Ikawa, Y., et al., Biol. Pharm. Bull. 2005, 28(10), 2016-2018). However, expression in neutrophils and monocytes is less well defined (Ling, P., et al., Br. J. Pharmacol. 2004, 142(1), 161-171). Receptor expression is at least in part controlled by various inflammatory stimuli (Coge, F., et al., Biochem. Biophys. Res. Commun. 2001, 284(2), 301-309; Morse, et al., 2001), thus supporting that $H_4$ receptor activation influences inflammatory responses. Because of its preferential expression on immunocompetent cells, the $H_4$ receptor is closely related with the regulatory functions of histamine during the immune response.

A biological activity of histamine in the context of immunology and autoimmune diseases is closely related with the allergic response and its deleterious effects, such as inflammation. Events that elicit the inflammatory response include physical stimulation (including trauma), chemical stimulation, infection, and invasion by a foreign body. The inflammatory response is characterized by pain, increased temperature, redness, swelling, reduced function, or a combination of these.

Mast cell degranulation (exocytosis) releases histamine and leads to an inflammatory response that may be initially characterized by a histamine-modulated wheal and flare reaction. A wide variety of immunological stimuli (e.g., allergens or antibodies) and non-immunological (e.g., chemical) stimuli may cause the activation, recruitment, and de-granulation of mast cells. Mast cell activation initiates allergic inflammatory responses, which in turn cause the recruitment of other effector cells that further contribute to the inflammatory response. It has been shown that histamine induces chemotaxis of mouse mast cells (Hofstra, et al., 2003). Chemotaxis does not occur using mast cells derived from $H_4$ receptor knockout mice. Furthermore, the response is blocked by an $H_4$-specific antagonist, but not by $H_1$, $H_2$ or $H_3$ receptor antagonists (Hofstra, et al., 2003; Thurmond, R. L., et al., J. Pharmacol. Exp. Ther. 2004, 309(1), 404-413). The in vivo migration of mast cells to histamine has also been investigated and shown to be $H_4$ receptor dependent (Thurmond, et al., 2004). The migration of mast cells may play a role in allergic rhinitis and allergy where increases in mast cell number are found (Kirby, J. G., et al., Am. Rev. Respir. Dis. 1987, 136(2), 379-383; Crimi, E., et al., Am. Rev. Respir. Dis. 1991, 144(6), 1282-1286; Amin, K., et al., Am. J. Resp. Crit. Care Med. 2000, 162(6), 2295-2301; Gauvreau, G. M., et al., Am. J. Resp. Crit. Care Med. 2000, 161(5), 1473-1478; Kassel, O., et al., Clin. Exp. Allergy 2001, 31(9), 1432-1440). In addition, it is known that in response to allergens there is a redistribution of mast cells to the epithelial lining of the nasal mucosa (Fokkens, W. J., et al., Clin. Exp. Allergy 1992, 22(7), 701-710; Slater, A., et al., J. Laryngol. Otol. 1996, 110, 929-933). These results show that the chemotactic response of mast cells to histamine is mediated by histamine $H_4$ receptors.

It has been shown that eosinophils can chemotax towards histamine (O'Reilly, M., et al., J. Recept. Signal Transduction 2002, 22(1-4), 431-448; Buckland, K. F., et al., Br. J. Pharmacol. 2003, 140(6), 1117-1127; Ling et al., 2004). Using $H_4$ selective ligands, it has been shown that histamine-induced chemotaxis of eosinophils is mediated through the $H_4$ receptor (Buckland, et al., 2003; Ling et al., 2004). Cell surface expression of adhesion molecules CD11b/CD18 (LFA-1) and CD54 (ICAM-1) on eosinophils increases after histamine treatment (Ling, et al., 2004). This increase is blocked by $H_4$ receptor antagonists but not by $H_1$, $H_2$, or $H_3$ receptor antagonists.

The $H_4R$ also plays a role in dendritic cells and T cells. In human monocyte-derived dendritic cells, $H_4R$ stimulation suppresses IL-12p70 production and drives histamine-mediated chemotaxis (Gutzmer, R., et al., J. Immunol. 2005, 174 (9), 5224-5232). A role for the $H_4$ receptor in $CD8^+$ T cells has also been reported. Gantner, et al., (2002) showed that both $H_4$ and $H_2$ receptors control histamine-induced IL-16 release from human $CD8^+$ T cells. IL-16 is found in the bronchoalveolar fluid of allergen- or histamine-challenged asthmatics (Mashikian, V. M., et al., J. Allergy Clin. Immunol. 1998, 101 (6, Part 1), 786-792; Krug, N., et al., Am. J. Resp. Crit. Care Med. 2000, 162(1), 105-111) and is considered important in $CD4^+$ cell migration. The activity of the receptor in these cell types indicates an important role in adaptive immune responses such as those active in autoimmune diseases.

In vivo $H_4$ receptor antagonists were able to block neutrophillia in zymosan-induced peritonitis or pleurisy models (Takeshita, K., et al., J. Pharmacol. Exp. Ther. 2003, 307(3), 1072-1078; Thurmond, et al., 2004). In addition, $H_4$ receptor antagonists have activity in a widely used and well-characterized model of colitis (Varga, C., et al., Eur. J. Pharmacol. 2005, 522(1-3), 130-138). These results support the conclusion that $H_4$ receptor antagonists have the capacity to be anti-inflammatory in vivo.

Another physiological role of histamine is as a mediator of itch and $H_1$ receptor antagonists are not completely effective in the clinic. Recently, the $H_4$ receptor has also been implicated in histamine-induced scratching in mice (Bell, J. K., et al., Br. J. Pharmacol. 2004, 142(2), 374-380). The effects of histamine could be blocked by $H_4$ antagonists. These results support the hypothesis that the $H_4$ receptor is involved in histamine-induced itch and that $H_4$ receptor antagonists will therefore have positive effects in treating pruritis. Histamine $H_4$ receptor antagonists have been shown to attenuate experimental pruritis (Dunford, P. J. et al. J. Allergy Clin. Immunol. 2007, 119(1), 176-183).

Modulation of $H_4$ receptors controls the release of inflammatory mediators and inhibits leukocyte recruitment, thus providing the ability to prevent and/or treat $H_4$-mediated diseases and conditions, including the deleterious effects of allergic responses such as inflammation. Compounds according to the present invention have $H_4$ receptor modulating properties. Compounds according to the present invention have leukocyte recruitment inhibiting properties. Compounds according to the present invention have anti-inflammatory properties.

Examples of textbooks on the subject of inflammation include: 1) Gallin, J. I.; Snyderman, R., *Inflammation: Basic Principles and Clinical Correlates*, 3rd ed.; Lippincott Williams & Wilkins: Philadelphia, 1999; 2) Stvrtinova, V., et al., Inflammation and Fever. *Pathophysiology Principles of Diseases* (Textbook for Medical Students); Academic Press: New York, 1995; 3) Cecil; et al. *Textbook Of Medicine,* 18th ed.; W.B. Saunders Co., 1988; and 4) Stedman's Medical-Dictionary.

Background and review material on inflammation and conditions related with inflammation can be found in articles such as the following: Nathan, C., Nature 2002, 420(6917), 846-852; Tracey, K. J., Nature 2002, 420(6917), 853-859; Coussens, L. M., et al., Nature 2002, 420(6917), 860-867; Libby, P., Nature 2002, 420, 868-874; Benoist, C., et al., Nature 2002, 420(6917), 875-878; Weiner, H. L., et al., Nature 2002, 420(6917), 879-884; Cohen, J., Nature 2002, 420(6917), 885-891; Steinberg, D., Nature Med. 2002, 8(11), 1211-1217.

Thus, small-molecule histamine $H_4$ receptor modulators according to this invention control the release of inflammatory mediators and inhibit leukocyte recruitment, and may be useful in treating inflammation of various etiologies, including the following conditions and diseases: inflammatory disorders, allergic disorders, dermatological disorders, autoimmune disease, lymphatic disorders, pruritis, and immunodeficiency disorders. Diseases, disorders and medical conditions that are mediated by histamine $H_4$ receptor activity include those referred to herein.

Certain cyclic amine-substituted 2-aminopyrimidines are disclosed in the following publications: Becker, I. J. Het. Chem. 2005, 42(7), 1289-1295; Eur. Pat. Appl. No. EP 1437348 (Jul. 14, 2004); U.S. Pat. No. 3,907,801 (Sep. 23, 1975); Lespagnol, A. et al. Chim. Therap. 1971, 6(2), 105-108; Willecomme, B. Annales de Chimie 1969, 4(6), 405-428; Lespagnol, A. et al. Chim. Therap. 1965, 1, 26-31; Intl. Pat. Appl. Publ. WO 2001/62233 (Aug. 30, 2007); and Intl. Pat. Appl. Publ. WO 2001/47921 (Jul. 5, 2001).

Certain substituted 2-aminopyrimidines as histamine $H_4$ antagonists are disclosed in Intl. Pat. Appl. Publ. WO2005/054239 (Jun. 16, 2005) and EP 1505064 (Feb. 9, 2005; equivalent of Intl. Pat. Appl. Publ. WO2005/014556). Substituted pyrimidines are described as histamine $H_4$ ligands in U.S. Pat. Appl. Publ. 2007/0185075 (Aug. 9, 2007) and Intl. Pat. Appl. Publ. WO2007/031529 (Mar. 22, 2007). Benzofuro- and benzothienopyrimidines are disclosed as histamine $H_4$ modulators in Intl. Pat. Appl. Publ. WO2008/008359 (Jan. 17, 2008). Additional disclosures of amino pyrimidines as histamine $H_4$ ligands include: Intl. Pat. Appl. Publ. Nos. WO2007/090852, WO2007/090853, and WO2007/090854 (Aug. 16, 2007), and EP 1767537 (Mar. 28, 2007).

However, there remains a need for potent histamine $H_4$ receptor modulators with desirable pharmaceutical properties. Certain 2-aminopyrimidine derivatives have been found in the context of this invention to have histamine $H_4$ receptor-modulating activity.

SUMMARY OF THE INVENTION

In one aspect the invention relates to chemical entity selected from compounds of the following Formula (I):

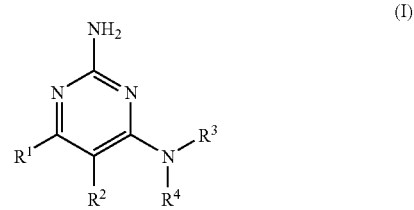

wherein $R^1$ is:

a) a $C_{1-6}$alkyl group, optionally substituted with —OH, —OC$_{1-4}$alkyl, —CF$_3$, or —O-(monocyclic cycloalkyl);

b) a benzyl, —CH$_2$-(monocyclic heteroaryl), or phenethyl group, each optionally substituted with halo;

c) a monocyclic cycloalkyl, —(CH$_2$)$_{0-1}$-tetrahydrofuranyl, or —(CH$_2$)$_{0-1}$-tetrahydropyranyl group, each optionally fused to a phenyl ring, and each optionally substituted with $C_{1-4}$alkyl or phenyl; or d) an adamantyl group;

$R^2$ is H, F, methyl, or methoxy;

or $R^1$ and $R^2$ taken together form —(CH$_2$)$_{3-5}$— or —(CH$_2$)$_2$OCH$_2$—; and —N(R$^3$)R$^4$ is one of the following acyclic, monocyclic, spirocyclic, bridged, or fused ring systems:

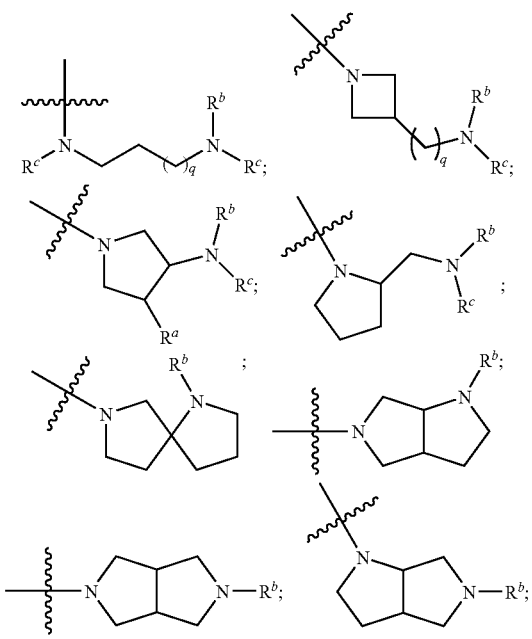

-continued

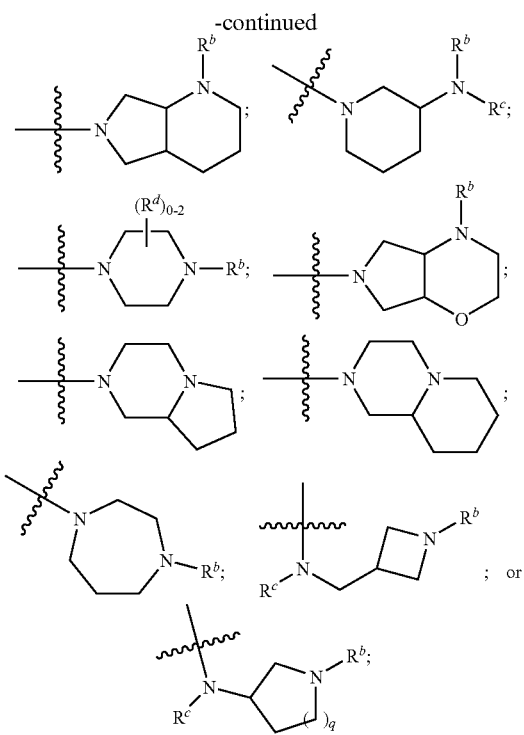

where q is 0 or 1;
R³ and R⁴ are taken together as defined by the structure of each one of such moieties;
$R^a$ is H or OH;
$R^b$ and $R^c$ are each independently H or $C_{1-3}$alkyl; and
each $R^d$ substitutuent is methyl or two $R^d$ substituents taken together form a methylene or ethylene bridge;
provided that when $R^1$ is methyl, then —N($R^3$)$R^4$ is selected from said spirocyclic, bridged, and fused ring systems;
and pharmaceutically acceptable salts of compounds of Formula (I), pharmaceutically acceptable prodrugs of compounds of Formula (I), and pharmaceutically active metabolites of Formula (I).

In certain embodiments, the compound of Formula (I) is a compound selected from those species described or exemplified in the detailed description below.

In a further aspect, the invention relates to pharmaceutical compositions each comprising an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of Formula (I). Pharmaceutical compositions according to the invention may further comprise a pharmaceutically acceptable excipient.

In another aspect, the invention is directed to a method of treating a subject suffering from or diagnosed with a disease, disorder, or medical condition mediated by histamine $H_4$ receptor activity, comprising administering to the subject in need of such treatment an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In certain preferred embodiments of the inventive method, the disease, disorder, or medical condition is inflammation.

Inflammation herein refers to the response that develops as a consequence of histamine release, which in turn is caused by at least one stimulus. Examples of such stimuli are immunological stimuli and non-immunological stimuli.

In another aspect, the chemical entities of the present invention are useful as histamine $H_4$ receptor modulators. Thus, the invention is directed to a method for modulating histamine $H_4$ receptor activity, including when such receptor is in a subject, comprising exposing histamine $H_4$ receptor to an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In another aspect, the present invention is directed to methods of making compounds of Formula (I) and pharmaceutically acceptable salts thereof.

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION OF THE INVENTION AND ITS PREFERRED EMBODIMENTS

For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by a bond, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

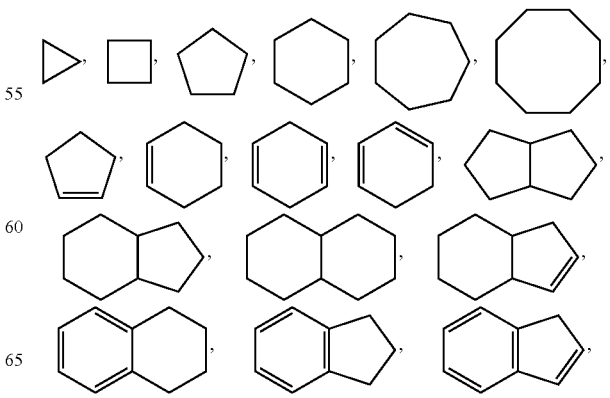

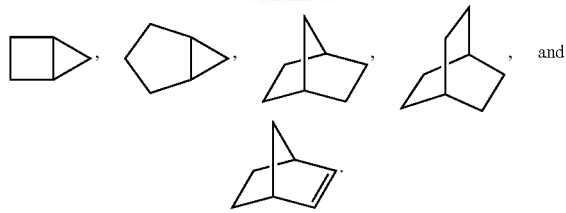

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

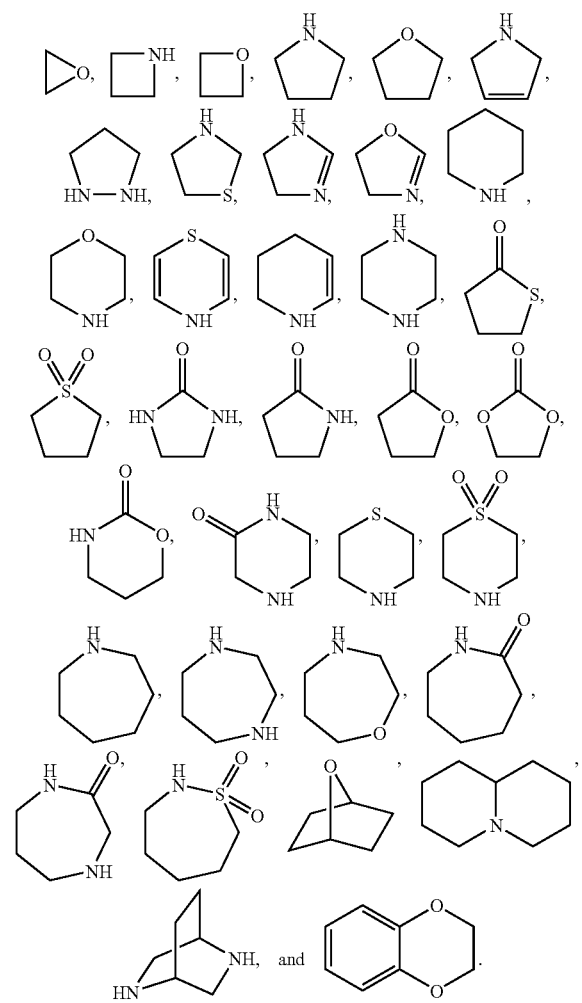

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

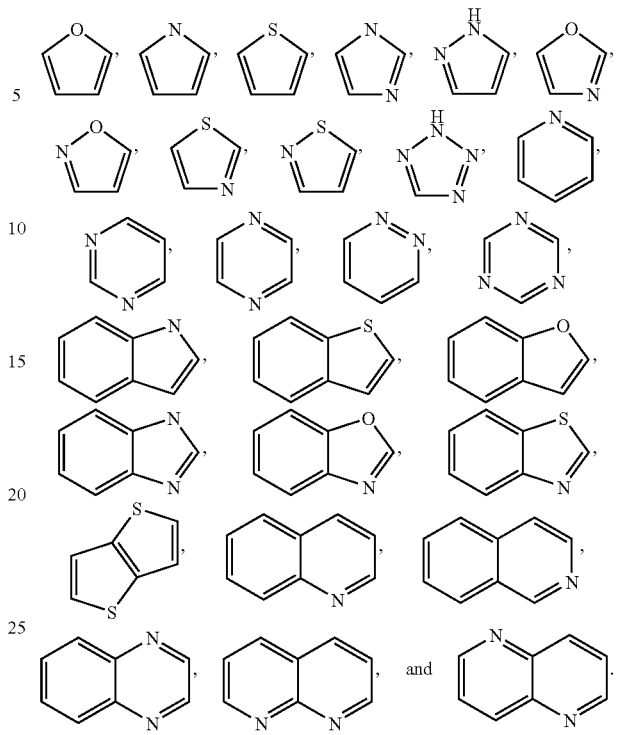

Those skilled in the art will recognize that the species of heteroaryl, cycloalkyl, and heterocycloalkyl groups listed or illustrated above are not exhaustive, and that additional species within the scope of these defined terms may also be selected.

The term "halogen" represents chlorine, fluorine, bromine, or iodine. The term "halo" represents chloro, fluoro, bromo, or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to represent hydrates, solvates, and polymorphs of such compounds, and mixtures thereof. In certain embodiments of the invention, pharmaceutically acceptable salts of compounds of Formula (I) were obtained in a crystalline form. In a preferred embodiment, bis hydrochloride salts of compounds of Formula (I) were obtained in a crystalline form.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-$$_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-$$_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In this regard, if such entity is for example in an aqueous environment, it is understood that the compound R—COOH is in such same medium, and therefore the entity is being exposed to species such as R—COOH$_{(aq)}$ and/or R—COO$^-$$_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^{1-4}$, $R^{a-d}$, and q, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^{1-4}$, $R^{a-d}$, and q, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members (C$_2$), and embodiments that have three carbon members (C$_3$).

The term C$_{n-m}$alkyl refers to an aliphatic chain, whether straight or branched, with a total number N of carbon members in the chain that satisfies n≦N≦m, with m>n.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

In some embodiments of Formula (I), R$^1$ is methyl, ethyl, propyl, isopropyl, butyl, isobutyl, tert-butyl, methoxymethyl, ethoxymethyl, isopropoxymethyl, tert-butoxymethyl, 3,3,3-trifluoropropyl, cyclopropoxymethyl, benzyl, 4-chlorobenzyl, thiophen-2-ylmethyl, thiophen-3-ylmethyl, pyridin-4-ylmethyl, phenethyl, cyclopropyl, cyclobutyl, cyclopentyl, cyclohexyl, 2-phenyl-cyclopropyl, indan-2-yl, tetrahydrofuran-3-yl, tetrahydropyran-4-yl, 4-methyl-tetrahydro-pyran-4-yl, 2,3-dihydro-benzofuran-2-yl, tetrahydrofuran-2-ylmethyl, or adamantyl. In other embodiments, R$^1$ is cyclopropyl, cyclobutyl, cyclopentyl, or cyclohexyl.

In some embodiments, R$^2$ is H.
In some embodiments, R$^1$ and R$^2$ taken together form —(CH$_2$)$_4$—. In other embodiments, R$^1$ and R$^2$ taken together form —(CH$_2$)$_2$OCH$_2$—.
In some embodiments, —N(R$^3$)R$^4$ is:

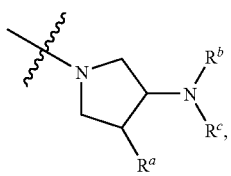

where R$^a$, R$^b$, and R$^c$ are as previously defined. In further embodiments, —N(R$^3$)R$^4$ is:

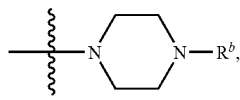

where R$^b$ is as previously defined. In still further embodiments, —N(R$^3$)R$^4$ is:

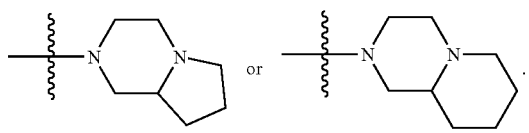

In still further embodiments, —N(R$^3$)R$^4$ is:

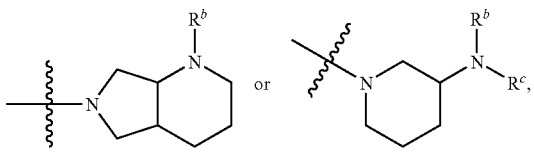

where R$^b$ and R$^c$ are as previously defined. In still further embodiments, —N(R$^3$)R$^4$ is:

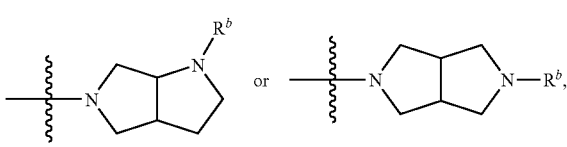

where R$^b$ is as previously defined. In still further embodiments, —N(R$^3$)R$^4$ is:

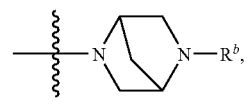

where R$^b$ is as previously defined. In still further embodiments, —N(R$^3$)R$^4$ is:

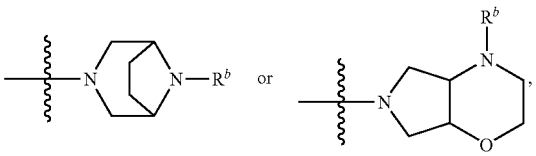

where R$^b$ is as previously defined.
In some embodiments, R$^a$ is H.
In some embodiments, R$^b$ and R$^c$ are each independently H or methyl.

The invention includes also pharmaceutically acceptable salts of the compounds represented by Formula (I), preferably of those described above and of the specific compounds exemplified herein, and methods using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, meta phosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

Where the compound of Formula (I) contains a plurality of basic nitrogens, one skilled in the art will recognize that suitable salts include salts formed with one or more equivalents of an inorganic or organic acid. In preferred embodiments of Formula (I), such salts include bis hydrochloride salts.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to pharmaceutically active metabolites of compounds of Formula (I), and uses of such metabolites in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J. Med. Chem.* 1997, 40, 2011-2016; Shan, et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites, whether alone or in combination, (collectively, "active agents") of the present invention are useful as histamine $H_4$ receptor modulators in the methods of the invention. Such methods for modulating histamine $H_4$ receptor activity comprise exposing histamine $H_4$ receptor to an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Embodiments of this invention inhibit histamine $H_4$ receptor activity.

In some embodiments, the histamine $H_4$ receptor is in a subject diagnosed with or suffering from a disease, disorder, or medical condition mediated through histamine $H_4$ receptor activity, such as those described herein. Symptoms or disease states are intended to be included within the scope of "medical conditions, disorders, or diseases."

Accordingly, the invention relates to methods of using the active agents described herein to treat subjects diagnosed with or suffering from a disease, disorder, or condition mediated through histamine $H_4$ receptor activity, such as inflammation. Active agents according to the invention may therefore be used as anti-inflammatory agents.

In some embodiments, an active agent of the present invention is administered to treat inflammation. Inflammation may be associated with various diseases, disorders, or conditions, such as inflammatory disorders, allergic disorders, dermatological disorders, autoimmune disease, lymphatic disorders, and immunodeficiency disorders, including the more specific conditions and diseases given below. Regarding the onset and evolution of inflammation, inflammatory diseases or inflammation-mediated diseases or conditions include, but are not limited to, acute inflammation, allergic inflammation, and chronic inflammation.

Illustrative types of inflammation treatable with a histamine $H_4$ receptor-modulating agent according to the invention include inflammation due to any one of a plurality of conditions such as allergy, asthma, dry eye, chronic obstructed pulmonary disease (COPD), atherosclerosis, rheumatoid arthritis (see: Ohki, E. et al. Biol. Pharm. Bull. 2007, 30(11), 2217-2220), multiple sclerosis, inflammatory bowel diseases (including colitis, Crohn's disease, and ulcerative colitis), psoriasis, pruritis, itchy skin, atopic dermatitis, urticaria (hives), ocular inflammation (e.g., post-surgical ocular inflammation), conjunctivitis, dry eye, nasal polyps, allergic rhinitis, nasal itch, scleroderma, autoimmune thyroid diseases, immune-mediated (also known as type 1) diabetes mellitus and lupus, which are characterized by excessive or prolonged inflammation at some stage of the disease. Other autoimmune diseases that lead to inflammation include Myasthenia gravis, autoimmune neuropathies, such as Guillain-Barré, autoimmune uveitis, autoimmune hemolytic anemia, pernicious anemia, autoimmune thrombocytopenia, temporal arteritis, anti-phospholipid syndrome, vasculitides, such as Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, such as ankylosing spondylitis, and Sjogren's syndrome.

Pruritis treatable with a histamine $H_4$ receptor-modulating agent according to the invention includes that which is a symptom of allergic cutaneous diseases (such as atopic dermatitis and hives) and other metabolic disorders (such as chronic renal failure, hepatic cholestasis, and diabetes mellitus).

In other embodiments, an active agent of the present invention is administered to treat allergy, rheumatoid arthritis, asthma, autoimmune diseases, or pruritis.

Thus, the active agents may be used to treat subjects diagnosed with or suffering from a disease, disorder, or condition mediated through histamine $H_4$ receptor activity. The term "treat" or "treating" as used herein is intended to refer to administration of an active agent or composition of the invention to a subject for the purpose of effecting a therapeutic or prophylactic benefit through modulation of histamine $H_4$ receptor activity. Treating includes reversing, ameliorating, alleviating, inhibiting the progress of, lessening the severity of, or preventing a disease, disorder, or condition, or one or more symptoms of such disease, disorder or condition mediated through modulation of histamine $H_4$ receptor activity. The term "subject" refers to a mammalian patient in need of such treatment, such as a human. "Modulators" include both inhibitors and activators, where "inhibitors" refer to compounds that decrease, prevent, inactivate, desensitize or down-regulate histamine $H_4$ receptor expression or activity, and "activators" are compounds that increase, activate, facilitate, sensitize, or up-regulate histamine $H_4$ receptor expression or activity.

In treatment methods according to the invention, an effective amount of at least one active agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.001 to about 200 mg of active agent per kg of subject's body weight per day, preferably about 0.05 to 100 mg/kg/day, or about 1 to 35 mg/kg/day, or about 0.1 to 10 mg/kg daily in single or divided dosage units (e.g., BID, TID, QID). For a 70-kg human, an illustrative range for a suitable dosage amount is from about 1 to 200 mg/day, or about 5 to 50 mg/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of Formula (I) or included with such an agent in a pharmaceutical composition according to the invention. In an exemplary embodiment, additional active ingredients are those that are known or discovered to be effective in the treatment of conditions, disorders, or diseases mediated by histamine $H_4$ receptor activity, such as another histamine $H_4$ receptor modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the active agent according to the invention.

When referring to modulating the target receptor, an "effective amount" means an amount sufficient to affect the activity of such receptor. Measuring the activity of the target receptor may be performed by routine analytical methods. Target receptor modulation is useful in a variety of settings, including assays.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the active agents of the invention can be provided in the form of tablets or capsules, or as a solution, emulsion, or suspension. To prepare the oral compositions, the active agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Each of the reactions depicted in Scheme A is preferably run at a temperature from about room temperature to the reflux temperature of the organic solvent used. Unless otherwise specified, the variables are as defined above in reference to Formula (I).

SCHEME A

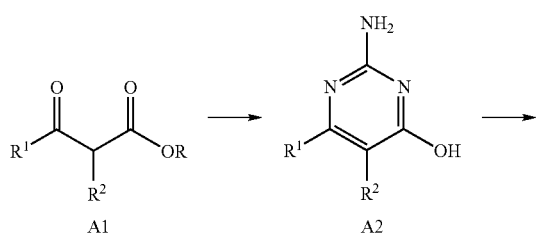

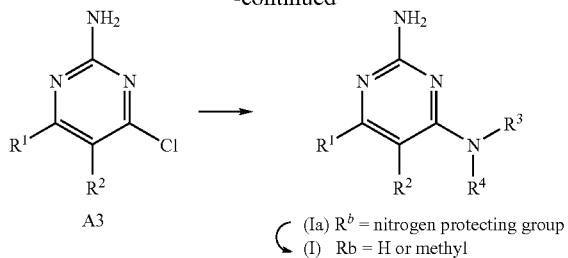

(Ia) $R^b$ = nitrogen protecting group
(I) Rb = H or methyl

As shown in Scheme A, the present invention includes methods of making compounds of Formula (I), from β-ketoesters A1 (where R is $C_{1-4}$alkyl; preferably methyl or ethyl), which are commercially available or prepared by known methods. β-Ketoesters A1 are reacted with guanidine, or a hydrochloride, carbonate, nitrate, or sulfate salt thereof, in the presence of an organic base (for example, potassium tert-butoxide or a tertiary amine base, such as triethylamine or diisopropylethylamine) or an inorganic base (for example, $K_2CO_3$, $Na_2CO_3$, $Cs_2CO_3$, or $K_3PO_4$, or a mixture thereof), in an organic solvent (for example, methanol, ethanol, isopropanol, tert-amyl alcohol, THF, acetonitrile, or methyl tert-butyl ether (MTBE), or a mixture thereof), to provide hydroxypyrimidines A2. One skilled in the art will recognize that compounds of formula A2 include hydroxypyrimidines and their pyrimidone tautomers, and mixtures thereof.

Chlorination of compounds A2 with $POCl_3$, neat or in an organic solvent (for example, acetonitrile, toluene, dichloromethane, or MTBE, or a mixture thereof), provides chloropyrimidines A3. In preferred embodiments, the reaction is done in the presence of a tertiary amine base (for example, dimethylaniline, diethylaniline, or $iPr_2NEt$) and a tetraalkylammonium chloride salt (such as $Et_4NCl$).

Displacement of the chloro substituent by reacting a chloro-pyrimidine A3 with a diamine $HNR^3R^4$, in an organic solvent (for example, methanol, ethanol, isopropanol, tert-amyl alcohol, THF, or acetonitrile, or a mixture thereof), gives compounds of Formula (I). In some embodiments of the displacement reaction, the $R^b$ substituent in diamine $HNR^3R^4$ is a nitrogen protecting group, such as a tert-butoxycarbonyl (Boc) group or benzyl group, and the reaction provides compounds of formula (Ia) where $R^b$ is a nitrogen protecting group.

Where the $R^b$ group in diamine $HNR^3R^4$ is a nitrogen protecting group, the protecting group is removed by deprotecting compounds of formula (Ia) to give compounds of Formula (I) where $R^b$ is H. Deprotection may be accomplished using standard deprotection conditions. For example, a tert-butoxycarbonyl group is removed using an organic acid such as TFA (neat or in a solvent such as $CH_2Cl_2$) or an inorganic acid such as HCl (in a solvent such as 1,4-dioxane, isopropanol, or formic acid) to give a compound of Formula (I) where $R^b$ is H.

In an alternative embodiment, reaction of hydroxypyrimidines A2 with protected or unprotected diamines $HNR^3R^4$ under standard peptide coupling conditions known in the art provide compounds of Formula (I) directly.

Compounds of Formula (I) may be converted to their corresponding salts using methods described in the art. For example, an amine of Formula (I) is treated with trifluoroacetic acid, HCl, or citric acid in a solvent such as $Et_2O$, $CH_2Cl_2$, THF, MeOH, or isopropanol to provide the corresponding salt form. Crystalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions are "dried," they are generally dried over a drying agent such as $Na_2SO_4$ or $MgSO_4$. Where mixtures, solutions, and extracts were "concentrated", they were typically concentrated on a rotary evaporator under reduced pressure. Silica gel ($SiO_2$) was used for all chromatographic purification unless otherwise noted and the eluent used is listed in parentheses.

Analytical reversed-phase HPLC was performed on a Hewlett Packard HPLC Series 1100, with a Phenomenex ONYX® monolithic C18 (5 μm, 4.6×100 mm) column. Detection was done at λ=230, 254 and 280 nm. The flow rate was 1 mL/min. The gradient was 10 to 90% acetonitrile/water (20 mM $NH_4OH$) over 5.0 min. Preparative reversed-phase HPLC was performed on a Shimadzu LC-8A equipped with a YMC Pack ODS 250×30 mm column with a gradient of 10 to 50% TFA in acetonitrile (0.05% water) over 15 min at a flow rate of 70 mL/min.

Compounds were analyzed in a free base, hydrochloride salt, or trifluoroacetic acid salt form. Hydrochloride salts were obtained either: 1) during the removal of the tert-butylcarbamoyl (Boc) group; or 2) by treatment of a solution of the purified free base in THF or $CH_2Cl_2$ with at least two equivalents of a solution of HCl in 1,4-dioxane followed by concentration. TFA salts were obtained following preparative reversed-phase HPLC purification.

Nuclear magnetic resonance (NMR) spectra were obtained on Bruker model DRX spectrometers. The format of the $^1H$ NMR data below is: chemical shift in ppm downfield of the tetramethylsilane reference (multiplicity, coupling constant J in Hz, integration).

Mass spectra were obtained on an Agilent series 1100 MSD using electrospray ionization (ESI) in either positive or negative modes as indicated. The MS data presented is the m/z found (typically $[M+H]^+$) for the molecular ion.

Chemical names were generated using ChemDraw Version 6.0.2 (CambridgeSoft, Cambridge, Mass.) or ACD/Name Version 9 (Advanced Chemistry Development, Toronto, Ontario, Canada).

Example 1

4-Cyclopentyl-6-piperazin-1-yl-pyrimidin-2-ylamine

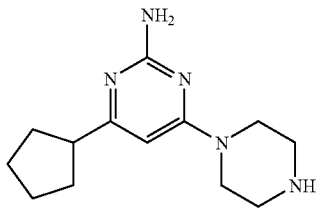

Step A: 2-Amino-6-cyclopentyl-3H-pyrimidin-4-one. To a solution of 3-cyclopentyl-3-oxo-propionic acid ethyl ester (5.0 g, 27.4 mmol) and guanidine hydrochloride (3.1 g, 33.0 mmol) in MeOH (50 mL) at 23° C. was added potassium tert-butoxide, portionwise (16.7 g. 149 mmol) over 15 min with vigorous stirring and the reaction warmed to 60° C. The reaction was cooled to room temperature (rt) and stirred overnight and the precipitated salt was removed by filtration. The solution was concentrated to approximately 10 mL then diluted with 10 mL of water and adjusted to pH=5 by the addition of 6.0 N HCl (6.1 mL). The resulting precipitate was filtered and dried via suction then vacuum to yield a white solid (4.3 g, 87%) that was used without further purification. $^1$H NMR (MeOD): 10.71-10.54 (m, 1H), 6.58-6.32 (m, 2H), 5.44-5.37 (m, 1H), 2.66 (p, J=8.1, 1H), 1.91-1.73 (m, 2H), 1.72-1.48 (m, 6H).

Step B: 2-Amino-4-chloro-6-cyclopentylpyrimidine. A suspension of 2-amino-6-cyclopentyl-3H-pyrimidin-4-one (1.52 g, 8.4 mmol), tetraethyl ammonium chloride (2.8 g 16.9 mmol) and dimethylaniline (1.1 mL, 8.4 mmol) in acetonitrile (16 mL) was treated with phosphorous oxychloride (4.7 mL, 51 mmol) and heated at 110° C. for 20 min. The resulting solution was cooled to rt and concentrated to minimum volume then diluted with CHCl$_3$ and ice and stirred for 30 min. The layers were separated and the organic layer was washed with water (3×50 mL) and 5% NaHCO$_3$, dried, and concentrated to yield 2.0 g of crude product that was used without purification.

Step C: 4-Cyclopentyl-6-piperazin-1-yl-pyrimidin-2-ylamine. A solution of crude 2-amino-4-chloro-6-cyclopentylpyrimidine (150 mg, 0.76 mmol), N-BOC piperazine (184 mg, 0.99 mmol) and Et$_3$N (210 uL, 1.5 mmol) in EtOH (2 mL) was heated at 70° C. for 16 h. The reaction was cooled to rt and concentrated and the crude residue purified (2 M NH$_3$ in MeOH/CH$_2$Cl$_2$) to yield a white solid (34 mg, 11%). MS (ESI): mass calcd. for C$_{18}$H$_{29}$N$_5$O$_2$, 347.2; m/z found, 348.3 [M+H]$^+$. $^1$H NMR (MeOD): 6.01 (s, 1H), 3.66-3.58 (m, 4H), 3.53-3.43 (m, 4H), 3.33 (td, J=3.3, 1.6, 1H), 2.90-2.75 (m, 1H), 2.05-1.90 (m, 2H), 1.87-1.77 (m, 2H), 1.77-1.62 (m, 4H), 1.53-1.46 (m, 9H).

Step D: 4-Cyclopentyl-6-piperazin-1-yl-pyrimidin-2-ylamine. A solution of 4-cyclopentyl-6-piperazin-1-yl-pyrimidin-2-ylamine (34 mg, 0.10 mmol) in formic acid (3 mL) was treated with 6.0 N HCl (0.1 mL) and stirred for 2 h. The reaction was diluted with MeOH and concentrated. This process was repeated twice to remove the formic acid to yield a white solid (30 mg, 97%). MS (ESI): mass calcd. for C$_{13}$H$_{21}$N$_5$, 247.2; m/z found, 248.2 [M+H]$^+$. $^1$H NMR (MeOD): 6.45 (s, 1H), 4.34-4.16 (m, 2H), 4.13-3.96 (m, 2H), 3.42-3.34 (m, 4H), 3.03 (p, J=8.0, 1H), 2.22-2.08 (m, 2H), 1.99-1.83 (m, 2H), 1.83-1.65 (m, 4H).

Example 2

4-Cyclopentyl-6-(4-methyl-piperazin-1-yl)-pyrimidin-2-ylamine

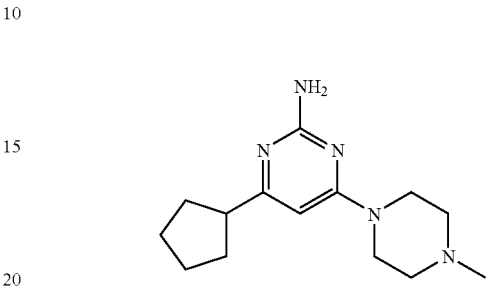

A solution of crude 2-amino-4-chloro-6-cyclopentylpyrimidine (92 mg, 0.47 mmol), and N-methyl piperazine (0.15 mL, 1.4 mmol) in EtOH (2 mL) was heated at 70° C. for 2 h. The reaction was cooled to rt and concentrated and the crude residue chromatographed (2 M NH$_3$ in MeOH/CH$_2$Cl$_2$) to yield an oil (81 mg, 66%). MS (ESI): mass calcd. for C$_{14}$H$_{23}$N$_5$, 261.2; m/z found, 262.3 [M+H]$^+$. $^1$H NMR (CDCl$_3$): 5.85 (s, 1H), 4.78 (s, 2H), 3.59 (t, J=5.0, 4H), 2.81 (q, J=8.7, 1H), 2.44 (t, J=5.0, 4H), 2.32 (s, 3H), 2.04-1.89 (m, 2H), 1.82-1.59 (m, 6H).

The compounds in Examples 3-36 were prepared using methods analogous to those described for Examples 1 and 2. Where amines used in Example 1, Step C or Example 2 were not protected, the deprotection step described in Example 1, Step D was omitted.

Example 3

(R)-4-(3-Amino-piperidin-1-yl)-6-cyclopentyl-pyrimidin-2-ylamine

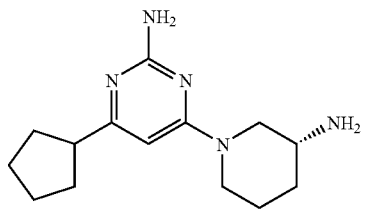

MS (ESI): mass calcd. for C$_{14}$H$_{23}$N$_5$, 261.2; m/z found, 262.2 [M+H]$^+$.

Example 4

(R)-4-Cyclopentyl-6-(3-methylamino-pyrrolidin-1-yl)-pyrimidin-2-ylamine

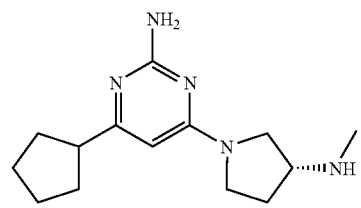

MS (ESI): mass calcd. for $C_{14}H_{23}N_5$, 261.4; m/z found, 262.3 [M+H]+. 1H NMR (MeOD): 5.75 (s, 1H), 3.74-3.51 (m, 2H), 3.52-3.39 (m, 1H), 3.37-3.30 (m, 2H), 2.86-2.75 (m, 1H), 2.41 (s, 3H), 2.27-2.14 (m, 1H), 2.05-1.92 (m, 2H), 1.93-1.83 (m, 1H), 1.84-1.73 (m, 2H), 1.73-1.60 (m, 4H).

Example 5 trans-1-(2-Amino-6-cyclopentyl-pyrimidin-4-yl)-4-methylamino-pyrrolidin-3-ol

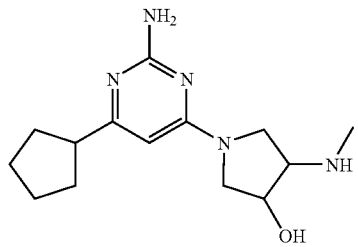

MS (ESI): mass calcd. for $C_{14}H_{23}N_5O$, 277.2; m/z found, 278.1 [M+H]+. 1H NMR (CDCl3): 5.52 (s, 1H), 5.34-5.17 (m, 2H), 4.17-4.07 (m, 1H), 3.75-3.56 (m, 2H), 3.40-3.08 (m, 4H), 3.10-3.02 (m, 1H), 2.78-2.66 (m, 1H), 2.37 (s, 3H), 1.96-1.84 (m, 2H), 1.75-1.63 (m, 2H), 1.63-1.49 (m, 4H).

Example 6

4-Cyclopentyl-6-(cis-hexahydro-pyrrolo[3,4-b]pyrrol-5-yl)-pyrimidin-2-ylamine

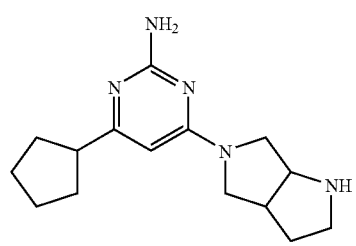

MS (ESI): mass calcd. for $C_{15}H_{23}N_5$, 273.2; m/z found, 274.2 [M+H]+. 1H NMR (CDCl3): 5.63 (s, 1H), 5.36-5.13 (m, 2H), 3.97-3.85 (m, 1H), 3.78-3.63 (m, 1H), 3.64-3.54 (m, 1H), 3.56-3.42 (m, 1H), 3.38-3.22 (m, 1H), 3.20-3.04 (m, 2H), 3.05-2.92 (m, 2H), 2.92-2.75 (m, 2H), 2.11-1.89 (m, 3H), 1.86-1.57 (m, 7H).

Example 7

4-Cyclopentyl-6-(cis-octahydro-pyrrolo[3,4-b]pyridin-6-yl)-pyrimidin-2-ylamine

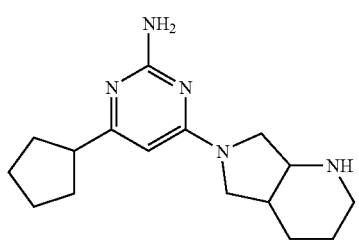

MS (ESI): mass calcd. for $C_{16}H_{25}N_5$, 287.2; m/z found, 288.2 [M+H]+. 1H NMR (MeOD): 6.13 (s, 1H), 4.13-4.04 (m, 1H), 4.02-3.79 (m, 3H), 3.71-3.58 (m, 1H), 3.42-3.34 (m, 1H), 3.17-2.79 (m, 3H), 2.22-2.09 (m, 2H), 2.03-1.68 (m, 10H).

Example 8

4-Isopropyl-6-piperazin-1-yl-pyrimidin-2-ylamine

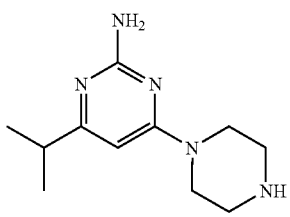

MS (ESI): mass calcd. for $C_{11}H_{19}N_5$, 221.2; m/z found, 222.1 [M+H]+. 1H NMR (MeOD): 5.99 (s, 1H), 3.66-3.62 (m, 4H), 2.93-2.84 (m, 4H), 2.67 (q, J=7.0, 1H), 1.21 (d, J=7.0, 6H).

Example 9

(R)-4-(3-Amino-piperidin-1-yl)-6-isopropyl-pyrimidin-2-ylamine

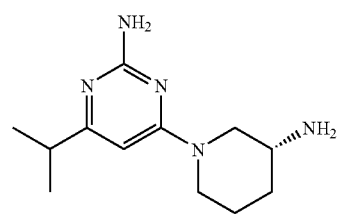

MS (ESI): mass calcd. for $C_{12}H_{21}N_5$, 235.2; m/z found, 236.2 [M+H]+.

Example 10

(S)-4-(3-Amino-piperidin-1-yl)-6-isopropyl-pyrimidin-2-ylamine

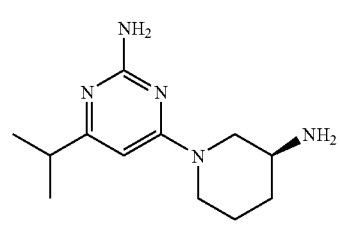

MS (ESI): mass calcd. for $C_{12}H_{21}N_5$, 235.2; m/z found, 236.2 [M+H]+.

Example 11

(R)-4-Isopropyl-6-(3-methylamino-pyrrolidin-1-yl)-pyrimidin-2-ylamine

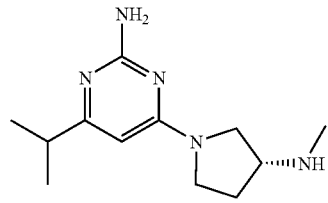

MS (ESI): mass calcd. for $C_{12}H_{21}N_5$, 235.2; m/z found, 236.2 [M+H]+. $^1$H NMR (CDCl$_3$): 5.66 (s, 1H), 5.00-4.87 (m, 2H), 3.75-3.56 (m, 2H), 3.56-3.43 (m, 1H), 3.43-3.23 (m, 2H), 2.71 (q, J=6.9, 1H), 2.53 (s, 3H), 2.22 (dt, J=13.4, 6.1, 1H), 1.98-1.81 (m, 1H), 1.26 (d, J=6.9, 6H).

Example 12

(R)-4-(3-Amino-pyrrolidin-1-yl)-6-isopropyl-pyrimidin-2-ylamine

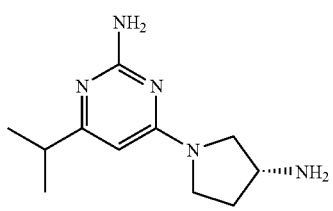

MS (ESI): mass calcd. for $C_{11}H_{19}N_5$, 221:16; m/z found, 222.2 [M+H]+. $^1$H NMR (MeOD; mixture of forms): 6.10 (s, 0.67H), 6.08 (s, 0.33H), 4.16-3.68 (m, 5H), 2.89 (sept, J=6.9, 1H), 2.60-2.50 (m, 0.67H), 2.50-2.42 (m, 0.33H), 2.32-2.22 (m, 0.67H), 2.22-2.14 (m, 0.33H), 1.33 (d, J=7.0, 6H).

Example 13 trans-1-(2-Amino-6-isopropyl-pyrimidin-4-yl)-4-methylamino-pyrrolidin-3-ol

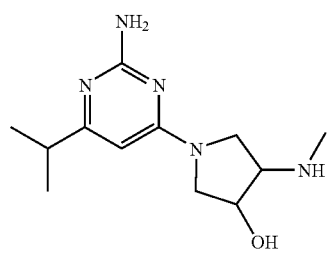

MS (ESI): mass calcd. for $C_{12}H_{21}N_5O$, 251.2 m/z found, 252.2 [M+H]+.

Example 14

(S,S)-4-(2,5-Diaza-bicyclo[2.2.1]hept-2-yl)-6-isopropyl-pyrimidin-2-ylamine

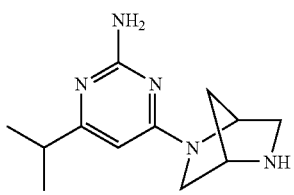

MS (ESI): mass calcd. for $C_{12}H_{19}N_5$, 233.2; m/z found, 234.2 [M+H]+.

Example 15

(R,R)-4-(2,5-Diaza-bicyclo[2.2.1]hept-2-yl)-6-isopropyl-pyrimidin-2-ylamine

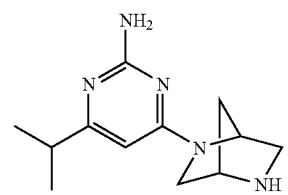

MS (ESI): mass calcd. for $C_{12}H_{19}N_5$, 233.2; m/z found, 234.2 [M+H]+.

Example 16

4-(cis-Hexahydro-pyrrolo[3,4-b]pyrrol-5-yl)-6-isopropyl-pyrimidin-2-ylamine

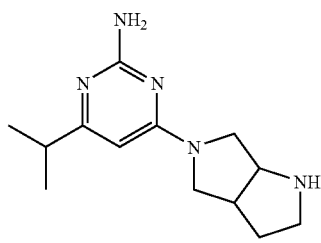

MS (ESI): mass calcd. for $C_{13}H_{21}N_5$, 247.2; m/z found, 248.2 [M+H]+.

Example 17

(R,R)-4-(Hexahydro-pyrrolo[3,4-b]pyrrol-5-yl)-6-isopropyl-pyrimidin-2-ylamine

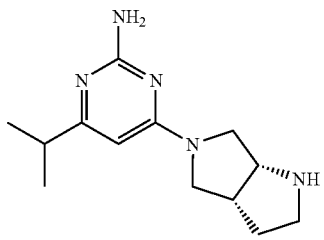

MS (ESI): mass calcd. for $C_{13}H_{21}N_5$, 247.2; m/z found, 248.2 [M+H]$^+$.

Example 18

4-Isopropyl-6-(cis-5-methyl-hexahydro-pyrrolo[3,4-c]pyrrol-2-yl)-pyrimidin-2-ylamine

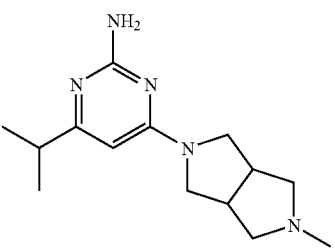

MS (ESI): mass calcd. for $C_{14}H_{23}N_5$, 261.2; m/z found, 262.2 [M+H]$^+$. $^1$H NMR (CDCl$_3$): 5.54 (s, 1H), 4.61 (s, 2H), 3.54 (dd, J=10.7, 8.2, 2H), 3.30 (d, J=10.3, 2H), 2.91-2.80 (m, 2H), 2.65-2.51 (m, 2H), 2.36 (dd, J=9.5, 3.6, 2H), 2.24 (s, 3H), 1.12 (d, J=6.9, 6H).

Example 19

4-Isopropyl-6-(cis-octahydro-pyrrolo[3,4-b]pyridin-6-yl)-pyrimidin-2-ylamine

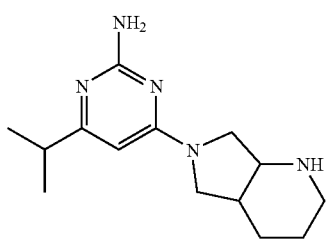

MS (ESI): mass calcd. for $C_{14}H_{23}N_5$, 261.2; m/z found, 262.2 [M+H]$^+$. $^1$H NMR (CDCl$_3$): 5.45 (s, 1H), 5.42-5.19 (m, 2H), 3.57-3.06 (m, 4H), 2.91-2.80 (m, 1H), 2.64-2.46 (m, 3H), 2.29-2.08 (m, 1H), 1.94-1.85 (m, 1H), 1.66-1.53 (m, 2H), 1.53-1.43 (m, 1H), 1.40-1.31 (m, 1H), 1.08 (d, J=6.9, 6H).

Example 20

(R,R)-4-isopropyl-6-(cis-octahydro-pyrrolo[3,4-b]pyridin-6-yl)-pyrimidin-2-ylamine

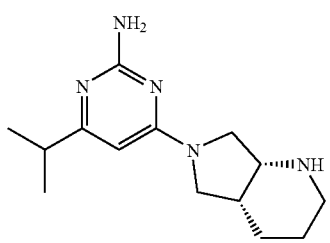

MS (ESI): mass calcd. for $C_{14}H_{23}N_5$, 261.2; m/z found, 262.2 [M+H]$^+$. $^1$H NMR (CDCl$_3$): 5.45 (s, 1H), 5.42-5.19 (m, 2H), 3.57-3.06 (m, 4H), 2.91-2.80 (m, 1H), 2.64-2.46 (m, 3H), 2.29-2.08 (m, 1H), 1.94-1.85 (m, 1H), 1.66-1.53 (m, 2H), 1.53-1.43 (m, 1H), 1.40-1.31 (m, 1H), 1.08 (d, J=6.9, 6H).

Example 21

4-Methyl-6-piperazin-1-yl-pyrimidin-2-ylamine

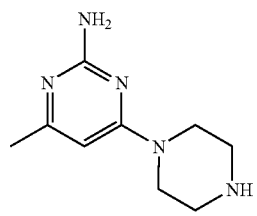

MS (ESI): mass calcd. for $C_9H_{15}N_5$, 193.2; m/z found, 194.2 [M+H]$^+$. $^1$H NMR (MeOD): 10.02-9.24 (br. s, 2H), 8.12-7.21 (br.s, 2H), 6.50 (s, 1H), 4.14-3.85 (m, 4H), 3.19 (t, J=5.0, 4H).

Example 22

4-Methyl-6-(4-methyl-piperazin-1-yl)-pyrimidin-2-ylamine

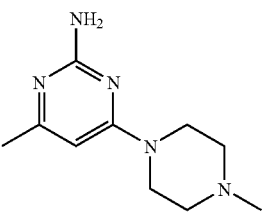

MS (ESI): mass calcd. for $C_{10}H_{17}N_5$, 207.3; m/z found, 208.2 [M+H]$^+$. $^1$H NMR (CDCl$_3$): 5.63 (s, 1H), 4.48 (s, 2H), 3.39 (t, J=5.1, 4H), 2.23 (t, J=5.1, 4H), 2.12 (s, 3H), 2.01 (s, 3H).

Example 23

(R)-4-Methyl-6-(3-methylamino-pyrrolidin-1-yl)-pyrimidin-2-ylamine

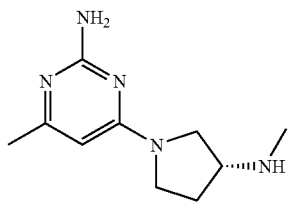

MS (ESI): mass calcd. for $C_{10}H_{17}N_5$, 207.2; m/z found, 208.2 [M+H]$^+$.

Example 24

4-Methyl-6-(cis-octahydro-pyrrolo[3,4-b]pyridin-6-yl)-pyrimidin-2-ylamine

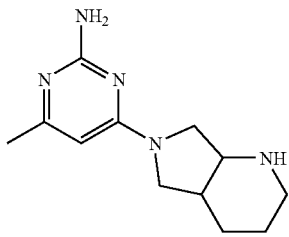

MS (ESI): mass calcd. for $C_{12}H_{19}N_5$, 233.2; m/z found, 234.2 [M+H]$^+$. $^1$H NMR (DMSO-d$_6$): 10.00-9.76 (m, 1H), 9.14-8.93 (m, 1H), 7.90-7.42 (m, 1H), 6.17 (s, 0.3H), 6.13 (s, 0.7H), 3.96-3.87 (m, 1H), 3.87-3.61 (m, 3H), 3.58-3.49 (m, 2H), 3.22-3.11 (m, 1H), 2.94-2.62 (m, 2H), 2.32-2.23 (m, 3H), 1.88-1.62 (m, 4H).

Example 25

4,5-Dimethyl-6-piperazin-1-yl-pyrimidin-2-ylamine

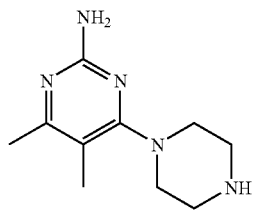

MS (ESI): mass calcd. for $C_{10}H_{17}N_5$, 207.1; m/z found, 208.2 [M+H]$^+$.

Example 26

4,5-Dimethyl-6-(4-methyl-piperazin-1-yl)-pyrimidin-2-ylamine

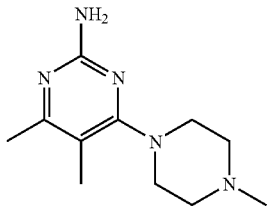

MS (ESI): mass calcd. for $C_{11}H_{19}N_5$, 221.2; m/z found, 222.2 [M+H]$^+$.

Example 27

(R)-4-(3-Amino-pyrrolidin-1-yl)-5,6-dimethyl-pyrimidin-2-ylamine

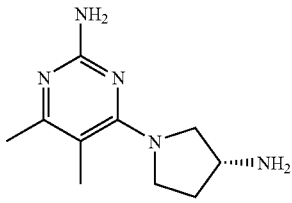

MS (ESI): mass calcd. for $C_{10}H_{17}N_5$, 207.1; m/z found, 208.2 [M+H]$^+$.

Example 28

(R)-4,5-Dimethyl-6-(3-methylamino-pyrrolidin-1-yl)-pyrimidin-2-ylamine

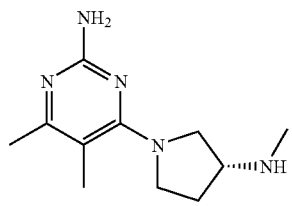

MS (ESI): mass calcd. for $C_{11}H_{19}N_5$, 221.2; m/z found, 222.2 [M+H]$^+$.

Example 29

4-(cis-Hexahydro-pyrrolo[3,4-b]pyrrol-5-yl)-5,6-dimethyl-pyrimidin-2-ylamine

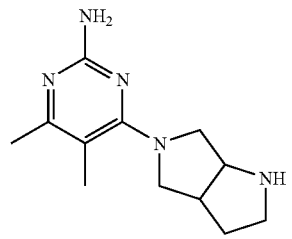

MS (ESI): mass calcd. for $C_{12}H_{19}N_5$, 233.2; m/z found, 234.2 [M+H]$^+$.

Example 30

4,5-Dimethyl-6-(cis-5-methyl-hexahydro-pyrrolo[3,4-c]pyrrol-2-yl)-pyrimidin-2-ylamine

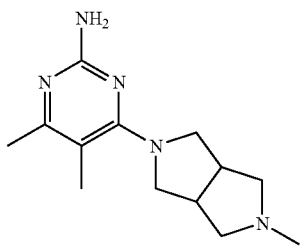

MS (ESI): mass calcd. for $C_{13}H_{21}N_5$, 247.2 m/z found, 248.2 [M+H]$^+$.

Example 31

4,5-Dimethyl-6-(cis-octahydro-pyrrolo[3,4-b]pyridin-6-yl)-pyrimidin-2-ylamine

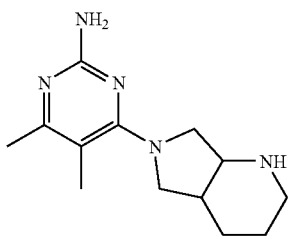

MS (ESI): mass calcd. for $C_{13}H_{21}N_5$, 247.2; m/z found, 248.2 [M+H]$^+$.

Example 32

(S,S)-4-(2,5-Diaza-bicyclo[2.2.1]hept-2-yl)-5,6-dimethyl-pyrimidin-2-ylamine

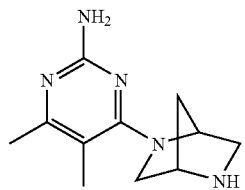

MS (ESI): mass calcd. for $C_{11}H_{17}N_5$, 219.2; m/z found, 220.2 [M+H]$^+$.

Example 33

4-Ethyl-6-piperazin-1-yl-pyrimidin-2-ylamine

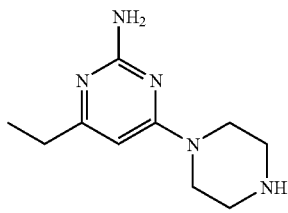

MS (ESI): mass calcd. for $C_{13}H_{21}N_5$, 207.15; m/z found, 208.2 [M+H]$^+$. $^1$H NMR (DMSO-d$_6$): 13.51 (s, 1H), 9.68 (s, 2H), 7.76 (s, 2H), 6.53-6.42 (m, 4H), 3.99 (s, 4H), 3.19 (s, 4H), 2.61-2.53 (m, 2H), 1.28-1.19 (m, 3H).

Example 34

4-Ethyl-6-(4-methyl-piperazin-1-yl)-pyrimidin-2-ylamine

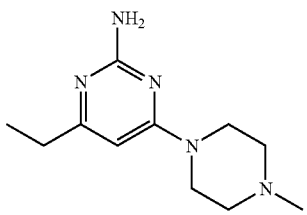

MS (ESI): mass calcd. for $C_{11}H_{19}N_5$, 221.16; m/z found, 222.2 [M+H]$^+$. $^1$H NMR (CDCl$_3$): 5.8 (s, 1H), 5.1 (s, 2H), 3.7-3.5 (m, 5H), 2.5-2.4 (m, 6H), 2.3 (s, 3H), 1.2 (t, J=7.6, 3H).

Example 35

(R)-4-(3-Amino-pyrrolidin-1-yl)-6-ethyl-pyrimidin-2-ylamine

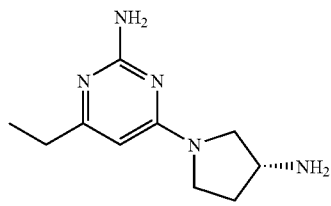

MS (ESI): mass calcd. for $C_{10}H_{17}N_5$, 207.15; m/z found, 208.2 [M+H]$^+$. $^1$H NMR (DMSO-d$_6$): 8.85-8.58 (m, 2H), 8.32-7.18 (m, 1H), 6.17-6.10 (m, 1H), 4.04-3.85 (m, 1H), 3.85-3.53 (m, 4H), 2.66-2.53 (q, J=7.5, 2H), 2.41-2.09 (m, 2H), 1.28-1.19 (t, J=7.5, 3H)

Example 36

(R)-4-Ethyl-6-(3-methylamino-pyrrolidin-1-yl)-pyrimidin-2-ylamine

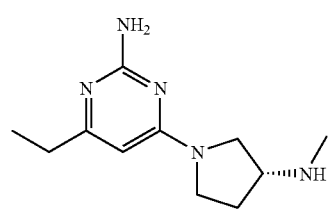

MS (ESI): mass calcd. for $C_{12}H_{20}N_5$, 221.16; m/z found, 222.2 [M+H]$^+$. $^1$H NMR (CDCl$_3$): 5.61 (s, 1H), 5.21 (s, 2H), 3.72-3.12 (m, 5H), 2.55-2.41 (m, 5H), 2.22-2.09 (m, 1H), 1.93-1.77 (m, 1H), 1.27-1.15 (t, J=7.3, 3H)

Example 37

(R,R)-(4-Ethyl-6-hexahydro-pyrrolo[3,4-b]pyrrol-5-yl)-pyrimidin-2-ylamine

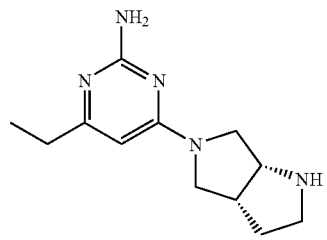

Step A: (R,R)-4-Ethyl-6-[1-(1-phenyl-ethyl)-hexahydro-pyrrolo[3,4-b]pyrrol-5-yl]-pyrimidin-2-ylamine. To a solution of 4-chloro-6-ethyl-pyrimidin-2-ylamine (200 mg, 1.27 mmol) in EtOH (2.4 mL) was added pyridine (210 µL, 2.54 mmol) and 1-(1-phenyl-ethyl)-octahydro-pyrrolo[3,4-b]pyrrole (360 mg, 1.65 mmol). The solution was stirred for 2 h at 90° C. The compound was purified directly with reversed-phase HPLC to yield 115 mg (28%) of the desired compound as a yellow oil.

Step B: (R,R)-(4-Ethyl-6-hexahydro-pyrrolo[3,4-b]pyrrol-5-yl)-pyrimidin-2-ylamine. To a solution of 4-ethyl-6-[1-(1-phenyl-ethyl)-hexahydro-pyrrolo[3,4-b]pyrrol-5-yl]-pyrimidin-2-ylamine (110 mg, 0.33 mmol) in EtOH (1.0 mL) at 23° C. was added palladium hydroxide on carbon (22 mg). The reaction mixture was placed on a Parr hydrogenator and reacted with hydrogen gas at 60 psi for 6 h. The mixture was filtered through diatomaceous earth, rinsing with EtOAc (3×10 mL). The resulting solution was concentrated and purified with reversed-phase HPLC to yield the desired compound as a colorless oil (65 mg, 86%). MS (ESI): mass calcd. for $C_{12}H_{19}N_5$, 233.16; m/z found, 234.2 [M+H]$^+$. $^1$H NMR (CDCl$_3$): 5.61 (s, 1H), 5.22 (s, 2H), 3.99-3.54 (m, 4H), 3.55-3.42 (m, 1H), 3.38-3.23 (m, 1H), 3.16-3.05 (m, 1H), 3.05-2.94 (m, 1H), 2.92-2.80 (m, 1H), 2.53-2.42 (q, J=7.1, 2H), 2.08-1.96 (m, 1H), 1.83-1.67 (m, 1H), 1.28-1.16 (t, J=7.0, 3H).

The compounds in Examples 38-55 were prepared using methods analogous to those described in the preceding examples.

Example 38

4-Ethyl-6-(cis-hexahydro-pyrrolo[3,4-c]pyrrol-2-yl)-pyrimidin-2-ylamine

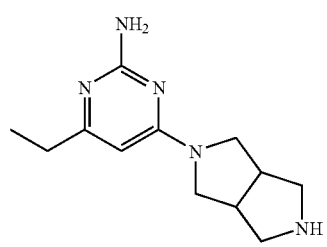

MS (ESI): mass calcd. for $C_{12}H_{19}N_5$, 233.16; m/z found, 234.2 [M+H]$^+$. $^1$H NMR (MeOD): 6.13 (s, 1H), 4.01-3.87 (m, 2H), 3.87-3.78 (m, 1H), 3.77-3.58 (m, 1H), 3.45-3.36 (m, 1H), 3.35-3.24 (m, 3H), 2.66 (q, J=7.5, 2H), 1.32 (t, J=7.5, 3H).

Example 39

(R,R)-(4-Ethyl-6-octahydro-pyrrolo[3,4-b]pyridin-6-yl)-pyrimidin-2-ylamine

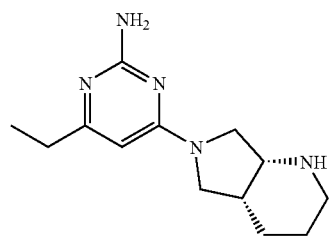

MS (ESI): mass calcd. for $C_{13}H_{21}N_5$, 247.18; m/z found, 248.2 [M+H]$^+$. $^1$H NMR (MeOD): 6.14 (s, 1H), 4.17-3.79 (m, 4H), 3.77-3.60 (m, 1H), 3.45-3.29 (m, 2H), 3.19-3.02 (m, 1H), 3.01-2.80 (m, 1H), 2.77-2.60 (m, 2H), 2.09-1.78 (m, 4H), 1.44-1.24 (m, 3H).

Example 40

4-Cyclopropyl-6-(4-methyl-piperazin-1-yl)-pyrimidin-2-ylamine

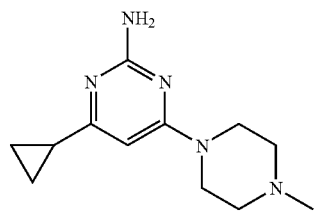

MS (ESI): mass calcd. for $C_{12}H_{19}N_5$, 233.16; m/z found, 234.2 [M+H]$^+$. $^1$H NMR (CDCl$_3$): 5.81 (s, 1H), 4.75 (s, 2H), 3.63-3.54 (t, J=4.9, 4H), 2.46-2.40 (t, J=5.0, 4H), 2.32 (s, 3H), 1.75-1.67 (m, 1H), 1.00-0.94 (m, 2H), 0.89-0.82 (m, 2H).

Example 41

(R)-(4-Cyclopropyl-6-3-methylamino-pyrrolidin-1-yl)-pyrimidin-2-ylamine

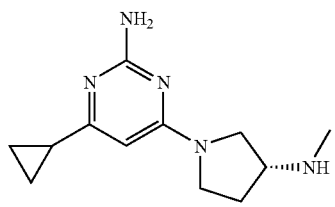

MS (ESI): mass calcd. for C$_{12}$H$_{19}$N$_5$, 233.16; m/z found, 234.2 [M+H]$^+$. $^1$H NMR (CDCl$_3$): 5.58 (s, 1H), 5.30 (s, 1H), 4.73-4.63 (m, 1H), 3.75-3.11 (m, 5H), 2.46 (s, 3H), 2.21-2.10 (m, 1H), 2.04-2.00 (m, 1H), 1.88-1.77 (m, 1H), 1.77-1.67 (m, 1H), 1.00-0.91 (m, 2H), 0.89-0.82 (m, 2H).

Example 42

4-Cyclopropyl-6-(cis-octahydro-pyrrolo[3,4-b]pyridin-6-yl)-pyrimidin-2-ylamine

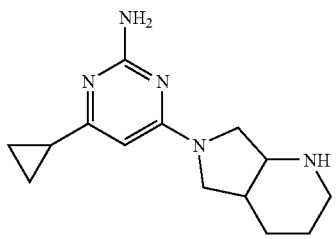

MS (ESI): mass calcd. for C$_{14}$H$_{21}$N$_5$, 259.18; m/z found, 260.2 [M+H]$^+$. $^1$H NMR (DMSO-d$_6$): 12.45 (s, 1H), 9.91-9.74 (m, 1H), 8.96-8.83 (m, 1H), 8.12-7.21 (m, 2H), 6.06 (s, 0.3H), 6.00 (s, 0.7H), 3.96-3.63 (m, 5H), 3.22-3.12 (m, 1H), 2.94-2.82 (m, 1H), 2.80-2.63 (m, 1H), 2.03-1.90 (m, 1H), 1.88-1.60 (m, 4H), 1.19-1.04 (m, 4H).

Example 43

4-Cyclobutyl-6-piperazin-1-yl-pyrimidin-2-ylamine

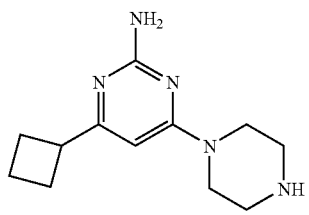

MS (ESI): mass calcd. for C$_{12}$H$_{19}$N$_5$, 233.16; m/z found, 234.2 [M+H]$^+$. $^1$H NMR (DMSO-d$_6$): 12.67 (s, 1H), 9.45 (s, 2H), 8.33-7.25 (m, 1H), 6.43 (s, 1H), 4.16-3.88 (m, 4H), 3.28-3.15 (m, 4H), 2.37-2.19 (m, 4H), 2.10-1.95 (m, 1H), 1.90-1.78 (m, 1H).

Example 44

4-Cyclobutyl-6-(4-methyl-piperazin-1-yl)-pyrimidin-2-ylamine

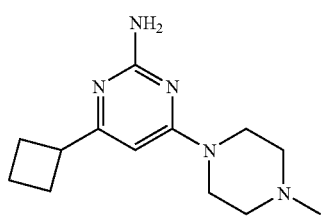

MS (ESI): mass calcd. for C$_{13}$H$_{21}$N$_5$, 247.18; m/z found, 248.2 [M+H]$^+$. $^1$H NMR (CDCl$_3$): 5.82 (s, 1H), 4.81 (s, 2H), 3.60 (t, J=4.9, 4H), 2.44 (t, J=5.0, 4H), 2.32 (s, 3H), 2.28-2.18 (m, 5H), 2.07-1.93 (m, 1H), 1.91-1.78 (m, 1H).

Example 45

(R)-4-(3-Amino-piperidin-1-yl)-6-cyclobutyl-pyrimidin-2-ylamine

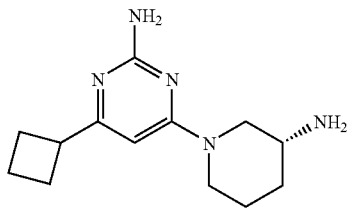

MS (ESI): mass calcd. for C$_{13}$H$_{21}$N$_5$, 247.18; m/z found, 248.2 [M+H]$^+$. $^1$H NMR (CDCl$_3$): 5.84 (s, 1H), 4.91 (s, 2H), 4.32-4.16 (m, 1H), 4.09-3.98 (m, 1H), 3.49-3.43 (m, 1H), 3.40-3.26 (m, 1H), 3.11-2.64 (m, 4H), 2.36-2.15 (m, 4H), 2.12-1.93 (m, 2H), 1.91-1.71 (m, 2H), 1.65-1.48 (m, 1H), 1.44-1.22 (m, 1H).

Example 46

(R)-4-Cyclobutyl-6-(3-methylamino-pyrrolidin-1-yl)-pyrimidin-2-ylamine

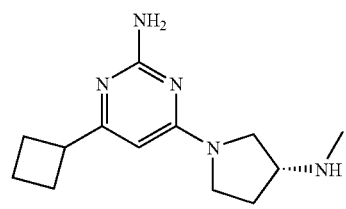

MS (ESI): mass calcd. for C$_{13}$H$_{21}$N$_5$, 247.18; m/z found, 248.2 [M+H]$^+$. $^1$H NMR (CDCl$_3$): 5.62 (s, 1H), 4.71 (s, 2H), 3.75-3.52 (m, 2H), 3.50-3.39 (m, 1H), 3.38-3.20 (m, 3H), 2.52-2.44 (s, 3H), 2.33-2.10 (m, 5H), 2.09-1.76 (m, 5H).

Example 47

4-Cyclobutyl-6-(cis-hexahydro-pyrrolo[3,4-b]pyrrol-5-yl)-pyrimidin-2-ylamine

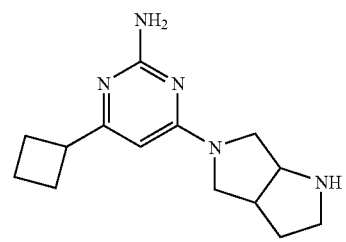

MS (ESI): mass calcd. for C$_{14}$H$_{21}$N$_5$, 259.18; m/z found, 260.2 [M+H]$^+$. $^1$H NMR (CDCl$_3$): 5.63 (s, 1H), 4.71 (s, 2H), 3.94-3.87 (m, 1H), 3.73-3.63 (m, 1H), 3.63-3.56 (m, 1H), 3.53-3.42 (m, 1H), 3.39-3.24 (m, 2H), 3.14-3.05 (m, 1H), 3.02-2.94 (m, 1H), 2.90-2.81 (m, 1H), 2.31-2.16 (m, 4H), 2.08-1.94 (m, 2.5H), 1.89-1.79 (m, 1.5H), 1.77-1.69 (m, 1H).

Example 48

4-Cyclobutyl-6-(cis-hexahydro-pyrrolo[3,4-c]pyrrol-2-yl)-pyrimidin-2-ylamine

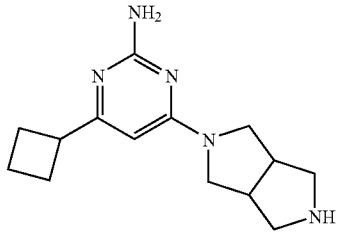

MS (ESI): mass calcd. for $C_{14}H_{21}N_5$, 259.18; m/z found, 260.2 [M+H]$^+$. $^1$H NMR (MeOD): 6.05 (s, 1H), 3.98-3.86 (m, 2H), 3.85-3.78 (m, 1H), 3.77-3.69 (m, 1H), 3.69-3.59 (m, 2H), 3.58-3.48 (m, 1H), 3.43-3.23 (m, 3H), 2.44-2.26 (m, 4H), 2.21-2.07 (m, 1H), 1.99-1.89 (m, 1H).

Example 49

4-Cyclobutyl-6-(cis-5-methyl-hexahydro-pyrrolo[3,4-c]pyrrol-2-yl)-pyrimidin-2-ylamine

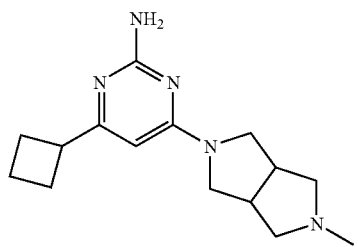

MS (ESI): mass calcd. for $C_{15}H_{23}N_5$, 273.20; m/z found, 274.2 [M+H]$^+$. $^1$H NMR (CDCl$_3$): 5.64 (s, 1H), 4.75 (s, 1H), 3.68-3.57 (m, 2H), 3.44-3.27 (m, 3H), 2.98-2.90 (m, 2H), 2.73-2.66 (m, 2H), 2.47-2.41 (m, 2H), 2.32 (s, 3H), 2.28-2.14 (m, 5H), 2.06-1.94 (m, 2H), 1.89-1.78 (m, 1H), 1.48-1.43 (m, 1H).

Example 50

4-Cyclobutyl-6-(cis-octahydro-pyrrolo[3,4-b]pyridin-6-yl)-pyrimidin-2-ylamine

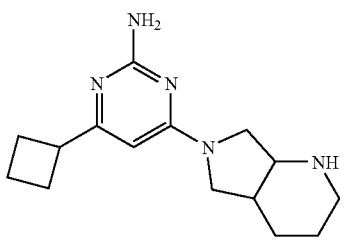

MS (ESI): mass calcd. for $C_{15}H_{23}N_5$, 273.20; m/z found, 274.2 [M+H]$^+$. $^1$H NMR (CDCl$_3$): 5.61 (s, 1H), 4.85 (s, 2H), 3.69-3.17 (m, 6H), 3.06-2.92 (m, 1H), 2.69-2.61 (m, 1H), 2.44-2.12 (m, 5H), 2.08-1.91 (m, 1H), 1.89-1.57 (m, 4H), 1.55-1.43 (m, 1H).

Example 51

(R,R)-(4-Cyclobutyl-6-cis-octahydro-pyrrolo[3,4-b]pyridin-6-yl)-pyrimidin-2-ylamine

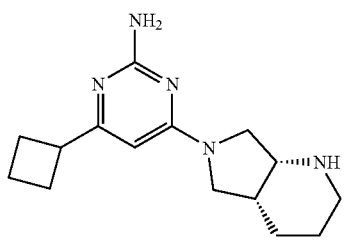

MS (ESI): mass calcd. for $C_{15}H_{23}N_5$, 273.20; m/z found, 274.2 [M+H]$^+$. $^1$H NMR (CDCl$_3$): 5.61 (s, 1H), 4.85 (s, 2H), 3.69-3.17 (m, 6H), 3.06-2.92 (m, 1H), 2.69-2.61 (m, 1H), 2.44-2.12 (m, 5H), 2.08-1.91 (m, 1H), 1.89-1.57 (m, 4H), 1.55-1.43 (m, 1H).

Example 52

4-Cyclohexyl-6-(4-methyl-piperazin-1-yl)-pyrimidin-2-ylamine

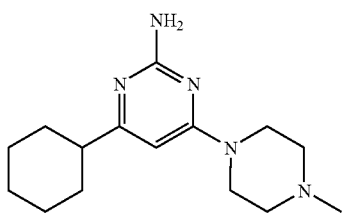

MS (ESI): mass calcd. for $C_{15}H_{25}N_5$, 275.21; m/z found, 276.2 [M+H]$^+$. $^1$H NMR (CDCl$_3$): 5.80 (s, 1H), 4.71 (s, 2H), 3.59 (t, J=5.1, 4H), 2.44 (t, J=5.1, 4H), 2.32 (s, 3H), 1.93-1.86 (m, 2H), 1.85-1.77 (m, 2H), 1.76-1.68 (m, 1H), 1.47-1.18 (m, 6H).

Example 53

(R)-(4-Cyclohexyl-6-3-methylamino-pyrrolidin-1-yl)-pyrimidin-2-ylamine

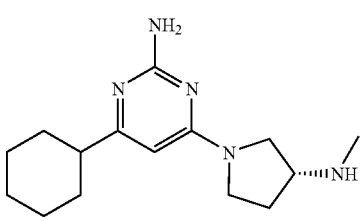

MS (ESI): mass calcd. for $C_{15}H_{25}N_5$, 275.21; m/z found, 276.2 [M+H]$^+$. $^1$H NMR (CDCl$_3$): 5.59 (s, 1H), 5.30 (s, 2H), 4.69 (s, 2H), 3.71-3.51 (m, 2H), 3.46-3.38 (m, 1H), 3.37-3.29 (m, 1H), 2.47 (s, 3H), 2.36-2.26 (m, 1H), 2.22-2.12 (m, 1.5H), 1.95-1.77 (m, 5.5H), 1.76-1.68 (m, 1H), 1.47-1.17 (m, 6H).

Example 54

4-Cyclohexyl-6-(cis-hexahydro-pyrrolo[3,4-b]pyrrol-5-yl)-pyrimidin-2-ylamine

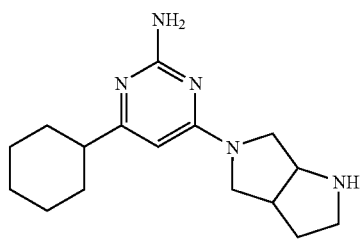

MS (ESI): mass calcd. for $C_{16}H_{25}N_5$, 287.21; m/z found, 288.2 [M+H]+. $^1$H NMR (CDCl$_3$): 5.59 (s, 1H), 4.89 (s, 2H), 4.02-3.81 (m, 1H), 3.73-3.63 (m, 1H), 3.62-3.53 (m, 1H), 3.52-3.47 (m, 1H), 3.35-3.22 (m, 1H), 3.21-2.94 (m, 2H), 2.91-2.78 (m, 1H), 2.76-2.40 (m, 2H), 2.38-2.27 (m, 1H), 2.12-1.96 (m, 1H), 1.94-1.86 (m, 2H), 1.85-1.77 (m, 2H), 1.76-1.67 (m, 2H), 1.48-1.17 (m, 5H).

Example 55

(R,R)-4-Cyclohexyl-6-(octahydro-pyrrolo[3,4-b]pyridin-6-yl)-pyrimidin-2-ylamine

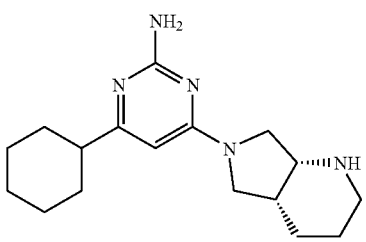

MS (ESI): mass calcd. for $C_{17}H_{27}N_5$, 301.23; m/z found, 302.2 [M+H]+. $^1$H NMR (CDCl$_3$): 5.59 (s, 1H), 4.84 (s, 2H), 3.72-3.27 (m, 6H), 3.05-2.94 (m, 1H), 2.72-2.60 (m, 1H), 2.47-2.23 (m, 2H), 2.01-1.86 (m, 2H), 1.85-1.55 (m, 6H), 1.55-1.19 (m, 6H).

Example 56

4-Piperazin-1-yl-6-(tetrahydro-furan-3-yl)-pyrimidin-2-ylamine

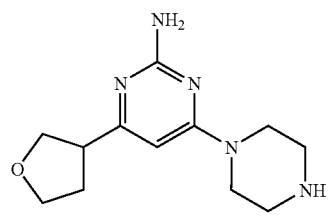

Step A: 2-Amino-6-(tetrahydro-furan-3-yl)-3H-pyrimidin-4-one. To a solution of 3-oxo-3-(tetrahydro-furan-3-yl)-propionic acid ethyl ester (4.0 g, 21.5 mmol) and guanidine hydrochloride (2.6 g, 27.2 mmol) in MeOH (125 mL) at 23° C. was added potassium tert-butoxide in portions (3.4 g, 30.3 mmol) over 5 min. The reaction was heated at 80° C. for 18 h. The mixture was filtered while warm to remove insoluble salts, and the filtrate was concentrated to afford an oil which was diluted with water (~25 mL) and extracted with EtOAc (8×50 mL). The combined organic layers were washed with satd. aq. NaCl, dried, and concentrated to give a residue. The aqueous portion was concentrated to afford a solid residue that was collected and rinsed with MeOH. The residue and solid materials were combined and chromatographed (2 M NH$_3$ in MeOH/EtOAc) to provide 2.02 g of product as a white solid (51%). MS (ESI): mass calcd. for: $C_8H_{11}N_3O_2$, 181.1; m/z found, 182.2 [M+H]+. $^1$H NMR (CD$_3$OD): 5.66 (br s, 1H), 3.93-4.01 (m, 2H), 3.75-3.85 (m, 2H), 3.28-3.31 (m, 2H), 3.16-3.24 (m, 1H), 2.18-2.27 (m, 1H), 2.05-2.15 (m, 1H).

Step B: 4-Chloro-6-(tetrahydro-furan-3-yl)-pyrimidin-2-ylamine. A suspension of 2-amino-6-(tetrahydro-furan-3-yl)-3H-pyrimidin-4-one (1.5 g, 8.28 mmol), tetraethyl ammonium chloride (2.7 g 16.3 mmol) and dimethylaniline (1.4 mL, 11.1 mmol) in acetonitrile (15 mL) was treated with phosphorous oxychloride (2.4 mL, 26.2 mmol) and heated at 110° C. for 20 min. The resulting solution was cooled to rt and concentrated to minimum volume and pipetted onto ice chips. The aqueous portion was extracted with EtOAc (3×50 mL). The combined organic layers were basified with satd. aq. NaHCO$_3$ solution to pH~7. The organic portion was separated, dried, and concentrated. The crude material was chromatographed (MeOH/CH$_2$Cl$_2$) to yield 680 mg (42%) of product as a light orange foam. $^1$H NMR (CDCl$_3$): 6.59 (s, 1H), 5.16 (br s, 2H), 4.00-4.10 (m, 2H), 3.85-3.91 (m, 2H), 3.28-3.35 (m, 1H), 2.25-2.34 (m, 1H), 2.08-2.18 (m, 1H).

Step C: 4-[2-Amino-6-(tetrahydro-furan-3-yl)-pyrimidin-4-yl]-piperazine-1-carboxylic acid tert-butyl ester. A solution of 4-chloro-6-(tetrahydro-furan-3-yl)-pyrimidin-2-ylamine (500 mg, 2.51 mmol), N-BOC piperazine (960 mg, 5.15 mmol) and pyridine (500 uL, 6.1 mmol) in EtOH (10 mL) was heated at 90° C. for 4 h. Upon cooling to rt a thick precipitate formed which was collected by filtration. The material was rinsed with EtOAc to afford 125 mg of a white solid. The filtrate was concentrated and triturated with Et$_2$O-EtOAc (1:1) to yield an additional 600 mg of material (82% combined). MS (ESI): mass calcd. for $C_{17}H_{27}N_5O_3$, 349.2; m/z found, 350.3 [M+H]+. $^1$H NMR (CDCl$_3$): 5.86 (s, 1H), 4.70 (br s, 2H), 3.90-4.07 (m, 2H), 3.83-3.90 (m, 2H), 3.55-3.60 (m, 4H), 3.45-3.50 (m, 4H), 3.18-3.26 (m, 1H), 2.20-2.30 (m, 1H), 2.09-2.18 (m, 1H), 1.48 (s, 9H).

Step D: 4-Piperazin-1-yl-6-(tetrahydro-furan-3-yl)-pyrimidin-2-ylamine. A solution of 4-[2-amino-6-(tetrahydro-furan-3-yl)-pyrimidin-4-yl]-piperazine-1-carboxylic acid tert-butyl ester (600 mg, 1.72 mmol) in formic acid (10 mL) was treated with 6.0 N HCl (2 mL) and stirred for 2 h at rt. The mixture was diluted with MeOH (10 mL) and concentrated. This process was repeated twice, yielding 295 mg of a white solid as the hydrochloride salt. The crude material was chromatographed (2 M NH$_3$ in MeOH/CH$_2$Cl$_2$) to afford 133 mg (50%) of the free base as an off-white solid. MS (ESI): mass calcd. for $C_{12}H_{19}N_5O$, 249.1; m/z found, 250.2 [M+H]+. $^1$H NMR (CDCl$_3$): 6.86 (s, 1H), 4.78 (br s, 2H), 3.98-4.07 (m, 2H), 3.83-3.90 (m, 2H), 3.54-3.58 (m, 4H), 3.22 (p, J=15.0, 7.3, 1H), 2.89-2.93 (m, 4H), 2.10-2.30 (m, 4H).

The compounds in Examples 57-65 were prepared using methods analogous to those described in the preceding examples.

Example 57

4-(4-Methyl-piperazin-1-yl)-6-(tetrahydro-furan-3-yl)-pyrimidin-2-ylamine

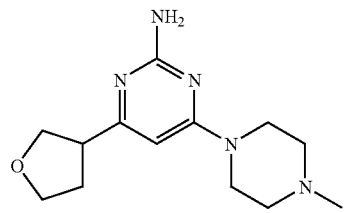

MS (ESI): mass calcd. for $C_{13}H_{21}N_5O$, 263.1; m/z found, 264.2 [M+H]$^+$. $^1$H NMR (CDCl$_3$): 5.87 (s, 1H), 4.84 (br s, 2H), 3.98-4.06 (m, 2H), 3.83-3.89 (m, 2H), 3.58-3.61 (m, 4H), 3.17-3.25 (m, 1H), 2.42-2.46 (m, 4H), 2.32 (s, 3H), 2.20-2.29 (m, 1H), 2.08-2.18 (m, 1H).

Example 58

4-Piperazin-1-yl-6-(tetrahydro-pyran-4-yl)-pyrimidin-2-ylamine

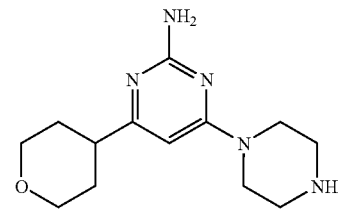

MS (ESI): mass calcd. for $C_{13}H_{21}N_5O$, 263.17; m/z found, 264.2 [M+H]$^+$. $^1$H NMR (CDCl$_3$): 5.80 (s, 1H), 5.16 (br s, 2H), 4.03-4.08 (m, 2H), 3.56-3.60 (m, 4H), 3.50 (dt, J=11.4, 3.0, 2H), 2.90-2.94 (m, 4H), 2.58-2.67 (m, 1H), 1.73-1.85 (m, 4H).

Example 59

4-(4-Methyl-piperazin-1-yl)-6-(tetrahydro-pyran-4-yl)-pyrimidin-2-ylamine

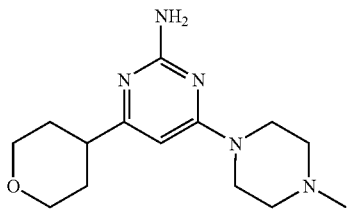

MS (ESI): mass calcd. for $C_{14}H_{23}N_5O$, 277.19; m/z found, 278.2 [M+H]$^+$. $^1$H NMR (CDCl$_3$): 5.81 (s, 1H), 4.74 (br s, 2H), 4.05 (dt, J=11.2, 3.2, 2H), 3.59-3.62 (m, 4H), 3.45-3.52 (m, 2H), 2.54-2.62 (m, 1H), 2.43-2.46 (m, 4H), 2.33 (s, 3H), 1.76-1.82 (m, 4H).

Example 60

(R)-4-(3-Methylamino-pyrrolidin-1-yl)-6-(tetrahydro-pyran-4-yl)-pyrimidin-2-ylamine

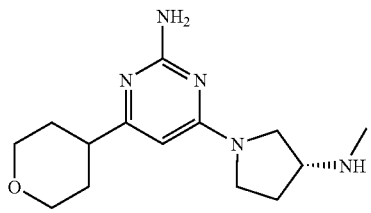

MS (ESI): mass calcd. for $C_{14}H_{23}N_5O$, 277.19; m/z found, 278.2 [M+H]$^+$. $^1$H NMR (CDCl$_3$): 5.60 (s, 1H), 4.72 (br s, 2H), 4.03-4.08 (m, 2H), 3.30-3.70 (m, 7H), 2.53-2.61 (m, 1H), 2.48 (s, 3H), 2.11-2.20 (m, 1H), 1.73-1.86 (m, 5H).

Example 61

(R,R)-4-(Octahydro-pyrrolo[3,4-b]pyridin-6-yl)-6-(tetrahydro-pyran-4-yl)-pyrimidin-2-ylamine

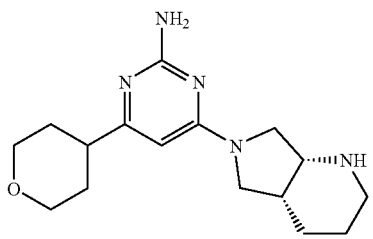

MS (ESI): mass calcd. for $C_{16}H_{25}N_5O$, 303.21; m/z found, 304.2 [M+H]$^+$. $^1$H NMR (CDCl$_3$): 5.60 (br s, 1H), 5.1-5.5 (br s, 2H), 4.02-4.08 (m, 2H), 3.02-3.57 (m, 6H), 2.96-3.04 (m, 1H), 2.58-2.70 (m, 2H), 2.22-2.42 (m, 1H), 1.48-1.88 (m, 8H).

Example 62

4-Benzyl-6-piperazin-1-yl-pyrimidin-2-ylamine

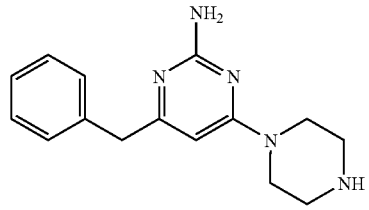

MS (ESI): mass calcd. for $C_{15}H_{19}N_5$, 269.35; m/z found, 270.2 [M+H]$^+$. $^1$H NMR (CDCl$_3$): 7.22-7.35 (m, 5H), 5.68-

5.75 (br s, 2H), 5.66 (s, 1H), 3.9-4.10 (br s, 1H), 3.84 (s, 2H), 3.48-3.54 (m, 4H), 2.85-2.90 (m, 4H).

Example 63

4-Benzyl-6-(4-methyl-piperazin-1-yl)-pyrimidin-2-ylamine

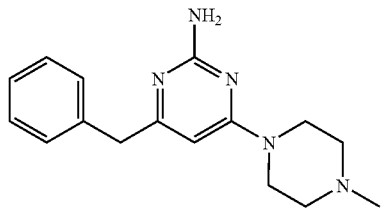

MS (ESI): mass calcd. for $C_{16}H_{21}N_5$, 283.37; m/z found, 284.2 [M+H]$^+$. $^1$H NMR (CDCl$_3$): 7.20-7.32 (m, 5H), 5.73 (s, 1H), 4.75 (br s, 2H), 3.78 (s, 2H), 3.5-3.55 (m, 4H), 2.38-2.45 (m, 4H), 2.32 (s, 3H).

Example 64

(R)-Benzyl-6-(3-methylamino-pyrrolidin-1-yl)-pyrimidin-2-ylamine

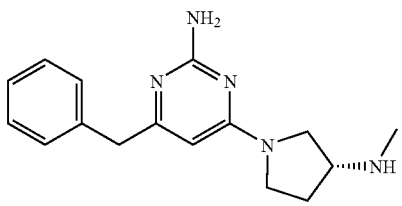

MS (ESI): mass calcd. for $C_{16}H_{21}N_5$, 283.37; m/z found, 284.2 [M+H]$^+$. $^1$H NMR (CDCl$_3$): 7.18-7.32 (m, 5H), 5.50 (s, 1H), 4.83-4.85 (br s, 2H), 3.78 (s, 3H), 3.2-3.7 (m, 4H), 2.44 (s, 3H), 2.05-2.15 (m, 1H), 1.74-1.84 (m, 1H).

Example 65

(R,R)-4-Benzyl-6-(octahydro-pyrrolo[3,4-b]pyridin-6-yl)-pyrimidin-2-ylamine

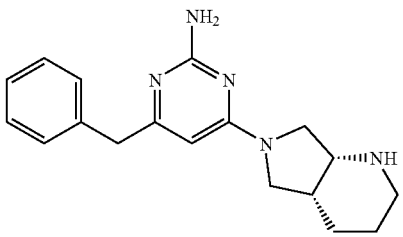

MS (ESI): mass calcd. for $C_{18}H_{23}N_5$, 309.41; m/z found, 310.2 [M+H]$^+$. $^1$H NMR (DMSO-d$_6$): 12.90-12.95 (br s, 1H), 10.10-10.22 (m, 1H), 9.0-9.10 (m, 1H), 7.25-7.45 (m, 5H), 6.24 (s, 1H), 3.65-3.95 (br m, 6H), 3.48-3.58 (m, 1H), 3.12-3.16 (m, 1H), 2.60-2.90 (m, 2H), 1.60-1.80 (m, 4H).

Example 66

4-(4-Methyl-piperazin-1-yl)-5,6,7,8-tetrahydro-quinazolin-2-ylamine

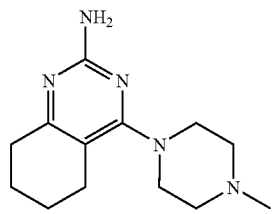

Steps A: 4-Chloro-5,6,7,8-tetrahydro-quinazolin-2-ylamine. The title compound was prepared from 3-cyclohexyl-3-oxo-propionic acid ethyl ester, using methods analogous to those described in Example 1, Steps A-B.

Step B: 4-(4-Methyl-piperazin-1-yl)-5,6,7,8-tetrahydro-quinazolin-2-ylamine. A solution of 4-chloro-5,6,7,8-tetrahydro-quinazolin-2-ylamine (100 mg, 0.55 mmol), N-methyl piperazine (91 uL, 1.5 mmol) and Et$_3$N (140 uL, 1.1 mmol) in EtOH (2 ml) was heated at 70° C. for 16 h. The mixture was cooled to rt and concentrated, and the crude residue was purified (2 M NH$_3$ in MeOH/CH$_2$Cl$_2$) to yield a white solid (31 mg, 23%). MS (ESI): mass calcd. for $C_{13}H_{21}N_5$, 247.3; m/z found, 248.2 [M+H]$^+$. $^1$H NMR (MeOD): 3.30-3.23 (m, 4H), 3.21 (dt, J=3.3, 1.6, 1H), 2.49 (t, J=6.7, 2H), 2.47-2.41 (m, 4H), 2.36 (t, J=5.9, 2H), 2.23 (s, 3H), 1.77-1.67 (m, 2H), 1.62-1.52 (m, 2H).

The compounds in Examples 67-75 were prepared using methods analogous to those described in Example 66.

Example 67

4-(4-Piperazin-1-yl)-5,6,7,8-tetrahydro-quinazolin-2-ylamine

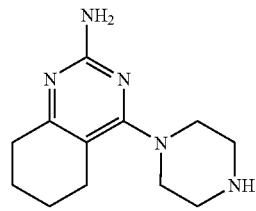

MS (ESI): mass calcd. for $C_{12}H_{19}N_5$, 233.2; m/z found, 234.2 [M+H]$^+$. $^1$H NMR (MeOD): 3.28-3.20 (m, 4H), 2.85 (t, J=4.8, 4H), 2.53 (t, J=6.6, 2H), 2.39 (t, J=5.9, 2H), 1.80-1.71 (m, 2H), 1.65-1.56 (m, 2H).

Example 68

(R)-4-(3-Amino-pyrrolidin-1-yl)-5,6,7,8-tetrahydro-quinazolin-2-ylamine

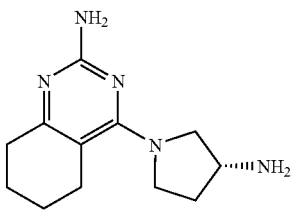

MS (ESI): mass calcd. for $C_{12}H_{19}N_5$, 233.2; m/z found, 234.2 [M+H]$^+$.

Example 69

(R)-4-(3-Methylamino-pyrrolidin-1-yl)-5,6,7,8-tetrahydro-quinazolin-2-ylamine

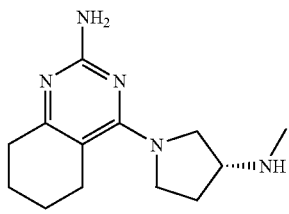

MS (ESI): mass calcd. for $C_{13}H_{21}N_5$, 248.4; m/z found, 248.2 [M+H]$^+$. $^1$H NMR (MeOD): 3.67-3.55 (m, 2H), 3.53-3.45 (m, 1H), 3.28 (dd, J=11.0, 5.5, 1H), 3.06 (p, J=6.0, 1H), 2.58-2.45 (m, 2H), 2.38 (t, J=6.4, 2H), 2.24 (s, 3H) 2.01-1.90 (m, 1H), 1.68-1.45 (m, 5H).

Example 70

(R,R)-4-(Hexahydro-pyrrolo[3,4-b]pyrrol-5-yl)-5,6,7,8-tetrahydro-quinazolin-2-ylamine

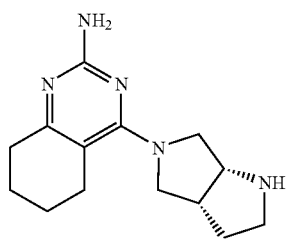

MS (ESI): mass calcd. for $C_{14}H_{21}N_5$, 259.2; m/z found, 260.2 [M+H]$^+$.

Example 71

4-(cis-Octahydro-pyrrolo[3,4-b]pyridin-6-yl)-5,6,7,8-tetrahydro-quinazolin-2-ylamine

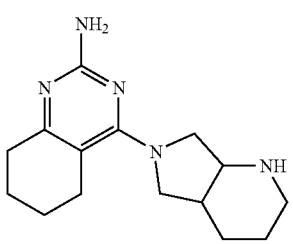

MS (ESI): mass calcd. for $C_{15}H_{23}N_5$, 273.4; m/z found, 274.3 [M+H]$^+$. $^1$H NMR (MeOD): 3.87-3.74 (m, 2H), 3.66-3.59 (m, 1H), 3.54 (dd, J=11.7, 1.6, 1H), 3.32-3.28 (m, 1H), 2.96 (dt, J=12.2, 3.6, 1H), 2.78-2.68 (m, 2H), 2.67-2.58 (m, 1H), 2.58-2.50 (m, 2H), 2.34-2.24 (m, 1H), 1.92-1.80 (m, 2H), 1.80-1.73 (m, 2H), 1.73-1.60 (m, 2H), 1.60-1.44 (m, 2H).

Example 72

(R,R)-4-(Octahydro-pyrrolo[3,4-b]pyridin-6-yl)-5,6,7,8-tetrahydro-quinazolin-2-ylamine

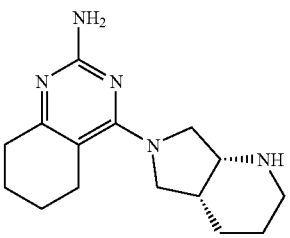

MS (ESI): mass calcd. for $C_{15}H_{23}N_5$, 273.4; m/z found, 274.3 [M+H]$^+$. $^1$H NMR (MeOD): 3.87-3.74 (m, 2H), 3.66-3.59 (m, 1H), 3.54 (dd, J=11.7, 1.6, 1H), 3.32-3.28 (m, 1H), 2.96 (dt, J=12.2, 3.6, 1H), 2.78-2.68 (m, 2H), 2.67-2.58 (m, 1H), 2.58-2.50 (m, 2H), 2.34-2.24 (m, 1H), 1.92-1.80 (m, 2H), 1.80-1.73 (m, 2H), 1.73-1.60 (m, 2H), 1.60-1.44 (m, 2H).

Example 73

(S,S)-4-(2,5-Diaza-bicyclo[2.2.1]hept-2-yl)-5,6,7,8-tetrahydro-quinazolin-2-ylamine

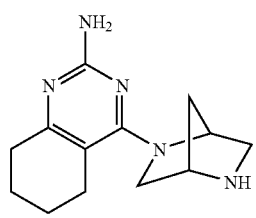

MS (ESI): mass calcd. for $C_{13}H_{19}N_5$, 245.2; m/z found, 246.2 [M+H]$^+$.

Example 74

4-(4-Methyl-piperazin-1-yl)-6,7-dihydro-5H-cyclopentapyrimidin-2-ylamine

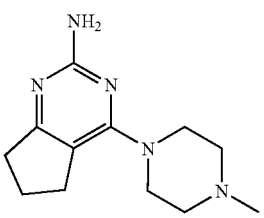

MS (ESI): mass calcd. for $C_{12}H_1N_5$, 233.16; m/z found, 234.2 [M+H]$^+$. $^1$H NMR (CDCl$_3$): 4.75 (s, 2H), 3.68 (t, J=9.8, 4.8, 4H), 2.91-2.85 (t, J=14.4, 7.0, 2H), 2.73-2.66 (t, J=15.6, 7.7, 2H), 2.47-2.42 (t, J=10.0, 5.0, 4H), 2.31 (s, 3H), 2.03-1.94 (qt, J=15.5, 7.9, 2H).

Example 75

(R)-4-(3-Methylamino-pyrrolidin-1-yl)-6,7-dihydro-5H-cyclopentapyrimidin-2-ylamine

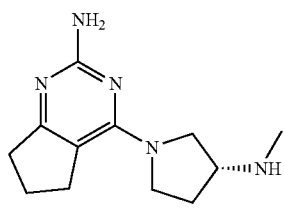

MS (ESI): mass calcd. for $C_{12}H_{19}N_5$, 233.16; m/z found, 234.2 [M+H]$^+$. $^1$H NMR (CDCl$_3$): 4.88 (s, 2H), 3.84-3.74 (m, 2.7H), 3.72-3.61 (m, 1.3H), 3.49-3.41 (m, 2H), 3.27-3.20 (m, 1H), 3.08-2.92 (m, 2H), 2.82-2.61 (m, 2H), 2.46 (s, 3H), 2.14-2.04 (m, 1H), 2.02-1.90 (m, 2H), 1.83-1.74 (m, 2H).

The compounds in Examples 76-79 were prepared using methods analogous to those described in the preceding examples.

Example 76

4-tert-Butyl-6-piperazin-1-yl-pyrimidin-2-ylamine

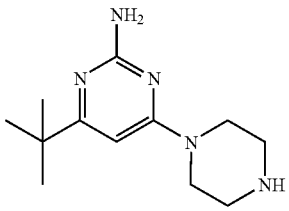

MS (ESI): mass calcd. for $C_{12}H_{21}N_5$, 235.18; m/z found, 236.2 [M+H]$^+$.

Example 77

4-tert-Butyl-6-(4-methyl-piperazin-1-yl)-pyrimidin-2-ylamine

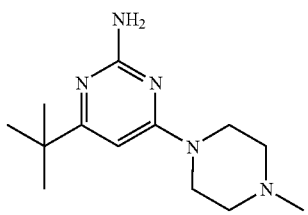

MS (ESI): mass calcd. for $C_{13}H_{23}N_5$, 249.20; m/z found, 250.3 [M+H]$^+$.

Example 78

(R)-4-tert-Butyl-6-(3-methylamino-pyrrolidin-1-yl)-pyrimidin-2-ylamine

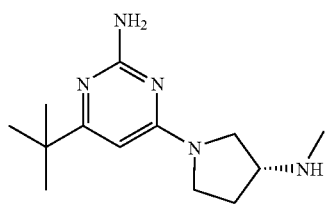

MS (ESI): mass calcd. for $C_{13}H_{23}N_5$, 249.20; m/z found, 250.3 [M+H]$^+$.

Example 79

(R,R)-4-tert-Butyl-6-(octahydro-pyrrolo[3,4-b]pyridin-6-yl)-pyrimidin-2-ylamine

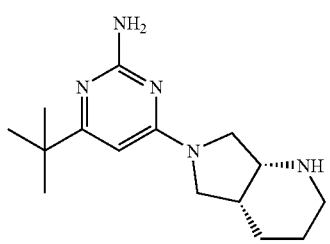

MS (ESI): mass calcd. for $C_{15}H_{25}N_5$, 275.21; m/z found, 276.3 [M+H]$^+$.

Intermediate 1

3-(4-Methyl-tetrahydro-pyran-4-yl)-3-oxo-propionic acid ethyl ester

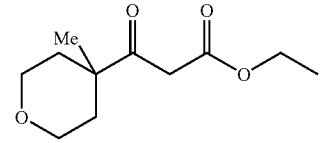

Step A: (4-Methyl-tetrahydro-pyran-4-yl)-methanol. A −78° C. solution of 4-methyl-tetrahydro-pyran-4-carboxylic acid methyl ester (Regan, J. et al. *J. Med. Chem.* 2002, 45, 2994-3008; 9.9 g, 63 mmol) in CH$_2$Cl$_2$ (400 mL) was treated with DIBAL-H (1.0 M in CH$_2$Cl$_2$; 125 mL, 125 mmol). The resulting mixture was stirred for 1 h, and then was diluted with EtOAc (200 mL) and satd. aq. NH$_4$Cl. The mixture was treated with satd. aq. sodium potassium tartrate, allowed to warm to rt, and stirred for 45 min. The mixture was extracted with CH$_2$Cl$_2$ (4×), and the combined extracts were washed with satd. aq. NaCl, dried, and concentrated. Chromatography (EtOAc/hexanes) afforded the title compound as a colorless oil (5.6 g 69%). The spectral data matched that reported in PCT Intl. Pat. Appl. Publ. No. WO 2006/001752.

Step B: 4-Methyl-tetrahydro-pyran-4-carboxaldehyde. To a solution of (4-methyl-tetrahydro-pyran-4-yl)-methanol (1.5 g, 11.5 mmol) in $CH_2Cl_2$ was added a suspension of Dess-Martin periodinane (5.8 g, 14 mmol) in $CH_2Cl_2$ (30 mL). After 70 min, the heterogenous mixture was diluted with $Et_2O$ (100 mL), stirred for 10 min, treated with 1 N HaOH (10 mL), and stirred for another 10 min. The mixture was filtered, and the filtrate was concentrated. The residue was purified by chromatography ($Et_2O/CH_2Cl_2$) to give the title compound (1.01 g, 68%) as a colorless volatile oil. The spectral data matched that reported in PCT Intl. Pat. Appl. Publ. No. WO 2006/001752.

Step C: 3-(4-Methyl-tetrahydro-pyran-4-yl)-3-oxo-propionic acid ethyl ester. To a solution of $BF_3.OEt_2$ (0.350 mL, 2.50 mmol) and ethyl diazoacetate (0.390 mL, 3.42 mmol) was added a solution of 4-methyl-tetrahydro-pyran-4-carboxaldehyde (350 mg, 2.73 mmol) in $CH_2Cl_2$ (15 mL). After 20 min, the mixture was poured into half-saturated aq. NaCl and extracted with $CH_2Cl_2$. The combined organic layers were dried and concentrated. Chromatography (EtOAc/hexanes) afforded the title compound (461 mg, 79%) as a colorless oil. MS (ESI): mass calcd. for $C_{11}H_{18}O_4$, 214.1; m/z found, 215.2 $[M+H]^+$. $^1H$ NMR (mixture of tautomers; $CDCl_3$): 12.5 (s, 0.5H), 5.05 (s, 0.5H), 4.25-4.17 (m, 2H), 3.76-3.53 (m, 2H), 5.52 (s, 3H), 2.05-1.92 (m, 2H), 1.56-1.47 (m, 2H), 1.26-1.22 (m, 3H), 1.38-1.34 (m, 3H).

Intermediate 2

3-Cyclopentyl-2-methoxy-3-oxo-propionic acid methyl ester

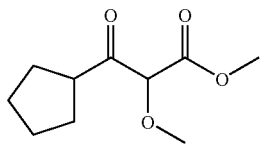

The title compound was prepared using a method analogous to that described in Tetrahedron 1998, 44, 1603-1607: To a suspension of iodosobenzene diacetate (5.2 g, 16.3 mmol) in MeOH (40 mL) was added $BF_3.OEt_2$ (2.1 mL, 16.3 mmol). The resulting mixture was added to 3-cyclopentyl-3-oxo-propionic acid ethyl ester (3.0 g, 16.3 mmol) and stirred at rt overnight. The mixture was concentrated to half the total volume, quenched with satd. aq. $NaHCO_3$, and extracted with $CHCl_3$ (2×). The combined organic layers were dried and concentrated and the crude residue purified (EtOAc/hexanes) to yield a colorless oil (1.5 g, 43%). $^1H$ NMR (MeOD): 4.4 (s, 1H), 3.8 (s, 3H), 3.5 (s, 3H), 3.3-3.2 (m, 1H), 1.9-1.5 (m, 8H).

Intermediate 3

3-Oxo-4-pyridin-4-yl-butyric acid ethyl ester

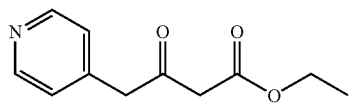

A solution of pyridin-4-yl-acetic acid hydrochloride salt (1.73 g 10 mmol) in $CH_2Cl_2$ (50 mL) was treated with tri-ethylamine (2.09 mL, 15 mmol), followed by 1,1'-carbonyldiimidazole (2.43 g, 15 mol). After 4 h, the solution was added dropwise to a 0° C. solution of 2,2-dimethyl-[1,3]dioxane-4,6-dione (Meldrum's acid; 1.73 g, 12 mmol) and pyridine (1.63 mL, 20 mmol) in $CH_2Cl_2$ (50 mL). The reaction mixture was allowed to warm slowly to rt and was stirred for 18 h. The mixture was washed with $H_2O$ (2×), and the organic layer was dried and concentrated. The crude residue was dissolved in EtOH (100 mL) and heated at reflux for 4 h. The mixture was allowed to cool to rt and was concentrated. The residue was purified by chromatography (EtOAc/hexanes) to give the title compound (411 mg, 15%) as a pale yellow oil. MS (ESI): mass calcd. for $C_{11}H_{13}NO_3$, 207.1; m/z found, 208.1 $[M+H]^+$. $^1H$ NMR ($CDCl_3$): 8.57 (dd, J=4.4, 1.6, 2H), 7.16 (dd, J=4.4, 1.6, 2H), 4.20 (q, J=7.2, 2H), 3.88 (s, 2H), 3.51 (s, 2H), 1.28 (t, J=7.2, 3H).

Intermediate 4

3-Oxo-3-(tetrahydro-furan-3-yl)-propionic acid ethyl ester

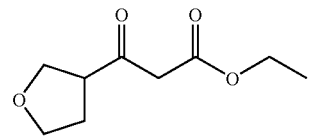

To a solution of lithium bis(trimethylsilyl)amide (1 M in hexanes; 100 mL) in THF (200 mL) at −78° C. was added dry ethyl acetate (10.8 g, 12 mL, 122.5 mmol) dropwise. After 30 min at −78° C., the mixture was treated with a solution of tetrahydro-furan-3-carboxylic acid methyl ester (6.0 g, 46.1 mmol) in THF (50 mL). After 4 h at −78° C., the reaction was quenched with satd. aq. $NH_4Cl$, warmed to rt, and extracted with EtOAc (5×75 mL). The combined organic layers were washed with satd. aq. NaCl, dried, and concentrated to give a colorless oil. Chromatography on $SiO_2$ (EtOAc/$CH_2Cl_2$) afforded the title compound (3.3 g).

The compounds in Examples 80-255 were prepared from the appropriate beta-ketoesters according to methods described in the preceding examples. The beta-ketoesters or 1,3-diones used were commercially available or prepared using methods described for Intermediates 1-4.

Example 80

(R)-4-(3-Amino-pyrrolidin-1-yl)-6-cyclopentyl-pyrimidin-2-ylamine

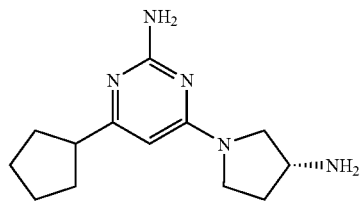

MS (ESI): mass calcd. for $C_{13}H_{21}N_5$, 247.2; m/z found, 248.2 $[M+H]^+$. $^1H$ NMR (MeOD): 5.72 (s, 1H), 3.85-3.54 (m, 3H), 3.54-3.32 (m, 1H), 3.32-3.15 (m, 1H), 2.92-2.71 (m, 1H), 2.24 (ddd, J=12.8, 12.7, 6.4, 1H), 2.03-1.94 (m, 2H), 1.95-1.75 (m, 3H), 1.74-1.63 (m, 4H).

Example 81

(R,R)-4-Cyclopentyl-6-(octahydro-pyrrolo[3,4-b]pyridin-6-yl)-pyrimidin-2-ylamine

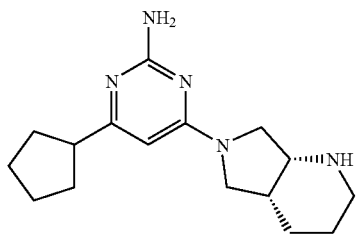

MS (ESI): mass calcd. for $C_{16}H_{25}N_5$, 287.2; m/z found, 288.3 [M+H]$^+$. $^1$H NMR (MeOD): 5.77-5.68 (m, 1H), 3.65-3.25 (m, 5H), 2.91 (td, J=12.3, 3.8, 1H), 2.86-2.74 (m, 1H), 2.66-2.55 (m, 1H), 2.47-2.25 (m, 1H), 2.05-1.89 (m, 2H), 1.88-1.73 (m, 4H), 1.75-1.58 (m, 4H), 1.54-1.44 (m, 1H).

Example 82

4-Cyclopentyl-6-(cis-5-methyl-hexahydro-pyrrolo[3,4-c]pyrrol-2-yl)-pyrimidin-2-ylamine

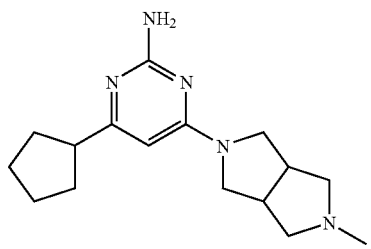

MS (ESI): mass calcd. for $C_{16}H_{25}N_5$, 287.2; m/z found, 288.3 [M+H]$^+$. $^1$H NMR (CDCl$_3$): 5.77 (s, 1H), 3.64-3.56 (m, 2H), 3.46-3.37 (m, 3H), 3.04-2.95 (m, 2H), 2.85-2.75 (m, 2H), 2.44 (dd, J=9.8, 4.1, 2H), 2.32 (s, 3H), 2.03-1.92 (m, 2H), 1.84-1.75 (m, 2H), 1.73-1.62 (m, 4H).

Example 83

(R,R)-4-Cyclopentyl-6-(hexahydro-pyrrolo[3,4-b]pyrrol-5-yl)-pyrimidin-2-ylamine

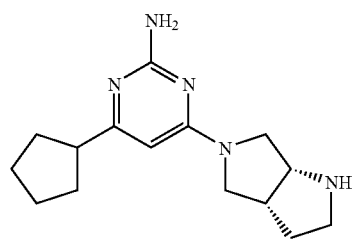

MS (ESI): mass calcd. for $C_{15}H_{23}N_5$, 273.2; m/z found, 274.2 [M+H]$^+$. $^1$H NMR (CDCl$_3$): 5.63 (s, 1H), 5.36-5.13 (m, 2H), 3.97-3.85 (m, 1H), 3.78-3.63 (m, 1H), 3.64-3.54 (m, 1H), 3.56-3.42 (m, 1H), 3.38-3.22 (m, 1H), 3.20-3.04 (m, 2H), 3.05-2.92 (m, 2H), 2.92-2.75 (m, 1H), 2.11-1.89 (m, 3H), 1.86-1.57 (m, 7H).

Example 84

4-Cyclopentyl-6-(cis-1,7-diaza-spiro[4.4]non-7-yl)-pyrimidin-2-ylamine

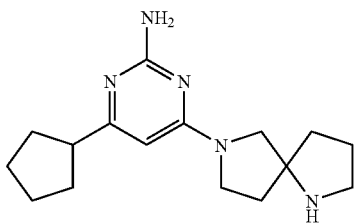

MS (ESI): mass calcd. for $C_{16}H_{25}N_5$, 287.2; m/z found, 288.2 [M+H]$^+$. $^1$H NMR (MeOD): 5.72 (s, 1H), 3.68-3.27 (m, 4H), 3.07-2.88 (m, 2H), 2.85-2.74 (m, 1H), 2.08-1.92 (m, 4H), 1.93-1.74 (m, 6H), 1.74-1.57 (m, 4H).

Example 85

4-(3-Amino-azetidin-1-yl)-6-cyclopentyl-pyrimidin-2-ylamine

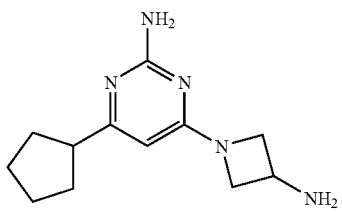

MS (ESI): mass calcd. for $C_{12}H_{19}N_5$, 233.16; m/z found, 234.3 [M+H]$^+$. $^1$H NMR (MeOD): 10.97-8.73 (br. s, 3H), 7.73 (s, 2H), 5.98 (s, 1H), 4.38 (s, 2H), 4.30-4.07 (m, 3H), 2.96-2.84 (m, 1H), 2.11-1.89 (m, 2H), 1.89-1.71 (m, 2H), 1.73-1.52 (m, 4H).

Example 86

4-Cyclopentyl-6-(trans-hexahydro-pyrrolo[3,4-b][1,4]oxazin-6-yl)-pyrimidin-2-ylamine

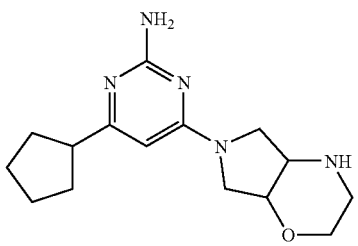

MS (ESI): mass calcd. for $C_{16}H_{23}N_5O$, 289.2; m/z found, 290.2 [M+H]$^+$. $^1$H NMR (MeOD): 5.62 (s, 1H), 4.72 (s, 2H), 3.99 (dd, J=11.7, 2.5, 2H), 3.77 (dt, J=11.7, 2.9, 1H), 3.67-3.49 (m, 2H), 3.20 (t, J=9.8, 1H), 3.13-3.03 (m, 2H), 2.98 (dd, J=12.3, 1.9, 2H), 2.86-2.76 (m, 1H), 2.07-1.91 (m, 4H), 1.83-1.57 (m, 4H).

Example 87

4-Cyclopentyl-6-(hexahydro-pyrrolo[3,4-c]pyrrol-2-yl)-pyrimidin-2-ylamine

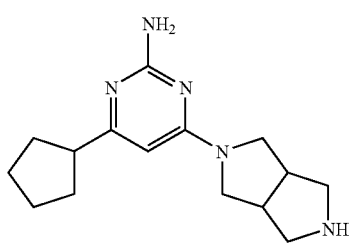

MS (ESI): mass calcd. for $C_{15}H_{23}N_5$, 273.2; m/z found, 274.3 [M+H]$^+$.

Example 88

4-Cyclopentyl-6-(cis-hexahydro-pyrrolo[3,4-b][1,4]oxazin-6-yl)-pyrimidin-2-ylamine

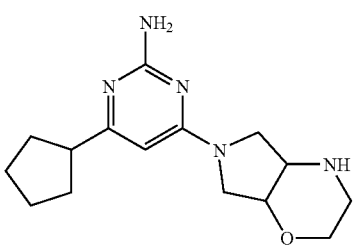

MS (ESI): mass calcd. for $C_{15}H_{23}N_5O$, 289.19; m/z found, 290.2 [M+H]$^+$.

Example 89

(2-Amino-ethyl)-6-isopropyl-pyrimidine-2,4-diamine

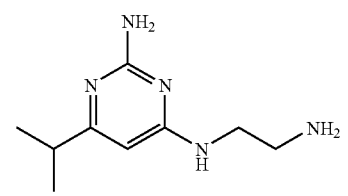

MS (ESI): mass calcd. for $C_9H_{17}N_5$, 195.15; m/z found, 196.2 [M+H]$^+$. $^1$H NMR (MeOD): 8.11 (s, 1H), 6.04 (s, 1H), 3.75 (t, J=5.8, 2H), 3.21 (t, J=5.8, 2H), 2.81 (td, J=13.7, 6.8, 1H), 1.29 (d, J=6.9, 6H).

Example 90

4-(3-Amino-azetidin-1-yl)-6-isopropyl-pyrimidin-2-ylamine

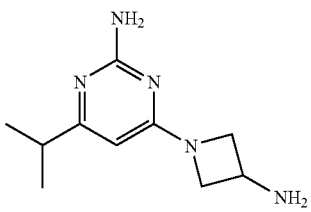

MS (ESI): mass calcd. for $C_{10}H_{17}N_5$, 207.3; m/z found, 208.3 [M+H]$^+$. $^1$H NMR (CDCl$_3$): 12.95 (s, 1H), 8.87 (s, 3H), 8.29-7.56 (br s, 2H), 6.01 (s, 1H), 4.47 (dd, J=9.9, 8.0, 1H), 4.36 (dd, J=10.3, 8.0, 1H), 4.27 (dd, J=10.5, 4.2, 1H), 4.20 (dd, J=10.9, 4.4, 1H), 4.17-4.09 (m, 1H), 2.81 (td, J=13.8, 6.9, 1H), 1.24 (d, J=6.9, 6H).

Example 91

4-(1,7-Diaza-spiro[4.4]non-7-yl)-6-isopropyl-pyrimidin-2-ylamine

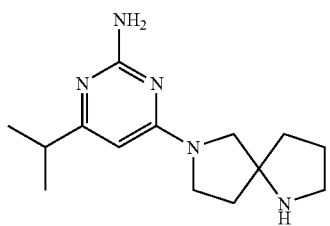

MS (ESI): mass calcd. for $C_{14}H_{23}N_5$, 261.2; m/z found, 262.1 [M+H]$^+$. $^1$H NMR (CDCl$_3$): 5.52 (s, 1H), 4.63 (s, 2H), 3.59-3.20 (m, 4H), 3.02-2.90 (m, 2H), 2.58 (td, J=13.8, 6.9, 1H), 1.95-1.85 (m, 2H), 1.85-1.65 (m, 4H), 1.14 (d, J=6.9, 6H).

Example 92

N$^4$-(2-Amino-ethyl)-6-isopropyl-N$^4$-methyl-pyrimidine-2,4-diamine

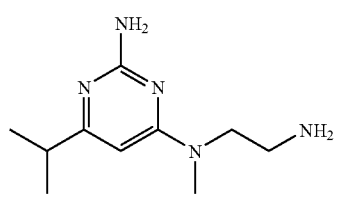

MS (ESI): mass calcd. for $C_{10}H_{19}N_5$, 209.16; m/z found, 210.2 [M+H]$^+$.

Example 93

4-(cis-Hexahydro-pyrrolo[3,4-b][1,4]oxazin-6-yl)-6-isopropyl-pyrimidin-2-ylamine

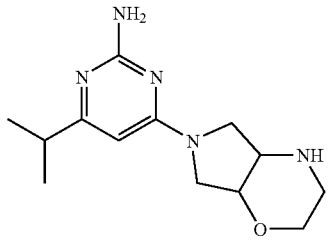

MS (ESI): mass calcd. for $C_{13}H_{21}N_5O$, 263.17; m/z found, 264.2 [M+H]$^+$.

Example 94

4-(trans-Hexahydro-pyrrolo[3,4-b][1,4]oxazin-6-yl)-6-isopropyl-pyrimidin-2-ylamine

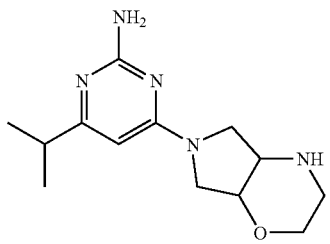

MS (ESI): mass calcd. for $C_{13}H_{21}N_5O$, 263.17; m/z found, 264.2 [M+H]$^+$.

Example 95

4-Isopropyl-6-(4-methyl-piperazin-1-yl)-pyrimidin-2-ylamine

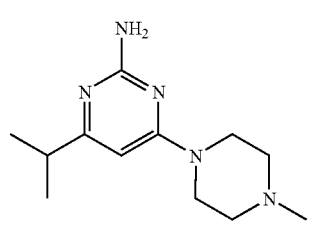

MS (ESI): mass calcd. for $C_{12}H_{21}N_5$, 263.17; m/z found, 264.2 [M+H]$^+$.

Example 96

4-(4-Methyl-piperazin-1-yl)-7,8-dihydro-5H-pyrano[4,3-d]pyrimidin-2-ylamine

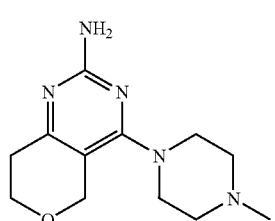

MS (ESI): mass calcd. for $C_{12}H_{19}N_5O$, 249.16; m/z found, 250.3 [M+H]$^+$. $^1$H NMR (CDCl$_3$): 4.69 (s, 2H), 4.50 (s, 2H), 4.00 (t, J=6.1, Hz, 2H), 3.32-3.28 (m, 4H), 2.74 (t, J=6.1, Hz, 2H), 2.50-2.45 (m, 4H), 2.33 (s, 3H).

Example 97

(R,R)-4-(Octahydro-pyrrolo[3,4-b]pyridin-6-yl)-7,8-dihydro-5H-pyrano[4,3-d]pyrimidin-2-ylamine

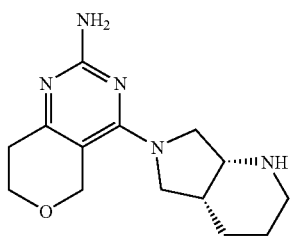

MS (ESI): mass calcd. for $C_{14}H_{21}N_5O$, 275.2; m/z found, 276.3 [M+H]$^+$. $^1$H NMR (DMSO-d$_6$): 12.97-12.63 (br s, 1H), 9.99 (s, 1H), 9.34 (s, 1H), 7.62 (s, 2H), 4.95-4.79 (m, 1H), 4.74 (d, J=13.5, 1H), 4.05-3.63 (m, 7H), 3.16 (d, J=12.1, 1H), 2.91-2.57 (m, 4H), 1.95-1.56 (m, 4H).

Example 98

(R)-4-(3-Amino-pyrrolidin-1-yl)-7,8-dihydro-5H-pyrano[4,3-d]pyrimidin-2-ylamine

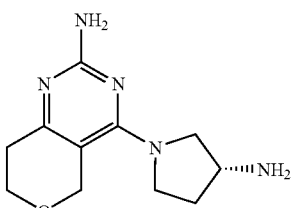

MS (ESI): mass calcd. for $C_{11}H_{17}N_5O$, 235.14; m/z found, 236.2 [M+H]$^+$.

Example 99

(R)-4-(3-Methylamino-pyrrolidin-1-yl)-7,8-dihydro-5H-pyrano[4,3-d]pyrimidin-2-ylamine

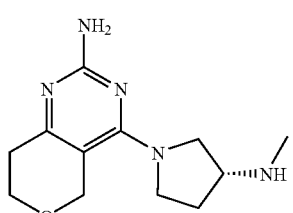

MS (ESI): mass calcd. for $C_{12}H_{19}N_5O$, 249.16; m/z found, 250.3 [M+H]$^+$.

Example 100

4-Piperazin-1-yl-7,8-dihydro-5H-pyrano[4,3-d]pyrimidin-2-ylamine

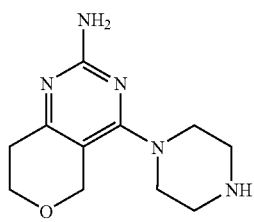

MS (ESI): mass calcd. for $C_{11}H_{17}N_5O$, 235.14; m/z found, 236.2 [M+H]$^+$.

Example 101

4-Butyl-5-methoxy-6-piperazin-1-yl-pyrimidin-2-ylamine

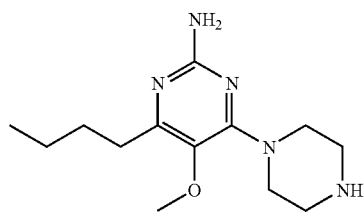

MS (ESI): mass calcd. for $C_{13}H_{23}N_5O$, 265.2; m/z found, 266.1 [M+H]$^+$. $^1$H NMR (MeOD): 4.30 (s, 4H), 3.69 (s, 3H), 3.43-3.37 (m, 4H), 2.73-2.66 (m, 2H), 1.68 (td, J=15.5, 7.6, 2H), 1.51-1.39 (m, 2H), 0.99 (t, J=7.3, 3H).

Example 102

4-Butyl-6-[1,4]diazepan-1-yl-5-methoxy-pyrimidin-2-ylamine

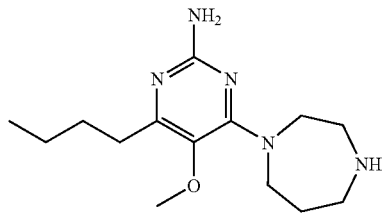

MS (ESI): mass calcd. for $C_{14}H_{25}N_5O$, 279.21; m/z found, 280.2 [M+H]$^+$.

Example 103

4-(3-Amino-azetidin-1-yl)-6-butyl-5-methoxy-pyrimidin-2-ylamine

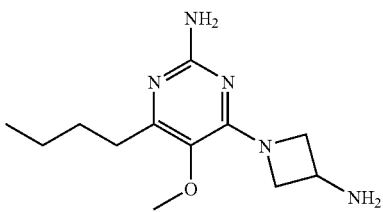

MS (ESI): mass calcd. for $C_{12}H_{21}N_5O$, 251.2; m/z found, 252.2 [M+H]$^+$.

Example 104

(R)-4-(3-Amino-pyrrolidin-1-yl)-6-butyl-5-methoxy-pyrimidin-2-ylamine

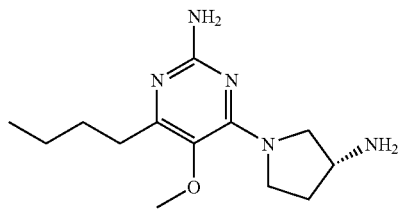

MS (ESI): mass calcd. for $C_1H_{23}N_5O$, 265.2; m/z found, 266.1 [M+H]$^+$.

Example 105

(S)-4-(3-Amino-pyrrolidin-1-yl)-6-butyl-5-methoxy-pyrimidin-2-ylamine

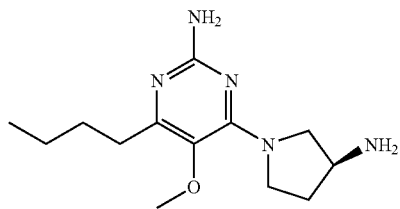

MS (ESI): mass calcd. for $C_1H_{23}N_5O$, 265.2; m/z found, 266.1 [M+H]$^+$.

Example 106

(R)-4-Butyl-5-methoxy-6-(3-methylamino-pyrrolidin-1-yl)-pyrimidin-2-ylamine

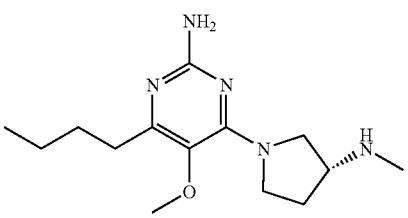

MS (ESI): mass calcd. for $C_{14}H_{25}N_5O$, 279.2; m/z found, 280.2 [M+H]$^+$.

Example 107

(S)-4-Butyl-5-methoxy-6-(3-methylamino-pyrrolidin-1-yl)-pyrimidin-2-ylamine

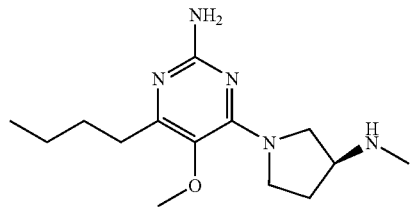

MS (ESI): mass calcd. for $C_{14}H_{25}N_5O$, 279.2; m/z found, 280.2 [M+H]$^+$.

Example 108

4-Butyl-5-methoxy-6-(4-methyl-piperazin-1-yl)-pyrimidin-2-ylamine

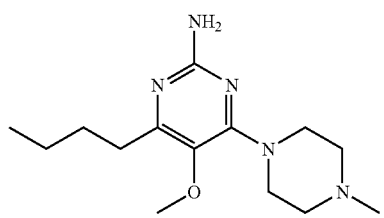

MS (ESI): mass calcd. for $C_{14}H_{25}N_5O$, 279.2; m/z found, 280.2 [M+H]$^+$.

Example 109

N$^4$-(2-Amino-ethyl)-6-butyl-5-methoxy-N$^4$-methyl-pyrimidine-2,4-diamine

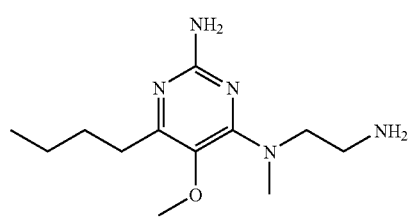

MS (ESI): mass calcd. for $C_{12}H_{23}N_5O$, 253.2; m/z found, 254.2 [M+H]$^+$.

Example 110

N$^4$-(2-Amino-ethyl)-6-butyl-5-methoxy-pyrimidine-2,4-diamine

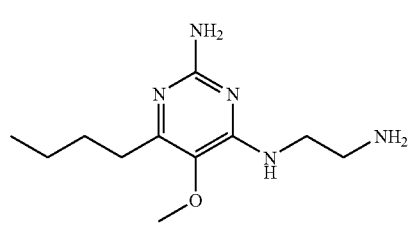

MS (ESI): mass calcd. for $C_{11}H_{21}N_5O$, 239.2; m/z found, 240.2 [M+H]$^+$.

Example 111

4-(3-Amino-azetidin-1-yl)-6-cyclopentyl-5-methoxy-pyrimidin-2-ylamine

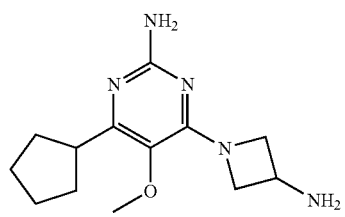

MS (ESI): mass calcd. for $C_{12}H_{19}N_5O$, 263.2; m/z found, 264.2 [M+H]$^+$. $^1$H NMR (MeOD): 4.97-4.88 (m, 1H), 4.64-4.52 (m, 2H), 4.33-4.23 (m, 2H), 3.70 (s, 3H), 3.48-3.35 (m, 1H), 2.11-2.01 (m, 2H), 1.99-1.89 (m, 2H), 1.84-1.67 (m, 4H).

Example 112

4-Cyclopentyl-6-[1,4]diazepan-1-yl-5-methoxy-pyrimidin-2-ylamine

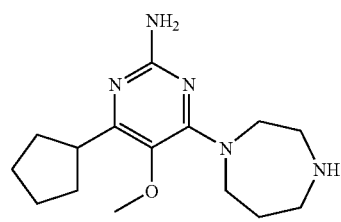

MS (ESI): mass calcd. for $C_{15}H_{25}N_5O$, 291.2; m/z found, 292.2 [M+H]$^+$. $^1$H NMR (MeOD): 4.33-3.99 (m, 4H), 3.69 (s, 3H), 3.58-3.44 (m, 3H), 3.41-3.34 (m, 2H), 2.27-2.17 (m, 2H), 2.16-2.03 (m, 2H), 2.02-1.91 (m, 2H), 1.86-1.66 (m, 4H).

Example 113

(R)-4-(3-Amino-pyrrolidin-1-yl)-6-cyclopentyl-5-methoxy-pyrimidin-2-ylamine

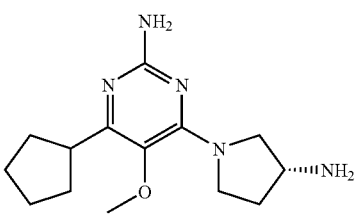

MS (ESI): mass calcd. for $C_{14}H_{23}N_5O$, 277.2; m/z found, 278.2 [M+H]$^+$.

Example 114

(S)-4-Cyclopentyl-5-methoxy-6-(3-methylamino-pyrrolidin-1-yl)-pyrimidin-2-ylamine

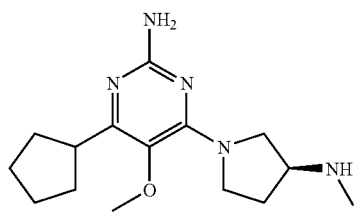

MS (ESI): mass calcd. for $C_{14}H_{23}N_5O$, 291.2; m/z found, 292.2 $[M+H]^+$.

Example 115

$N^4$-(2-Amino-ethyl)-6-cyclopentyl-5-methoxy-$N^4$-methyl-pyrimidine-2,4-diamine

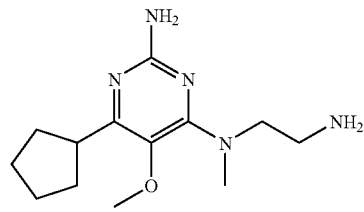

MS (ESI): mass calcd. for $C_{13}H_{23}N_5O$, 265.2; m/z found, 266.2 $[M+H]^+$.

Example 116

$N^4$-(2-Amino-ethyl)-6-cyclopentyl-5-methoxy-pyrimidine-2,4-diamine

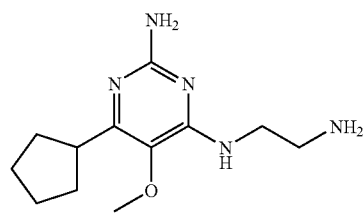

MS (ESI): mass calcd. for $C_{12}H_{21}N_5O$, 251.2; m/z found, 252.2 $[M+H]^+$.

Example 117

4-[1,4]Diazepan-1-yl-6-methoxymethyl-pyrimidin-2-ylamine

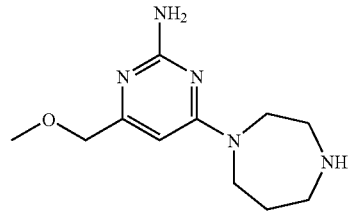

MS (ESI): mass calcd. for $C_{12}H_{19}N_5O$, 237.2; m/z found, 238.2 $[M+H]^+$. $^1$H NMR (MeOD): 6.50 (s, 1H), 4.48-4.42 (m, 2H), 4.24-4.17 (m, 1.5H), 4.11-3.99 (m, 1.5H), 3.86-3.77 (m, 1.5H), 3.48 (s, 3H), 3.46-3.41 (m, 1.5H), 3.41-3.33 (m, 2H), 2.29-2.12 (m, 2H).

Example 118

(S)-4-(3-Amino-pyrrolidin-1-yl)-6-methoxymethyl-pyrimidin-2-ylamine

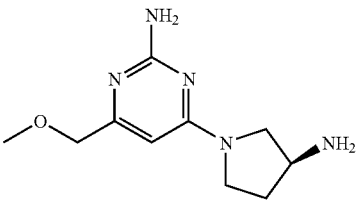

MS (ESI): mass calcd. for $C_{10}H_{17}N_5O$, 223.14; m/z found, 224.2 $[M+H]^+$.

Example 119

(S)-4-Methoxymethyl-6-(3-methylamino-pyrrolidin-1-yl)-pyrimidin-2-ylamine

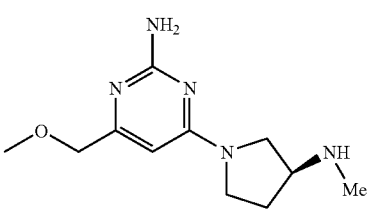

MS (ESI): mass calcd. for $C_{10}H_{17}N_5O$, 237.2; m/z found, 238.2 $[M+H]^+$.

Example 120

4-Cyclopropyl-6-(cis-5-methyl-hexahydro-pyrrolo[3,4-c]pyrrol-2-yl)-pyrimidin-2-ylamine

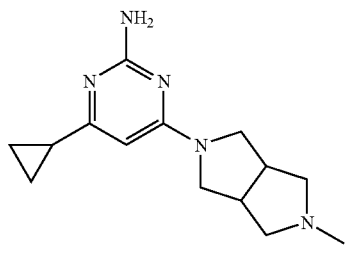

MS (ESI): mass calcd. for $C_{14}H_{21}N_5$, 259.18; m/z found, 260.3 [M+H]$^+$. $^1$H NMR (CDCl$_3$): 5.60 (s, 1H), 4.66 (s, 2H), 3.67-3.54 (m, 2H), 3.42-3.31 (m, 2H), 2.98-2.88 (m, 2H), 2.73-2.67 (m, 2H), 2.45-2.36 (m, 2H), 2.32 (s, 3H), 1.71-1.65 (m, 1H), 0.98-0.90 (m, 2H), 0.90-0.82 (m, 2H).

Example 121

4-Cyclopropyl-6-piperazin-1-yl-pyrimidin-2-ylamine

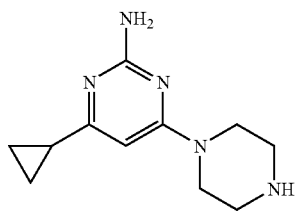

MS (ESI): mass calcd. for $C_{11}H_{17}N_5$, 219.15; m/z found, 220.3 [M+H]$^+$. $^1$H NMR (MeOD): 6.21 (s, 1H), 4.32-3.88 (m, 4H), 3.36-3.32 (m, 4H), 1.97-1.89 (m, 1H), 1.27-1.20 (m, 2H), 1.13-1.08 (m, 2H).

Example 122

4-(3-Amino-azetidin-1-yl)-6-cyclopropyl-pyrimidin-2-ylamine

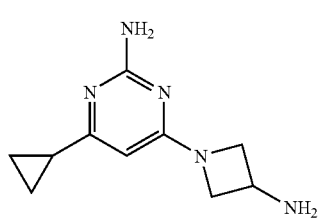

MS (ESI): mass calcd. for $C_{10}H_{15}N_5$, 205.13; m/z found, 206.3 [M+H]$^+$. $^1$H NMR (MeOD): 4.34-4.19 (m, 4H), 1.92-1.86 (m, 1H), 1.25-1.17 (m, 2H), 1.12-1.06 (m, 2H).

Example 123

(R)-4-(3-Amino-pyrrolidin-1-yl)-6-cyclopropyl-pyrimidin-2-ylamine

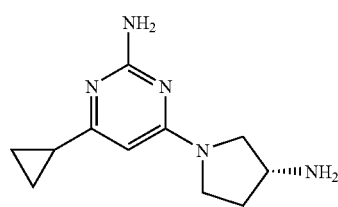

MS (ESI): mass calcd. for $C_{11}H_{17}N_5$, 219.15; m/z found, 220.3 [M+H]$^+$. $^1$H NMR (MeOD): 5.93 (s, 0.6H), 5.91 (s, 0.4H), 4.15-3.59 (m, 5H), 2.60-2.36 (m, 1H), 2.31-2.09 (m, 1H), 1.98-1.87 (m, 1H), 1.27-1.19 (m, 2H), 1.11-1.04 (m, 2H).

Example 124

4-Cyclopropyl-6-(cis-hexahydro-pyrrolo[3,4-c]pyrrol-2-yl)-pyrimidin-2-ylamine

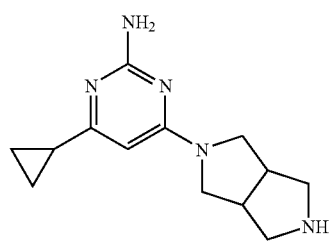

MS (ESI): mass calcd. for $C_{13}H_{19}N_5$, 245.16; m/z found, 246.3 [M+H]$^+$. $^1$H NMR (MeOD): 5.92 (s, 1H), 3.98-3.73 (m, 3H), 3.72-3.54 (m, 3H), 3.34-3.20 (m, 4H), 2.00-1.89 (m, 1H), 1.25-1.17 (m, 2H), 1.15-1.07 (m, 2H).

Example 125

(S)-4-isopropyl-6-(3-methylamino-pyrrolidin-1-yl)-pyrimidin-2-ylamine

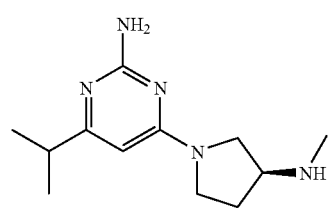

MS (ESI): mass calcd. for $C_{12}H_{21}N_5$, 235.18; m/z found, 236.3 [M+H]$^+$. $^1$H NMR (CDCl$_3$): 5.59 (s, 1H), 5.03 (s, 2H), 3.77-3.14 (m, 5H), 2.65-2.49 (m, 1H), 2.47 (s, 3H), 2.21-2.08 (m, 1H), 1.91-1.75 (m, 1H), 1.21 (s, 3H), 1.19 (s, 1H).

Example 126

(S)-4-(3-Amino-pyrrolidin-1-yl)-6-isopropyl-pyrimidin-2-ylamine

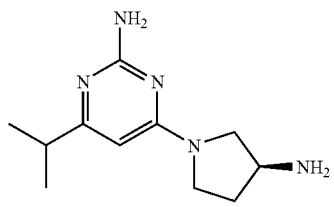

MS (ESI): mass calcd. for $C_{11}H_{19}N_5$, 221.16; m/z found, 222.3 [M+H]$^+$. $^1$H NMR (MeOD): 6.32-6.26 (m, 1H), 4.36-4.14 (m, 2H), 4.13-3.86 (m, 3H), 3.09 (q, J=6.9, 1H), 2.81-2.60 (m, 1H), 2.54-2.33 (m, 1H), 1.53 (d, J=6.9, 6H).

Example 127

(R)-4-(3-Amino-pyrrolidin-1-yl)-6-tert-butyl-pyrimidin-2-ylamine

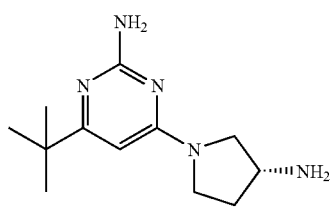

MS (ESI): mass calcd. for $C_{12}H_{21}N_5$, 235.18; m/z found, 236.3 [M+H]$^+$. $^1$H NMR (MeOD): 6.11-5.99 (m, 1H), 4.22-3.96 (m, 2H), 3.95-3.70 (m, 3H), 2.64-2.40 (m, 1H), 2.39-2.12 (m, 1H), 1.40 (s, 9H).

Example 128

4-tert-Butyl-6-(cis-5-methyl-hexahydro-pyrrolo[3,4-c]pyrrol-2-yl)-pyrimidin-2-ylamine

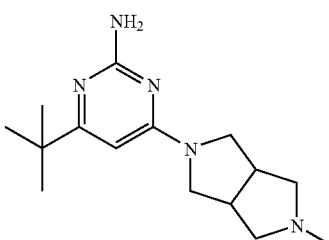

MS (ESI): mass calcd. for $C_{15}H_{25}N_5$, 275.21; m/z found, 276.2 [M+H]$^+$. $^1$H NMR (CDCl$_3$): 5.73 (s, 1H), 4.82 (s, 1H), 3.66-3.57 (m, 2H), 3.43-3.34 (m, 2H), 2.96-2.90 (m, 2H), 2.73-2.66 (m, 2H), 2.47-2.41 (m, 2H), 2.32 (s, 3H), 1.23 (s, 9H).

Example 129

(S)-4-(3-Amino-pyrrolidin-1-yl)-6-tert-butyl-pyrimidin-2-ylamine

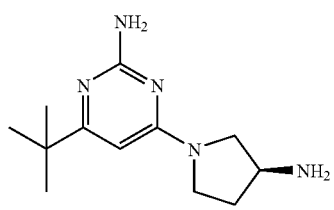

MS (ESI): mass calcd. for $C_{12}H_{21}N_5$, 235.18; m/z found, 236.2 [M+H]$^+$. $^1$H NMR (MeOD): 6.11-5.99 (m, 1H), 4.22-3.96 (m, 2H), 3.95-3.70 (m, 3H), 2.64-2.40 (m, 1H), 2.39-2.12 (m, 1H), 1.40 (s, 9H).

Example 130

(S)-4-tert-Butyl-6-(3-methylamino-pyrrolidin-1-yl)-pyrimidin-2-ylamine

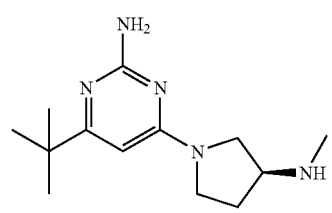

MS (ESI): mass calcd. for $C_{13}H_{23}N_5$, 249.20; m/z found, 250.2 [M+H]$^+$. $^1$H NMR (CDCl$_3$): 5.71 (s, 1H), 4.80 (s, 1H), 3.72-3.51 (m, 2H), 3.49-3.40 (m, 1H), 3.38-3.22 (m, 2H), 2.47 (s, 3H), 2.21-2.10 (m, 1H), 1.91-1.76 (m, 1H), 1.25 (s, 9H).

Example 131

$N^4$-(2-Amino-ethyl)-6-tert-butyl-$N^4$-methyl-pyrimidine-2,4-diamine

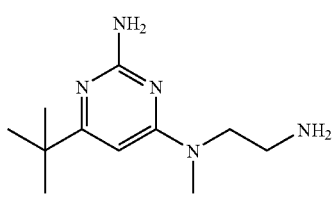

MS (ESI): mass calcd. for $C_{11}H_{21}N_5$, 223.18; m/z found, 224.4 [M+H]$^+$.

Example 132

4-tert-Butyl-6-(cis-hexahydro-pyrrolo[3,4-c]pyrrol-2-yl)-pyrimidin-2-ylamine

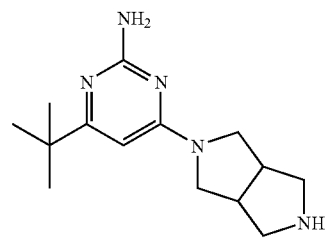

MS (ESI): mass calcd. for $C_{14}H_{23}N_5$, 261.20; m/z found, 262.3 [M+H]$^+$.

Example 133

4-(3-Amino-azetidin-1-yl)-6-tert-butyl-pyrimidin-2-ylamine

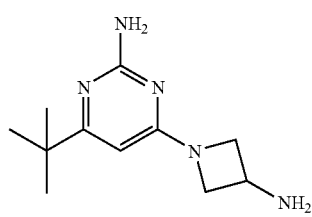

MS (ESI): mass calcd. for $C_{11}H_{19}N_5$, 221.16; m/z found, 222.3 [M+H]$^+$.

Example 134

4-tert-Butyl-6-(3,8-diaza-bicyclo[3.2.1]oct-3-yl)-pyrimidin-2-ylamine

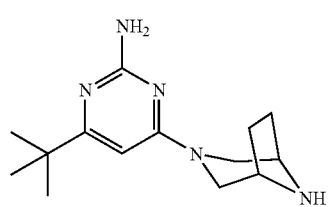

MS (ESI): mass calcd. for $C_{14}H_{23}N_5$, 261.20; m/z found, 262.3 [M+H]$^+$.

Example 135

(R)-4-(3-Amino-pyrrolidin-1-yl)-6-butyl-pyrimidin-2-ylamine

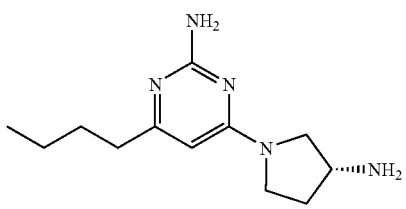

MS (ESI): mass calcd. for $C_{12}H_{21}N_5$, 235.18; m/z found, 236.2 [M+H]$^+$. $^1$H NMR (MeOD): 6.17-6.13 (m, 1H), 4.17-3.95 (m, 2H), 3.94-3.69 (m, 3H), 2.66-2.57 (m, 2H), 2.59-2.42 (m, 1H), 2.36-2.17 (m, 1H), 1.75-1.65 (m, 2H), 1.43-1.40 (m, 2H), 0.98 (t, J=7.4, 3H).

Example 136

4-Butyl-6-(4-methyl-piperazin-1-yl)-pyrimidin-2-ylamine

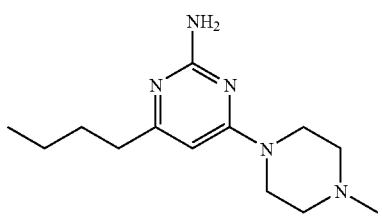

MS (ESI): mass calcd. for $C_{13}H_{23}N_5$, 249.20; m/z found, 250.2 [M+H]$^+$. $^1$H NMR (CDCl$_3$): 5.81 (s, 1H), 4.91 (s, 2H), 3.59 (t, J=4.9, 4H), 2.47-2.39 (m, 6H), 2.32 (s, 3H), 1.66-1.56 (m, 2H), 1.42-1.31 (m, 2H), 0.92 (t, J=7.34, 3H).

Example 137

(R)-4-Butyl-6-(3-methylamino-pyrrolidin-1-yl)-pyrimidin-2-ylamine

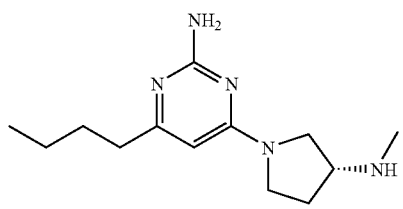

MS (ESI): mass calcd. for $C_{13}H_{23}N_5$, 249.20; m/z found, 250.2 [M+H]$^+$. $^1$H NMR (CDCl$_3$): 5.57 (s, 1H), 5.22 (s, 2H), 3.75-3.07 (m, 5H), 2.45 (s, 3H), 2.43-2.38 (m, 2H), 2.18-2.08 (m, 1H), 1.88-1.73 (m, 1H), 1.66-1.55 (m, 2H), 1.42-1.30 (m, 2H), 0.92 (t, J=7.3, 3H).

Example 138

$N^4$-(2-Amino-ethyl)-6-butyl-$N^4$-methyl-pyrimidine-2,4-diamine

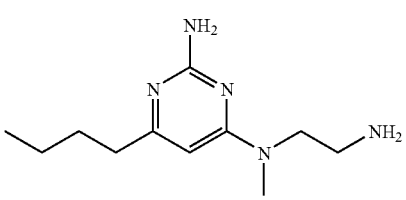

MS (ESI): mass calcd. for $C_1H_{19}N_5$, 223.18; m/z found, 224.2 [M+H]+. 1H NMR (MeOD): 6.29 (s, 1H), 4.04 (t, J=5.6, 2H), 3.36 (s, 3H), 3.31-3.27 (m, 2H), 3.27-3.23 (m, 3H), 2.69-2.61 (m, 2H), 1.76-1.65 (m, 2H), 1.49-1.38 (m, 2H), 0.98 (t, J=7.3, 3H).

Example 139

4-Butyl-6-(cis-5-methyl-hexahydro-pyrrolo[3,4-c]pyrrol-2-yl)-pyrimidin-2-ylamine

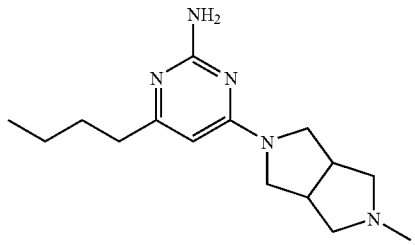

MS (ESI): mass calcd. for $C_{15}H_{25}N_5$, 275.21; m/z found, 276.2 [M+H]+. 1H NMR (CDCl3): 5.61 (s, 1H), 4.89 (s, 2H), 3.67-3.57 (m, 2H), 3.42-3.32 (m, 2H), 2.98-2.88 (m, 2H), 2.72-2.65 (m, 2H), 2.48-2.38 (m, 4H), 2.32 (s, 3H), 1.66-1.56 (m, 2H), 1.36-1.29 (m, 2H), 0.92 (t, J=7.3, 3H).

Example 140

Butyl-6-(cis-hexahydro-pyrrolo[3,4-c]pyrrol-2-yl)-pyrimidin-2-ylamine

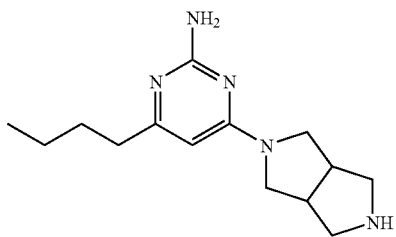

MS (ESI): mass calcd. for $C_{14}H_{23}N_5$, 261.20; m/z found, 262.2 [M+H]+. 1H NMR (MeOD): 6.12 (s, 1H), 3.98-3.76 (m, 3H), 3.72-3.56 (m, 3H), 3.41-3.32 (m, 2H), 3.29-3.22 (m, 2H), 2.65-2.57 (m, 1H), 1.75-1.64 (m, 2H), 1.43-1.31 (m, 2H), 0.98 (t, J=7.3, 1H).

Example 141

4-Butyl-6-(cis-octahydro-pyrrolo[3,4-b]pyridin-6-yl)-pyrimidin-2-ylamine

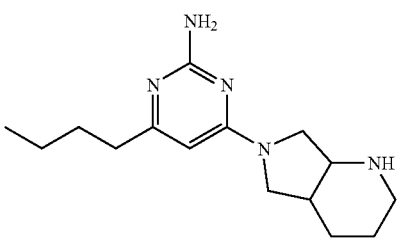

MS (ESI): mass calcd. for $C_{15}H_{25}N_5$, 275.21; m/z found, 276.2 [M+H]+. 1H NMR (MeOD): 6.15 (s, 1H), 4.15-4.04 (m, 1H), 4.01-3.76 (m, 3H), 3.69-3.58 (m, 1H), 3.40-3.32 (m, 1H), 3.14-3.01 (m, 1H), 3.00-2.77 (m, 1H), 2.66-2.59 (m, 2H), 2.03-1.78 (m, 4H), 1.76-1.65 (m, 2H), 1.49-1.38 (m, 2H), 1.02-0.96 (m, 3H).

Example 142

4-Butyl-6-piperazin-1-yl-pyrimidin-2-ylamine

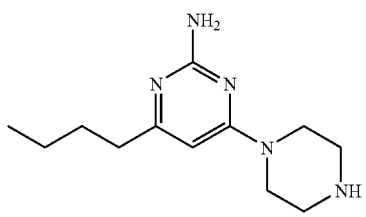

MS (ESI): mass calcd. for $C_{12}H_{21}N_5$, 235.18; m/z found, 236.2 [M+H]+. 1H NMR (MeOD): 6.49 (s, 1H), 4.35-3.97 (m, 4H), 3.45-3.34 (m, 4H), 2.68-2.60 (m, 2H), 1.76-1.65 (m, 2H), 1.50-1.38 (m, 2H), 0.98 (t, J=7.4, 3H).

Example 143

4-Butyl-6-(3,8-diaza-bicyclo[3.2.1]oct-3-yl)-pyrimidin-2-ylamine

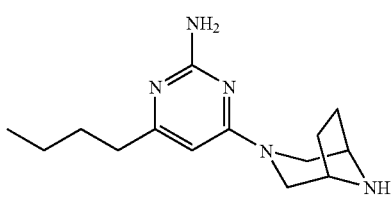

MS (ESI): mass calcd. for $C_{14}H_{23}N_5$, 261.20; m/z found, 262.3 [M+H]+. 1H NMR (MeOD): 5.76 (s, 1H), 4.44-3.71 (m, 4H), 3.22-2.93 (m, 2H), 2.48-2.38 (m, 2H), 2.05-1.85 (m, 2H), 1.75-1.56 (m, 3H), 1.43-1.29 (m, 2H), 0.96-0.89 (m, 3H).

Example 144

4-(4-Methyl-piperazin-1-yl)-6-propyl-pyrimidin-2-ylamine

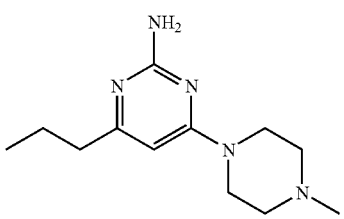

MS (ESI): mass calcd. for $C_{12}H_{21}N_5$, 235.18; m/z found, 236.2 [M+H]$^+$. $^1$H NMR (CDCl$_3$): 5.81 (s, 1H), 4.78 (s, 2H), 3.59 (t, J=4.6, 3H), 2.58-2.50 (m, 1H), 2.47-2.36 (m, 7H), 2.32 (s, 3H), 1.72-1.61 (m, 2H), 0.99-0.92 (m, 3H).

Example 145

4-(cis-5-Methyl-hexahydro-pyrrolo[3,4-c]pyrrol-2-yl)-6-propyl-pyrimidin-2-ylamine

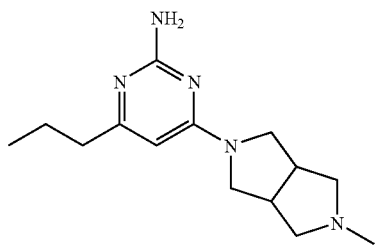

MS (ESI): mass calcd. for $C_{14}H_{23}N_5$, 261.20; m/z found, 262.2 [M+H]$^+$. $^1$H NMR (CDCl$_3$): 5.62 (s, 1H), 4.68 (s, 2H), 3.68-3.58 (m, 2H), 3.42-3.32 (m, 2H), 2.99-2.89 (m, 2H), 2.72-2.64 (m, 2H), 2.48-2.37 (m, 4H), 2.32 (s, 3H), 1.70-1.61 (m, 2H), 0.95 (t, J=7.4, 3H).

Example 146

4-Isobutyl-6-(4-methyl-piperazin-1-yl)-pyrimidin-2-ylamine

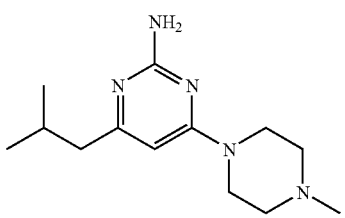

MS (ESI): mass calcd. for $C_{13}H_{23}N_5$, 249.20; m/z found, 250.2 [M+H]$^+$. $^1$H NMR (CDCl$_3$): 5.77 (s, 1H), 4.98 (s, 2H), 3.62-3.56 (m, 4H), 2.47-2.42 (m, 4H), 2.32 (s, 3H), 2.30 (s, 1H), 2.28 (s, 1H), 2.04-1.96 (m, 1H), 0.92 (d, J=6.6, 6H).

Example 147

4-Isobutyl-6-piperazin-1-yl-pyrimidin-2-ylamine

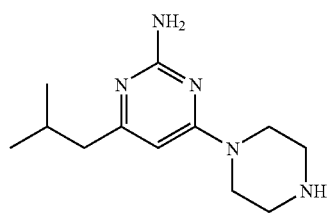

MS (ESI): mass calcd. for $C_{12}H_{21}N_5$, 235.18; m/z found, 236.2 [M+H]$^+$. $^1$H NMR (MeOD): 5.95 (s, 1H), 3.63-3.58 (m, 4H), 3.50-3.43 (m, 4H), 3.32-3.30 (m, 1H), 2.29 (s, 1H), 2.28 (s, 1H), 2.06-1.95 (m, 1H), 0.92 (d, J=6.6, 6H).

Example 148

(R)-4-Isobutyl-6-(3-methylamino-pyrrolidin-1-yl)-pyrimidin-2-ylamine

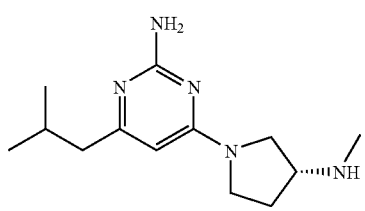

MS (ESI): mass calcd. for $C_{13}H_{23}N_5$, 249.20; m/z found, 250.2 [M+H]$^+$. $^1$H NMR (CDCl$_3$): 5.56 (s, 1H), 5.00 (s, 2H), 3.72-3.09 (m, 5H), 2.47 (s, 3H), 2.29 (s, 1H), 2.27 (s, 1H), 2.20-2.10 (m, 1H), 2.09-1.99 (m, 1H), 0.92 (d, J=6.6, 6H).

Example 149

(R)-4-(3-Amino-pyrrolidin-1-yl)-6-isobutyl-pyrimidin-2-ylamine

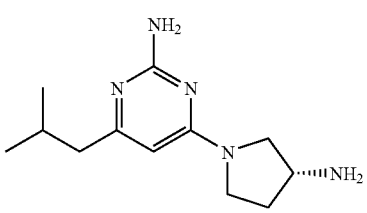

MS (ESI): mass calcd. for $C_{12}H_{21}N_5$, 235.18; m/z found, 236.2 [M+H]$^+$. $^1$H NMR (MeOD): 6.15 (s, 0.7H), 6.14 (s, 0.3H), 4.18-3.64 (m, 5H), 2.50 (s, 1H), 2.48 (s, 1H), 2.34-2.14 (m, 1H), 2.12-2.00 (m, 1H), 1.00 (d, J=6.6, 6H).

Example 150

(S)-4-Ethyl-6-(3-methylamino-pyrrolidin-1-yl)-pyrimidin-2-ylamine

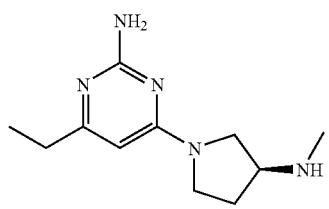

MS (ESI): mass calcd. for $C_{11}H_{19}N_5$, 221.16; m/z found, 222.2 [M+H]$^+$. $^1$H NMR (CDCl$_3$): 5.61 (s, 1H), 5.21 (s, 2H), 3.72-3.12 (m, 5H), 2.55-2.41 (m, 5H), 2.22-2.09 (m, 1H), 1.93-1.77 (m, 1H), 1.27-1.15 (t, J=7.3, 3H).

Example 151

(R)-4-Adamantan-1-yl-6-(3-methylamino-pyrrolidin-1-yl)-pyrimidin-2-ylamine

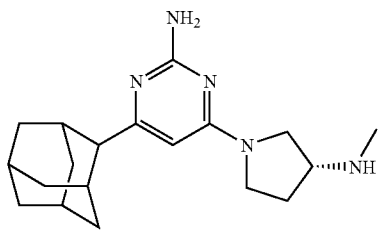

MS (ESI): mass calcd. for $C_{19}H_{29}N_5$, 327.24; m/z found, 328.4 [M+H]$^+$. $^1$H NMR (CDCl$_3$): 5.92 (s, 1H), 4.71 (s, 2H), 3.71-3.17 (m, 5H), 2.48 (s, 3H), 1.99-1.92 (m, 6H), 1.81-1.72 (m, 6H), 1.38 (s, 1H), 1.15 (s, 1H).

Example 152

4-Adamantan-1-yl-6-(4-methyl-piperazin-1-yl)-pyrimidin-2-ylamine

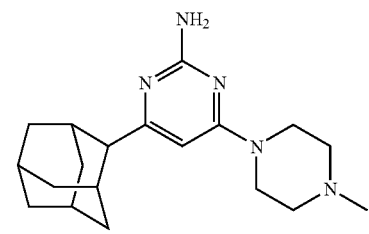

MS (ESI): mass calcd. for $C_{19}H_{29}N_5$, 327.24; m/z found, 328.4 [M+H]$^+$. $^1$H NMR (CDCl$_3$): 5.88 (s, 1H), 4.74 (s, 2H), 3.60 (t, J=5.1, 4H), 2.45 (t, J=5.1, 4H), 2.34-2.31 (m, 3H), 2.08-2.03 (m, 3H), 1.91-1.88 (m, 6H), 1.79-1.69 (m, 6H), 1.38 (s, 1H), 1.12 (s, 1H).

Example 153

4-(4-Methyl-tetrahydro-pyran-4-yl)-6-piperazin-1-yl-pyrimidin-2-ylamine

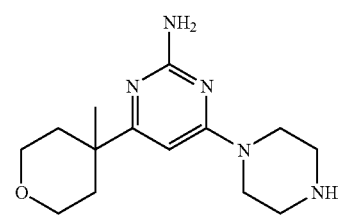

MS (ESI): mass calcd. for $C_{14}H_{23}N_5O$, 277.2; m/z found, [M+H]$^+$.=278.2. $^1$H NMR (CDCl$_3$): 5.87 (s, 1H), 4.79 (br s, 2H), 3.76-3.71 (m, 2H), 3.63-3.50 (m, 6H), 2.95-2.87 (m, 4H), 2.18-2.10 (m, 2H), 2.05-1.85 (m, 1H), 1.66-1.60 (m, 2H), 1.23 (s, 3H). The free base was treated with HCl (4 M in 1,4-dioxane; 2 equiv.) in CH$_2$Cl$_2$ to provide the bis-HCl salt (227 mg) as a white solid.

Example 154

4-(4-Methyl-piperazin-1-yl)-6-(4-methyl-tetrahydro-pyran-4-yl)-pyrimidin-2-ylamine

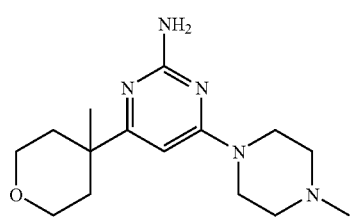

MS (ESI): mass calcd. for $C_{15}H_{25}N_5O$, 291.2; m/z found, 292.2 [M+H]$^+$. $^1$H NMR (CDCl$_3$): 5.89 (s, 1H), 4.80-4.50 (m, 2H), 3.78-3.70 (m, 2H), 3.65-3.55 (m, 5H), 2.50-2.40 (m, 4H), 2.33 (s, 3H), 2.20-2.10 (m, 2H), 1.84-1.58 (br m, 3H), 1.23 (s, 3H).

Example 155

(R)-4-(3-Methylamino-pyrrolidin-1-yl)-6-(4-methyl-tetrahydro-pyran-4-yl)-pyrimidin-2-ylamine

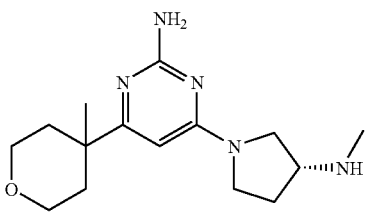

MS (ESI): mass calcd. for $C_{15}H_{25}N_5$, 291.2; m/z found, 292.2 [M+H]$^+$. $^1$H NMR (CDCl$_3$): 5.66 (s, 1H), 4.66 (br s, 2H), 3.79-3.70 (m, 2H), 3.65-3.50 (m, 4H), 3.50-3.39 (m, 1H), 3.38-3.20 (m, 2H), 2.48 (s, 3H), 2.22-2.12 (m, 3H), 1.90-1.78 (1H), 1.68-1.58 (m, 2H), 1.22 (s, 3H).

Example 156

4-(trans-2-Phenyl-cyclopropyl)-6-piperazin-1-yl-pyrimidin-2-ylamine

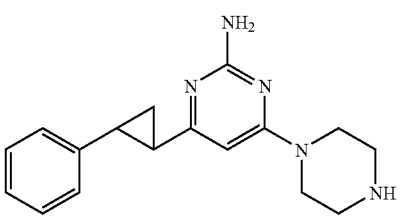

MS (ESI): mass calcd. for $C_{17}H_{21}N_5$, 295.2; m/z found, 296.2 [M+H]$^+$. $^1$H NMR (CDCl$_3$): 7.30-7.24 (m, 2H), 7.19-7.10 (m, 3H), 5.86 (s, 1H), 4.79 (br s, 2H), 3.56-3.52 (m, 4H), 2.90-2.80 (m, 4H), 2.50-2.45 (m, 1H), 2.45-2.27 (m, 1H), 2.09-1.94 (m, 1H), 1.77-1.70 (m, 1H), 1.39-1.31 (m, 1H).

Example 157

(R)-4-(3-Amino-pyrrolidin-1-yl)-6-(trans-2-phenyl-cyclopropyl)-pyrimidin-2-ylamine

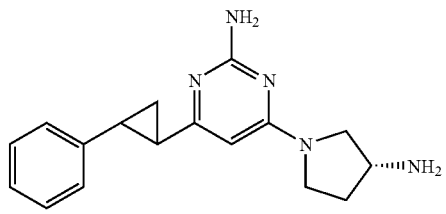

MS (ESI): mass calcd. for $C_{17}H_{21}N_5$, 295.2; m/z found, 296.2 [M+H]$^+$. $^1$H NMR (CDCl$_3$): 7.29-7.25 (m, 2H), 7.20-7.10 (m, 3H), 5.62 (s, 1H), 5.29-5.19 (br s, 2H), 3.78-3.34 (4H), 3.30-3.01 (m, 1H), 2.62-2.26 (m, 2H), 2.25-2.07 (m, 1H), 2.05-1.95 (m, 2H), 1.84-1.66 (m, 2H), 1.40-1.33 (m, 1H).

Example 158

4-(4-Methyl-piperazin-1-yl)-6-(trans-2-phenyl-cyclopropyl)-pyrimidin-2-ylamine

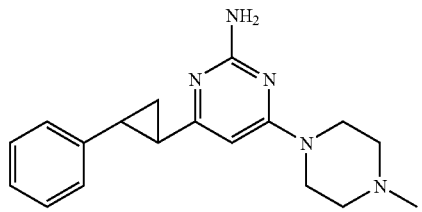

MS (ESI): mass calcd. for $C_{18}H_{23}N_5$, 309.2; m/z found, 310.2 [M+H]$^+$. $^1$H NMR (CDCl$_3$): 7.30-7.23 (m, 2H), 7.19-7.09 (m, 3H), 5.89 (s, 1H), 4.64 (br s, 2H), 3.63-3.55 (m, 4H), 2.51-2.45 (m, 1H), 2.44-2.40 (m, 4H), 2.31 (s, 3H), 1.99-1.94 (m, 1H), 1.75-1.70 (m, 1H), 1.37-1.30 (m, 1H).

Example 159

N$^4$-(2-Amino-ethyl)-6-(trans-2-phenyl-cyclopropyl)-pyrimidine-2,4-diamine

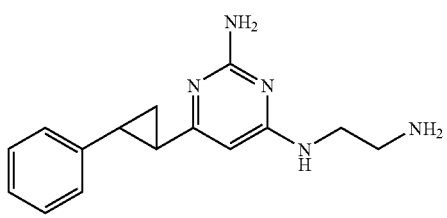

MS (ESI): mass calcd. for $C_{15}H_{19}N_5$, 269.2; m/z found, 270.2 [M+H]$^+$. $^1$H NMR (CD$_3$OD): 7.30-7.26 (m, 2H), 7.24-7.18 (m, 3H), 5.97 (s, 1H), 3.75 (t, J=5.8, 2H), 3.32-3.28 (m, 2H), 3.21 (t, J=5.8, 2H), 2.56-2.48 (m, 1H), 2.16-2.10 (m, 1H), 1.74-1.60 (m, 2H).

Example 160

(R)-4-(3-Methylamino-pyrrolidin-1-yl)-6-(trans-2-phenyl-cyclopropyl)-pyrimidin-2-ylamine

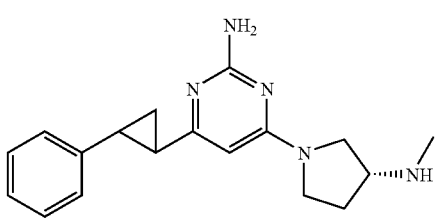

MS (ESI): mass calcd. for $C_{18}H_{23}N_5$, 309.2; m/z found, 310.2 [M+H]$^+$. $^1$H NMR (CDCl$_3$): 7.30-7.25 (m, 2H), 7.19-7.10 (m, 3H), 5.67 (s, 1H), 4.61 (br s, 2H), 3.77-3.10 (br m, 5H), 2.46 (m, 4H), 2.19-2.10 (m, 1H), 2.03-1.93 (m, 1H), 1.88-1.75 (m, 1H), 1.75-1.67 (m, 1H), 1.37-1.28 (m, 1H).

Example 161

4-(3-Amino-azetidin-1-yl)-6-indan-2-yl-pyrimidin-2-ylamine salt

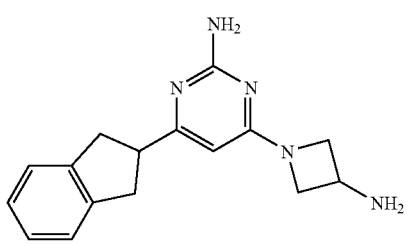

MS (ESI): mass calcd. for $C_{16}H_{19}N_5$, 281.2; m/z found, 282.2 [M+H]$^+$. $^1$H NMR (MeOD): 7.26-7.20 (m, 2H), 7.20-7.15 (m, 2H), 6.00 (s, 1H), 4.60-4.50 (m, 2H), 4.31-4.19 (m, 3H), 3.65-3.56 (m, 1H), 3.45-3.35 (m, 2H), 3.19-3.13 (m, 2H).

Example 162

(R)-4-(3-Amino-pyrrolidin-1-yl)-6-indan-2-yl-pyrimidin-2-ylamine

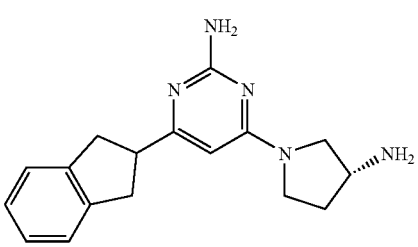

MS (ESI): mass calcd. for $C_{17}H_{21}N_5$, 295.2; m/z found, 296.2 [M+H]$^+$. $^1$H NMR (CDCl$_3$): 7.24-7.20 (m, 2H), 7.18-7.14 (m, 2H), 6.00-5.70 (m, 1H), 5.63 (s, 1H), 3.74-3.65 (m, 2H), 3.63-3.52 (m, 3H), 3.38-3.27 (m, 3H), 3.20-3.10 (m, 3H), 2.19-2.09 (m, 1H), 1.83-1.70 (m, 1H).

Example 163

4-Indan-2-yl-6-(4-methyl-piperazin-1-yl)-pyrimidin-2-ylamine

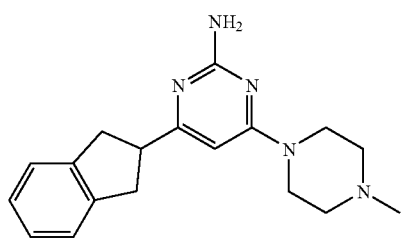

MS (ESI): mass calcd. for $C_{18}H_{23}N_5$, 309.2; m/z found, 310.2 [M+H]$^+$. $^1$H NMR (CDCl$_3$): 7.23-7.19 (m, 2H), 7.17-7.13 (m, 2H), 5.89 (s, 1H), 4.76 (br s, 2H), 3.60-3.57 (m, 4H), 3.55-3.46 (m, 1H), 3.30-3.14 (m, 4H), 2.45-2.42 (m, 4H), 2.32 (s, 3H).

Example 164

(R)-4-Indan-2-yl-6-(3-methylamino-pyrrolidin-1-yl)-pyrimidin-2-ylamine

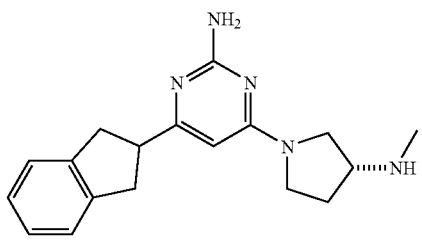

MS (ESI): mass calcd. for $C_{18}H_{23}N_5$, 309.2; m/z found, 310.2 [M+H]$^+$. $^1$H NMR (CDCl$_3$): 7.23-7.19 (m, 2H), 7.17-7.13 (m, 2H), 5.67 (s, 1H), 4.72 (br s, 2H), 3.71-3.36 (br m, 4H), 3.33-3.14 (m, 6H), 2.46 (s, 3H), 2.20-2.08 (m, 1H), 1.88-1.78 (m, 1H).

Example 165

4-Indan-2-yl-6-piperazin-1-yl-pyrimidin-2-ylamine

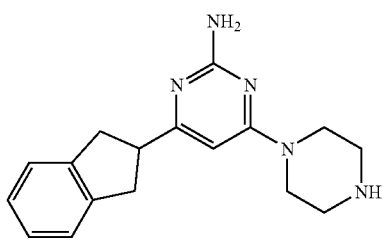

MS (ESI): mass calcd. for $C_{17}H_{21}N_5$, 295.2; m/z found, 296.2 [M+H]$^+$. $^1$H NMR (CDCl$_3$): 7.23-7.19 (m, 2H), 7.17-7.13 (m, 2H), 5.87 (s, 1H), 5.16 (br s, 2H), 3.57-3.46 (m, 5H), 3.33-3.15 (m, 4H), 2.91-2.88 (m, 4H).

Example 166

4-(3-Amino-azetidin-1-yl)-6-benzyl-pyrimidin-2-ylamine

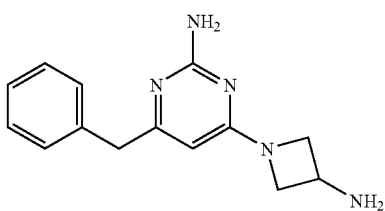

MS (ESI): mass calcd. for $C_{14}H_{17}N_5$, 255.2; m/z found, 256.1 [M+H]$^+$. $^1$H NMR (CDCl$_3$): 7.33-7.19 (m, 5H), 5.39 (s, 1H), 4.83 (br s, 2H), 4.25-4.18 (m, 2H), 3.95-3.86 (m, 1H), 3.77 (s, 2H), 3.61-3.57 (m, 2H).

Example 167

(R)-4-(3-Amino-pyrrolidin-1-yl)-6-benzyl-pyrimidin-2-ylamine

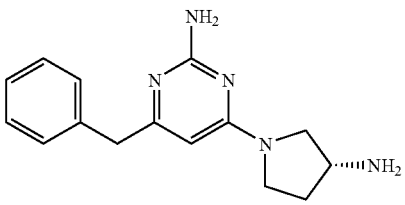

MS (ESI): mass calcd. for $C_{15}H_{19}N_5$, 269.2; m/z found, 270.12 [M+H]$^+$. $^1$H NMR (CDCl$_3$): 7.34-7.21 (m, 5H), 5.72 (br s, 2H), 5.45 (s, 1H), 3.83 (s, 2H), 3.71-3.60 (m, 2H), 3.60-2.84 (br m, 5H), 2.21-2.04 (m, 1H), 1.84-1.63 (m, 1H).

Example 168

N$^4$-(2-Amino-ethyl)-6-indan-2-yl-pyrimidine-2,4-diamine

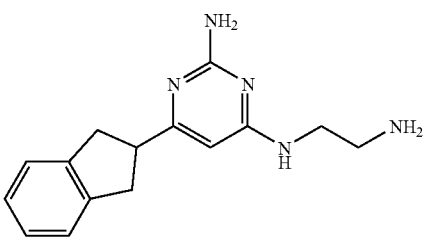

MS (ESI): mass calcd. for $C_{15}H_{19}N_5$, 269.2; m/z found, 270.2 [M+H]$^+$. $^1$H NMR (MeOD): 8.49 (s, 2H), 7.26-7.20 (m, 2H), 5.94 (s, 1H), 3.67 (t, J=5.7, 2H), 3.59-3.51 (m, 1H), 3.39-3.32 (m, 2H), 3.18-3.06 (m, 4H).

Example 169

(R)-4-(2,3-Dihydro-benzofuran-2-yl)-6-(3-methylamino-pyrrolidin-1-yl)-pyrimidin-2-ylamine

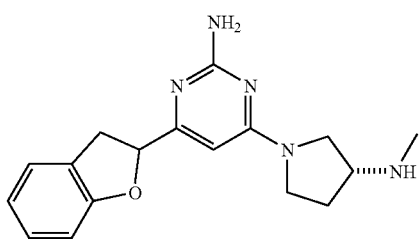

MS (ESI): mass calcd. for $C_{17}H_{21}N_5O$, 311.2; m/z found, 312.2 $[M+H]^+$.

Example 170

4-(cis-Hexahydro-pyrrolo[3,4-c]pyrrol-2-yl)-6-(4-methyl-tetrahydro-pyran-4-yl)-pyrimidin-2-ylamine

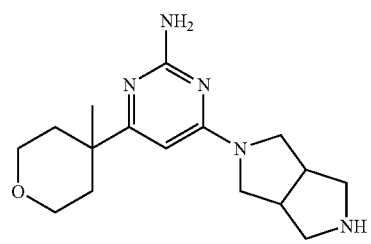

MS (ESI): mass calcd. for $C_{16}H_{25}N_5O$, 303.2; m/z found, 304.2 $[M+H]^+$.

Example 171

4-(2,3-Dihydro-benzofuran-2-yl)-6-piperazin-1-yl-pyrimidin-2-ylamine

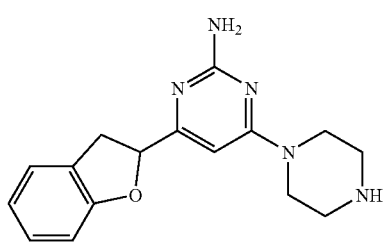

MS (ESI): mass calcd. for $C_{16}H_{19}N_5O$, 297.2; m/z found, 298.2 $[M+H]^+$.

Example 172

4-(3-Amino-azetidin-1-yl)-6-(2,3-dihydro-benzofuran-2-yl)-pyrimidin-2-ylamine

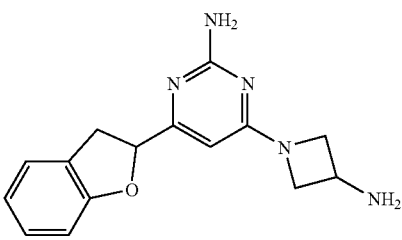

MS (ESI): mass calcd. for $C_{15}H_{17}N_5O$, 283.2; m/z found, 284.1 $[M+H]^+$.

Example 173

4-(cis-Hexahydro-pyrrolo[3,4-c]pyrrol-2-yl)-6-indan-2-yl-pyrimidin-2-ylamine

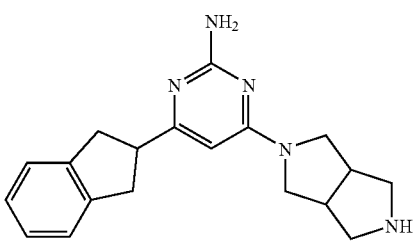

MS (ESI): mass calcd. for $C_{19}H_{23}N_5$, 321.2; m/z found, 322.2 $[M+H]^+$.

Example 174

(R)-4-(3-Amino-pyrrolidin-1-yl)-6-(4-methyl-tetrahydro-pyran-4-yl)-pyrimidin-2-ylamine

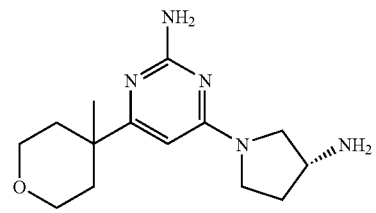

MS (ESI): mass calcd. for $C_{14}H_{23}N_5O$, 277.2; m/z found, 278.2 $[M+H]^+$.

Example 175

(R)-4-(3-Amino-pyrrolidin-1-yl)-6-(tetrahydro-pyran-4-yl)-pyrimidin-2-ylamine

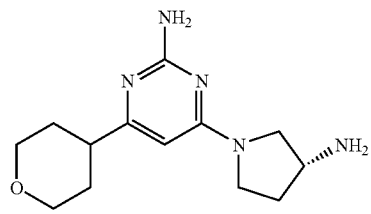

MS (ESI): mass calcd. for $C_{13}H_{21}N_5O$, 263.17; m/z found, 264.2 [M+H]$^+$. $^1$H NMR (CD$_3$OD): 5.78 (s, 1H), 4.05-3.97 (m, 2H), 3.80-3.59 (br m, 3H), 3.56-3.45 (m, 3H), 2.67-2.56 (m, 1H), 2.35-2.54 (m, 1H), 2.03-1.89 (m, 1H), 1.81-1.70 (m, 4H).

Example 176

N$^4$-(2-Amino-ethyl)-6-(tetrahydro-pyran-4-yl)-pyrimidine-2,4-diamine

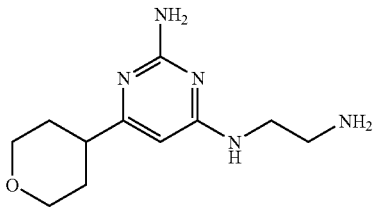

MS (ESI): mass calcd. for $C_{11}H_{19}N_5O$, 237.2; m/z found, 238.2 [M+H]$^+$.

Example 177

N$^4$-(2-Amino-ethyl)-N$^4$-methyl-6-(tetrahydro-pyran-4-yl)-pyrimidine-2,4-diamine

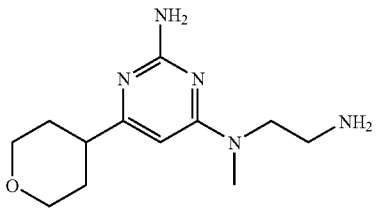

MS (ESI): mass calcd. for $C_{12}H_{21}N_5O$, 251.2; m/z found, 252.2 [M+H]$^+$.

Example 178

(R)-4-(3-Amino-pyrrolidin-1-yl)-6-phenethyl-pyrimidin-2-ylamine

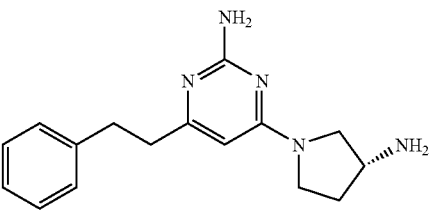

MS (ESI): mass calcd. for $C_{16}H_{21}N_5$, 283.2; m/z found, 284.2 [M+H]$^+$=284.2. $^1$H NMR (CDCl$_3$): 7.29-7.15 (m, 5H), 5.54 (s, 1H), 5.04 (br s, 2H), 3.75-3.05 (br m, 5H), 2.97 (dd, J=12.9, 6.3, 2H), 2.74 (app dd, J=9.5, 6.7, 2H), 2.13 (dt, J=12.8, 6.4, 2H), 1.80-1.51 (br m, 3H).

Example 179

4-(4-Methyl-piperazin-1-yl)-6-phenethyl-pyrimidin-2-ylamine

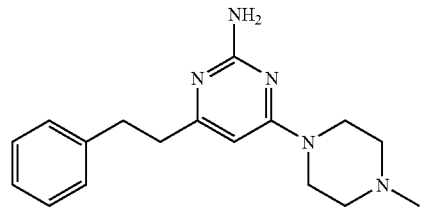

MS (ESI): mass calcd. for $C_{17}H_{23}N_5$, 297.2; m/z found, 298.2 [M+H]$^+$. $^1$H NMR (CDCl$_3$): 7.30-7.15 (m, 5H), 5.75 (s, 1H), 4.81 (br s, 2H), 3.59-3.55 (m, 4H), 2.96 (dd, J=9.6, 6.6, 2H), 2.74 (dd, J=9.5, 6.7, 2H), 2.44-2.40 (m, 4H), 2.31 (s, 3H).

Example 180

(R)-4-(3-Methylamino-pyrrolidin-1-yl)-6-phenethyl-pyrimidin-2-ylamine

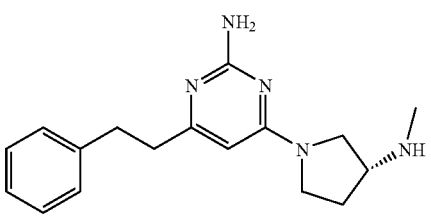

MS (ESI): mass calcd. for $C_{17}H_{23}N_5$, 297.20; m/z found, 298.2 [M+H]$^+$. $^1$H NMR (CDCl$_3$): 7.30-7.15 (m, 5H), 5.55 (s, 1H), 4.93 (br s, 2H), 3.80-3.10 (br m, 5H), 2.98-2.94 (m, 2H), 2.71-2.75 (m, 2H), 2.45 (s, 3H), 2.13 (dt, J=12.9, 6.3, 1H), 1.84-1.74 (m, 1H).

Example 181

4-(4-Methyl-piperazin-1-yl)-6-(3,3,3-trifluoro-propyl)-pyrimidin-2-ylamine

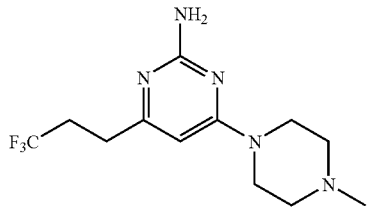

MS (ESI): mass calcd. for $C_{12}H_{18}F_3N_5$, 289.15; m/z found, 290.2 [M+H]$^+$. $^1$H NMR (MeOD): 6.03 (s, 1H), 3.67-3.59 (m, 3H), 2.66 (dd, J=10.3, 6.2, 2H), 2.57-2.43 (m, 6H), 2.31 (s, 3H).

Example 182

4-Piperazin-1-yl-6-(3,3,3-trifluoro-propyl)-pyrimidin-2-ylamine

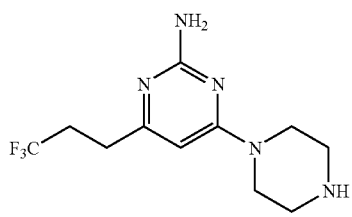

MS (ESI): mass calcd. for $C_{11}H_{16}F_3N_5$, 275.14; m/z found, 276.2 [M+H]$^+$. $^1$H NMR (MeOD): 6.04 (s, 1H), 3.67-3.62 (m, 4H), 2.95-2.87 (m, 4H), 2.67 (dd, J=10.2, 6.2, 2H), 2.58-2.43 (m, 2H).

Example 183

(R)-4-(3-Methylamino-pyrrolidin-1-yl)-6-(3,3,3-trifluoro-propyl)-pyrimidin-2-ylamine

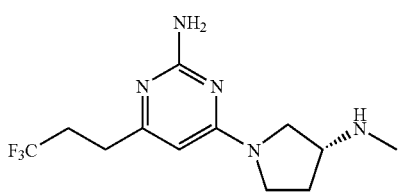

MS (ESI): mass calcd. for $C_{12}H_{18}F_3N_5$, 289.15; m/z found, 290.2 [M+H]$^+$. $^1$H NMR (MeOD): 5.78 (s, 1H), 3.71-3.52 (m, 2H), 3.51-3.38 (m, 1H), 3.38-3.22 (m, 2H), 2.65 (dd, J=10.3, 6.1, 2H), 2.57-2.44 (m, 2H), 2.41 (s, 3H), 2.20 (dtd, J=13.2, 5.5, 1H), 1.94-1.80 (m, 1H).

Example 184

(R)-4-(3-Amino-pyrrolidin-1-yl)-6-(3,3,3-trifluoro-propyl)-pyrimidin-2-ylamine

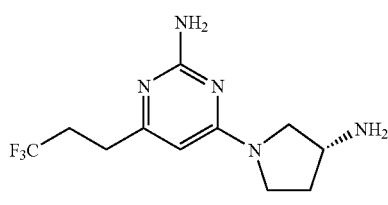

MS (ESI): mass calcd. for $C_{11}H_{16}F_3N_5$, 275.14; m/z found, 276.2 [M+H]$^+$. $^1$H NMR (MeOD): 5.78 (s, 1H), 3.71-3.55 (m, 3H), 3.53-3.41 (m, 1H), 3.25-3.16 (m, 1H), 2.66 (dd, J=10.2, 6.2, 2H), 2.57-2.43 (m, 2H), 2.25-2.14 (m, 1H), 1.90-1.78 (m, 1H).

Example 185

4-Cyclopentyl-5-methoxy-6-(4-methyl-piperazin-1-yl)-pyrimidin-2-ylamine

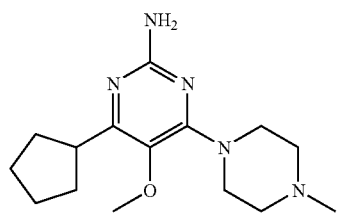

MS (ESI): mass calcd. for $C_{15}H_{25}N_5O$, 291.2; m/z found, 292.3 [M+H]$^+$. $^1$H NMR (MeOD): 3.8-3.7 (m, 4H), 3.6 (s, 3H), 3.5-3.4 (m, 1H), 2.6-2.6 (m, 4H), 2.4 (s, 3H), 1.9-1.8 (m, 4H), 1.8-1.6 (m, 4H)

Example 186

4-Cyclopentyl-5-methoxy-6-piperazin-1-yl-pyrimidin-2-ylamine

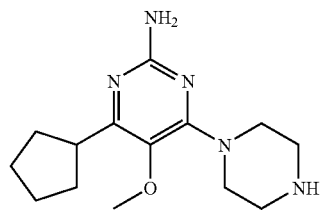

MS (ESI): mass calcd. for $C_{14}H_{23}N_5O$, 277.1; m/z found, 278.3 [M+H]$^+$. $^1$H NMR (MeOD): 3.7-3.6 (m, 4H), 3.6 (s, 3H), 3.5-3.4 (m, 1H), 3.0-2.8 (m, 4H), 1.9-1.6 (m, 8H).

Example 187

(R)-4-Cyclopentyl-5-methoxy-6-(3-methylamino-pyrrolidin-1-yl)-pyrimidin-2-ylamine

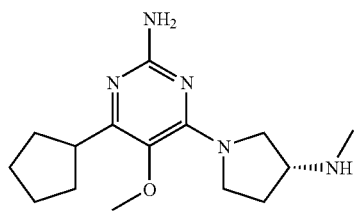

MS (ESI): mass calcd. for $C_{15}H_{25}N_5O$, 291.2; m/z found, 292.2 [M+H]$^+$. $^1$H NMR (MeOD): 3.83 (dd, J=11.7, 6.3, 1H), 3.80-3.74 (m, 1H), 3.70-3.62 (m, 1H), 3.54 (s, 3H), 3.48 (dd, J=11.6, 5.4, 1H), 3.43-3.34 (m, 1H), 3.30-3.22 (m, 1H), 2.41 (s, 3H), 2.20-2.10 (m, 1H), 1.93-1.62 (m, 9H).

Example 188

(R,R)-4-Cyclopentyl-5-methoxy-6-(octahydro-pyrrolo[3,4-b]pyridin-6-yl)-pyrimidin-2-ylamine

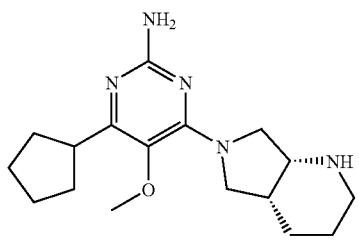

MS (ESI): mass calcd. for $C_{17}H_{27}N_5O$, 317.2; m/z found, 318.2 [M+H]$^+$. $^1$H NMR (MeOD): 4.34-4.17 (m, 1H), 4.12-3.82 (m, 3H), 3.75-3.68 (m, 3H), 3.56-3.45 (m, 1H), 3.42-3.34 (m, 1H), 3.11-3.02 (m, 1H), 2.91-2.73 (m, 1H), 2.18-2.03 (m, 2H), 2.02-1.59 (m, 11H).

Example 189

N$^4$-(2-Amino-ethyl)-N$^4$-methyl-6-(tetrahydro-furan-3-yl)-pyrimidine-2,4-diamine

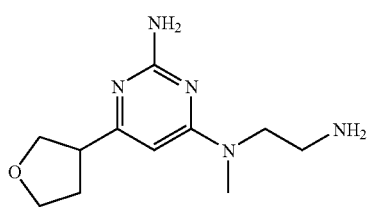

MS (ESI): mass calcd. for $C_{11}H_{19}N_5O$, 237.2; m/z found, 238.2 [M+H]$^+$. $^1$H NMR (CDCl$_3$): 5.71 (s, 1H), 4.98 (s, 2H), 4.19-3.93 (m, 2H), 3.90-3.80 (m, 2H), 3.65-3.51 (m, 1H), 3.44 (s, 3H), 3.31-3.07 (m, 1H), 2.88-2.84 (m, 2H), 2.49 (s, 3H), 2.30-2.04 (m, 2H).

Example 190

4-(cis-Octahydro-pyrrolo[3,4-b]pyridin-6-yl)-6-(tetrahydro-furan-3-yl)-pyrimidin-2-ylamine

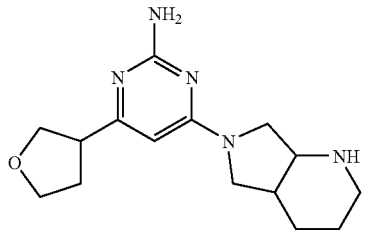

MS (ESI): mass calcd. for $C_{15}H_{23}N_5O$, 289.2; m/z found, 290.2 [M+H]$^+$. $^1$H NMR (CDCl$_3$): 5.66 (s, 1H), 5.25 (s, 2H), 4.11-3.96 (m, 2H), 3.90-3.81 (m, 2H), 3.72-3.28 (m, 5H), 3.28-3.15 (m, 1H), 3.03-2.93 (m, 1H), 2.70-2.59 (m, 1H), 2.47-2.18 (m, 3H), 2.18-2.04 (m, 1H), 1.86-1.68 (m, 2H), 1.66-1.57 (m, 1H), 1.54-1.43 (m, 1H).

Example 191

(R)-4-(3-Methylamino-pyrrolidin-1-yl)-6-(tetrahydro-furan-3-yl)-pyrimidin-2-ylamine

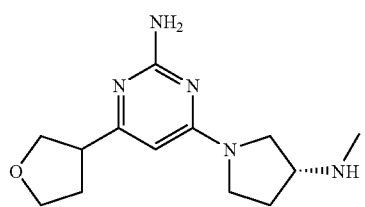

MS (ESI): mass calcd. for $C_{13}H_{21}N_5O$, 263.2; m/z found, 264.2 [M+H]$^+$. $^1$H NMR (CDCl$_3$): 5.64 (s, 1H), 5.23 (s, 2H), 4.15-3.94 (m, 2H), 3.90-3.80 (m, 2H), 3.70-3.14 (m, 6H), 2.46 (s, 3H), 2.30-2.06 (m, 3H), 1.94-1.43 (m, 2H).

Example 192

4-[1,4]Diazepan-1-yl-6-(tetrahydro-furan-3-yl)-pyrimidin-2-ylamine

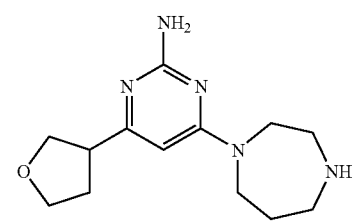

MS (ESI): mass calcd. for $C_{13}H_{21}N_5O$, 263.2; m/z found, 264.2 [M+H]$^+$. $^1$H NMR (CDCl$_3$): 5.77 (s, 1H), 5.10 (s, 2H), 4.09-3.97 (m, 2H), 3.88-3.82 (m, 2H), 3.72-3.59 (m, 4H), 3.24-3.16 (m, 1H), 2.99-2.94 (m, 2H), 2.88-2.79 (m, 2H), 2.32-2.05 (m, 2H), 2.04-1.88 (m, 1H), 1.89-1.78 (m, 2H).

The compounds in Examples 193-194 were obtained by chiral HPLC separation of the enantiomers of Example 56 (column, ADH; eluent, 95% (hexanes/0.2% TEA)/5% [(1:1 MeOH/EtOH)/0.2% TEA].

Example 193

(−)-4-Piperazin-1-yl-6-(tetrahydro-furan-3-yl)-pyrimidin-2-ylamine

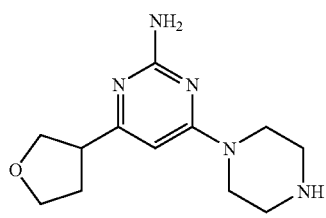

$[\alpha]^{25}_D$ −9.0° (c 1.00, CH$_3$OH). MS (ESI): mass calcd. for C$_{12}$H$_{19}$N$_5$O, 249.2; m/z found, 250.2 [M+H]$^+$. $^1$H NMR (CDCl$_3$): 5.86 (s, 1H), 5.80-4.99 (m, 3H), 4.06-3.97 (m, 2H), 3.90-3.80 (m, 2H), 3.69-3.54 (m, 4H), 3.30-3.18 (m, 1H), 3.02-2.87 (m, 4H), 2.33-2.21 (m, 1H), 2.17-2.05 (m, 1H).

Example 194

(+)-4-Piperazin-1-yl-6-(tetrahydro-furan-3-yl)-pyrimidin-2-ylamine

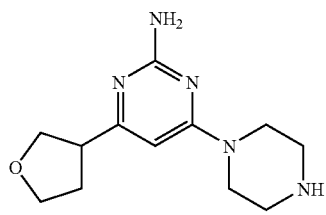

$[\alpha]^{25}_D$ +8.6° (c 1.00, CH$_3$OH). MS (ESI): mass calcd. for C$_{12}$H$_{19}$N$_5$O, 249.2; m/z found, 250.2 [M+H]$^+$. $^1$H NMR (CDCl$_3$): 5.86 (s, 1H), 5.80-4.99 (m, 3H), 4.06-3.97 (m, 2H), 3.90-3.80 (m, 2H), 3.69-3.54 (m, 4H), 3.30-3.18 (m, 1H), 3.02-2.87 (m, 4H), 2.33-2.21 (m, 1H), 2.17-2.05 (m, 1H).

Example 195

N$^4$-(2-Amino-ethyl)-6-(tetrahydro-furan-3-yl)-pyrimidine-2,4-diamine

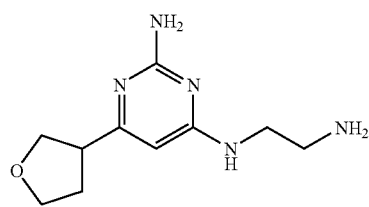

MS (ESI): mass calcd. for C$_{10}$H$_{17}$N$_5$O, 223.1; m/z found, 224.2 [M+H]$^+$. $^1$H NMR (CDCl$_3$): 5.95 (br s, 1H), 5.67 (s, 1H), 5.37 (s, 2H), 4.06-3.96 (m, 2H), 3.89-3.79 (m, 2H), 3.33 (s, 2H), 3.23-3.13 (m, 1H), 2.89 (t, J=5.8, 2H), 2.28-2.16 (m, 1H), 2.15-2.05 (m, 1H), 1.81 (br s, 2H).

Example 196

N$^4$-(3-Amino-propyl)-6-(tetrahydro-furan-3-yl)-pyrimidine-2,4-diamine

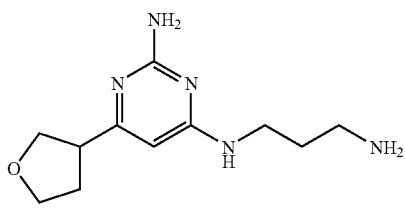

MS (ESI): mass calcd. for C$_{11}$H$_{19}$N$_5$O, 237.2; m/z found, 238.2 [M+H]$^+$. $^1$H NMR (CDCl$_3$): 5.83 (s, 1H), 4.68-4.42 (m, 5H), 4.07-3.95 (m, 2H), 3.88-3.76 (m, 2H), 3.47 (t, J=5.9, 2H), 3.26-3.16 (m, 1H), 2.94 (t, J=6.5, 2H), 2.35-2.22 (m, 1H), 2.13-1.99 (m, 1H), 1.99-1.86 (m, 2H).

Example 197

N$^4$-Methyl-N$^4$-(2-methylamino-ethyl)-6-(tetrahydro-furan-3-yl)-pyrimidine-2,4-diamine

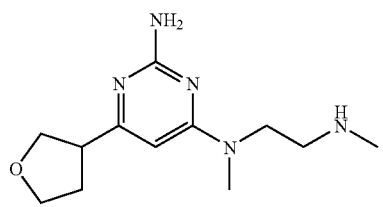

MS (ESI): mass calcd. for C$_{12}$H$_{21}$N$_5$O, 251.2; m/z found, 252.2 [M+H]$^+$. $^1$H NMR (CDCl$_3$): 5.79 (s, 1H), 5.36 (br s, 2H), 4.08-3.96 (m, 2H), 3.89-3.80 (m, 2H), 3.62 (t, J=6.3, 2H), 3.25-3.15 (m, 1H), 3.01 (s, 3H), 2.78 (t, J=6.5, 2H), 2.45 (s, 3H), 2.28-2.08 (m, 2H), 1.57 (s, 1H).

Example 198

N$^4$-(2-Methylamino-ethyl)-6-(tetrahydro-furan-3-yl)-pyrimidine-2,4-diamine

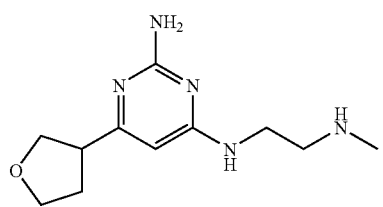

MS (ESI): mass calcd. for $C_1H_{19}N_5O$, 237.2; m/z found, 238.2 [M+H]+. 1H NMR (CDCl3): 5.79 (s, 1H), 5.21 (s, 2H), 4.09-3.97 (m, 2H), 3.89-3.82 (m, 2H), 3.56 (t, J=6.5, 2H), 3.26-3.15 (m, 1H), 3.02 (s, 3H), 2.89 (t, J=6.6, 2H), 2.28-2.08 (m, 2H), 1.44 (br s, 2H).

Example 199

5-Fluoro-4-methyl-6-(4-methyl-piperazin-1-yl)-pyrimidin-2-ylamine

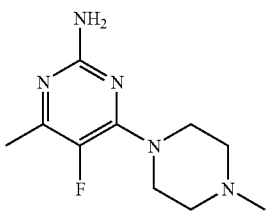

MS (ESI): mass calcd. for $C_{10}H_{16}FN_5$, 225.1; m/z found, 226.2 [M+H]+. 1H NMR (CDCl3): 4.76 (s, 2H), 3.72-3.68 (m, 4H), 2.48-2.44 (m, 4H), 2.31 (s, 3H), 2.21 (d, J=3.5, 3H).

Example 200

5-Fluoro-4-methyl-6-(octahydro-pyrrolo[3,4-b]pyridin-6-yl)-pyrimidin-2-ylamine

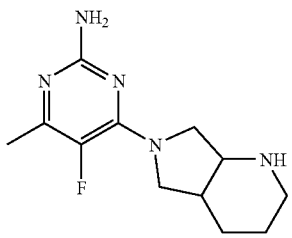

MS (ESI): mass calcd. for $C_{12}H_{18}FN_5$, 251.2; m/z found, 252.2 [M+H]+. 1H NMR (CDCl3): 5.05 (s, 2H), 3.78-3.56 (m, 5H), 3.40-3.34 (m, 1H), 3.06-2.97 (m, 1H), 2.70-2.61 (m, 1H), 2.34-2.24 (m, 1H), 2.17 (d, J=3.4, 3H), 1.81-1.43 (m, 4H).

Example 201

5-Fluoro-4-methyl-6-piperazin-1-yl-pyrimidin-2-ylamine

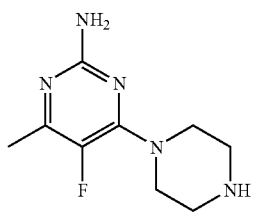

MS (ESI): mass calcd. for $C_9H_{14}FN_5$, 211.1; m/z found, 212.1 [M+H]+. 1H NMR (CDCl3): 4.03-3.94 (m, 3H), 3.75-3.61 (m, 4H), 3.04-2.79 (m, 4H), 2.27-2.11 (m, 3H).

Example 202

(R)-5-Fluoro-4-methyl-6-(3-methylamino-pyrrolidin-1-yl)-pyrimidin-2-ylamine

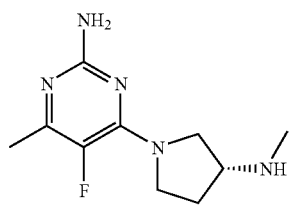

MS (ESI): mass calcd. for $C_{10}H_{16}FN_5$, 225.1; m/z found, 226.1 [M+H]+. 1H NMR (CDCl3): 5.37 (s, 2H), 3.78-3.67 (m, 2H), 3.65-3.56 (m, 1H), 3.47-3.38 (m, 1H), 3.28-3.20 (m, 1H), 2.43 (s, 3H), 2.15 (d, J=3.3, 3H), 2.10-1.99 (m, 1H), 1.84-1.71 (m, 1H), 1.48 (s, 1H).

Example 203

$N^4$-(2-Amino-ethyl)-5-fluoro-6,$N^4$-dimethyl-pyrimidine-2,4-diamine

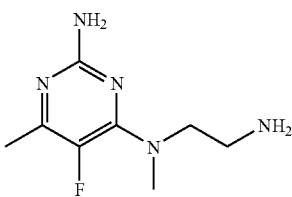

MS (ESI): mass calcd. for $C_8H_{14}FN_5$, 199.1; m/z found, 200.1 [M+H]+. 1H NMR (CDCl3): 4.92 (s, 2H), 3.56 (t, J=6.3, 2H), 3.13 (d, J=2.9, 3H), 2.92 (t, J=6.6, 2H), 2.19 (d, J=3.6, 3H), 1.41 (br s, 2H).

Example 204

4-Piperazin-1-yl-6-pyridin-4-ylmethyl-pyrimidin-2-ylamine

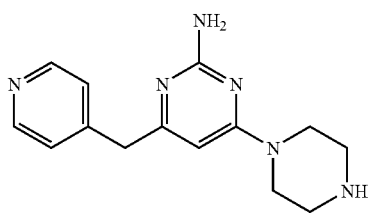

MS (ESI): mass calcd. for $C_{14}H_{18}N_6$, 270.2; m/z found, 271.2 [M+H]+. 1H NMR (CDCl3): 8.44 (dd, J=4.5, 1.6, 2H), 7.29 (d, J=6.1, 2H), 5.89 (s, 1H), 4.71 (br s, 3H), 3.79 (s, 2H), 3.60-3.56 (m, 4H), 2.90-2.85 (m, 4H).

Example 205

(R)-4-(3-Methylamino-pyrrolidin-1-yl)-6-pyridin-4-ylmethyl-pyrimidin-2-ylamine

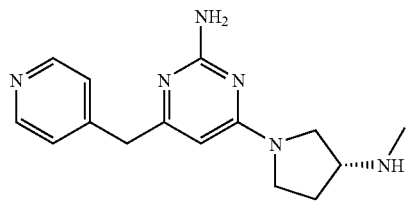

MS (ESI): mass calcd. for C$_{15}$H$_{20}$N$_6$, 284.2; m/z found, 285.2 [M+H]$^+$. $^1$H NMR (CDCl$_3$): 8.49 (dd, J=4.5, 1.6, 2H), 7.18 (d, J=6.0, 2H), 5.52 (s, 1H), 5.26 (s, 2H), 3.73 (s, 2H), 3.67-3.37 (m, 3H), 3.37-3.23 (m, 2H), 2.43 (s, 3H), 2.17-2.04 (m, 1H), 1.80 (br s, 2H).

Example 206

4-(4-Methyl-piperazin-1-yl)-6-pyridin-4-ylmethyl-pyrimidin-2-ylamine

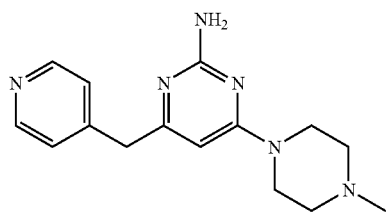

MS (ESI): mass calcd. for C$_{15}$H$_{20}$N$_6$, 284.2; m/z found, 285.2 [M+H]$^+$. $^1$H NMR (CDCl$_3$): 8.51 (dd, J=4.4, 1.6, 2H), 7.20-7.17 (m, 2H), 5.74 (s, 1H), 4.96 (s, 2H), 3.75 (s, 2H), 3.59-3.53 (m, 4H), 2.44-2.39 (m, 4H), 2.31 (s, 3H).

Example 207

4-(4-Methyl-piperazin-1-yl)-6-thiophen-3-ylmethyl-pyrimidin-2-ylamine

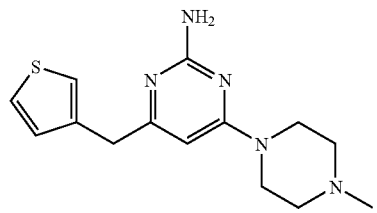

MS (ESI): mass calcd. for C$_{14}$H$_{19}$N$_5$S, 289.1; m/z found, 290.2 [M+H]$^+$. $^1$H NMR (CDCl$_3$): 7.24 (dd, J=4.9, 3.0, 1H), 7.05-7.03 (m, 1H), 6.98 (dd, J=4.9, 1.2, 1H), 5.74 (s, 1H), 5.07 (s, 2H), 3.78 (s, 2H), 3.57-3.51 (m, 4H), 2.42-2.37 (m, 4H), 2.29 (s, 3H).

Example 208

(R)-4-(3-Methylamino-pyrrolidin-1-yl)-6-thiophen-3-ylmethyl-pyrimidin-2-ylamine

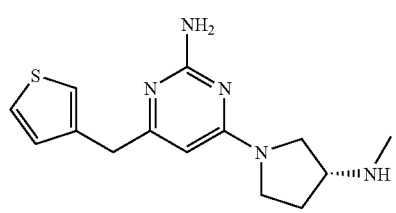

MS (ESI): mass calcd. for C$_{14}$H$_{19}$N$_5$S, 289.1; m/z found, 290.2 [M+H]$^+$. $^1$H NMR (CDCl$_3$): 7.21 (dd, J=4.9, 3.0, 1H), 7.03-7.00 (m, 1H), 6.96 (dd, J=4.9, 1.2, 1H), 5.50 (s, 1H), 5.47 (s, 2H), 3.74 (s, 2H), 3.63-3.32 (m, 4H), 3.29-3.15 (m, 2H), 2.40 (s, 3H), 2.09-2.00 (m, 1H), 1.80-1.67 (m, 1H).

Example 209

4-Piperazin-1-yl-6-thiophen-3-ylmethyl-pyrimidin-2-ylamine

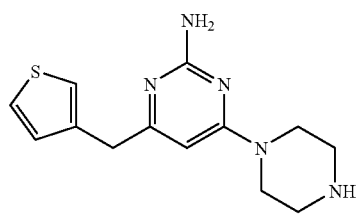

MS (ESI): mass calcd. for C$_{13}$H$_{17}$N$_5$S, 275.1; m/z found, 276.1 [M+H]$^+$. $^1$H NMR (CDCl$_3$): 7.30-7.26 (m, 1H), 7.10-7.04 (m, 1H), 6.97 (d, J=4.5, 1H), 5.78 (s, 1H), 4.44-4.29 (m, 3H), 3.77 (s, 2H), 3.57-3.49 (m, 4H), 2.94-2.80 (m, 4H).

Example 210

(R)-4-(3-Amino-pyrrolidin-1-yl)-6-thiophen-3-ylmethyl-pyrimidin-2-ylamine

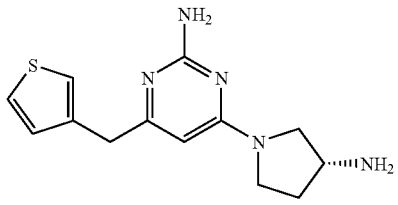

MS (ESI): mass calcd. for C$_{13}$H$_{17}$N$_5$S, 275.1; m/z found, 276.2 [M+H]$^+$. $^1$H NMR (CDCl$_3$): 7.26-7.21 (m, 1H), 7.04 (s, 1H), 6.98 (d, J=4.6, 1H), 5.52 (s, 1H), 5.16 (s, 2H), 3.77 (s, 2H), 3.65-3.57 (m, 2H), 3.53-2.85 (m, 3H), 2.19-1.95 (m, 1H), 1.76-1.65 (m, 1H), 1.63-1.42 (m, 2H).

Example 211

4-(cis-Octahydro-pyrrolo[3,4-b]pyridin-6-yl)-6-thiophen-3-ylmethyl-pyrimidin-2-ylamine

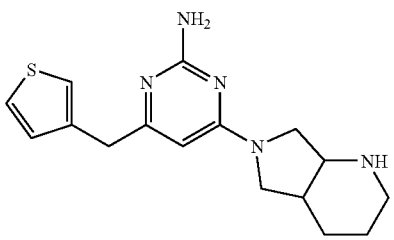

MS (ESI): mass calcd. for C$_{16}$H$_{21}$N$_5$S, 315.2; m/z found, 316.2 [M+H]$^+$. $^1$H NMR (CDCl$_3$): 7.24 (dd, J=4.9, 3.0, 1H), 7.07-7.03 (m, 1H), 6.98 (d, J=4.7, 1H), 5.58-5.47 (m, 1H), 5.13 (s, 2H), 3.77 (s, 2H), 3.67-3.06 (m, 6H), 3.01-2.88 (m, 1H), 2.66-2.58 (m, 1H), 2.35-2.15 (m, 1H), 1.74-1.52 (m, 3H), 1.50-1.41 (m, 1H).

Example 212

N$^4$-(2-Amino-ethyl)-6-thiophen-3-ylmethyl-pyrimidine-2,4-diamine

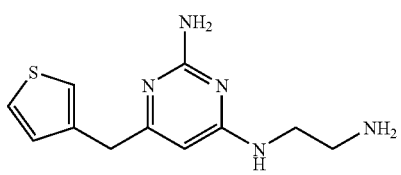

MS (ESI): mass calcd. for C$_{11}$H$_{15}$N$_5$S, 249.1; m/z found, 250.1 [M+H]$^+$. $^1$H NMR (CDCl$_3$): 7.23 (dd, J=4.9, 3.0, 1H), 7.04-7.01 (m, 1H), 6.95 (dd, J=4.9, 1.15, 1H), 5.94-5.67 (m, 1H), 5.52 (s, 1H), 5.33 (s, 2H), 3.74 (s, 2H), 3.33-3.20 (m, 2H), 2.81 (t, J=5.8, 2H), 1.72-1.58 (m, 2H).

Example 213

4-(4-Methyl-piperazin-1-yl)-6-thiophen-2-ylmethyl-pyrimidin-2-ylamine

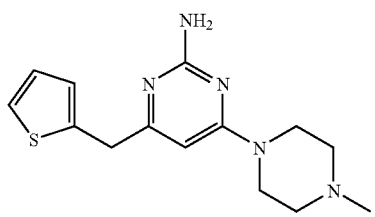

MS (ESI): mass calcd. for C$_{14}$H$_{19}$N$_5$S, 289.1; m/z found, 290.2 [M+H]$^+$. $^1$H NMR (CDCl$_3$): 7.13 (dd, J=5.1, 1.2, 1H), 6.90 (dd, J=5.1, 3.4, 1H), 6.88-6.85 (m, 1H), 5.79 (s, 1H), 5.41 (s, 2H), 3.93 (s, 2H), 3.55-3.50 (m, 4H), 2.38-2.34 (m, 4H), 2.26 (s, 3H).

Example 214

(R)-4-(3-Methylamino-pyrrolidin-1-yl)-6-thiophen-2-ylmethyl-pyrimidin-2-ylamine

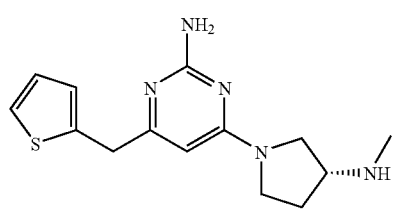

MS (ESI): mass calcd. for C$_{14}$H$_{19}$N$_5$S, 289.1; m/z found, 290.2 [M+H]$^+$. $^1$H NMR (CDCl$_3$): 7.11 (dd, J=5.1, 1.2, 1H), 6.89 (dd, J=5.1, 3.4, 1H), 6.87-6.85 (m, 1H), 5.56 (s, 1H), 5.54 (s, 2H), 3.91 (s, 2H), 3.74-2.64 (m, 6H), 2.38 (s, 3H), 2.08-1.98 (m, 1H), 1.78-1.66 (m, 1H).

Example 215

4-Piperazin-1-yl-6-thiophen-2-ylmethyl-pyrimidin-2-ylamine

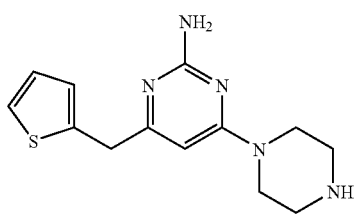

MS (ESI): mass calcd. for C$_{13}$H$_{17}$N$_5$S, 275.1; m/z found, 276.1 [M+H]$^+$. $^1$H NMR (CDCl$_3$): 7.18 (dd, J=5.1, 1.2, 1H), 6.94 (dd, J=5.1, 3.4, 1H), 6.91-6.89 (m, 1H), 5.85 (s, 1H), 4.57 (s, 3H), 3.94 (s, 2H), 3.55-3.51 (m, 4H), 2.86-2.82 (m, 4H).

Example 216

(R)-4-(3-Amino-pyrrolidin-1-yl)-6-thiophen-2-ylmethyl-pyrimidin-2-ylamine

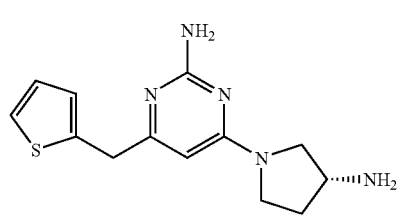

MS (ESI): mass calcd. for C$_{13}$H$_{17}$N$_5$S, 275.1; m/z found, 276.1 [M+H]$^+$. $^1$H NMR (CDCl$_3$): 7.13 (dd, J=5.1, 1.2, 1H), 6.91 (dd, J=5.1, 3.4, 1H), 6.88-6.86 (m, 1H), 5.57 (s, 1H), 5.39 (s, 2H), 3.93 (s, 2H), 3.85-3.01 (m, 6H), 2.15-1.99 (m, 1H), 1.79-1.23 (m, 2H).

Example 217

4-(cis-Octahydro-pyrrolo[3,4-b]pyridin-6-yl)-6-thiophen-2-ylmethyl-pyrimidin-2-ylamine

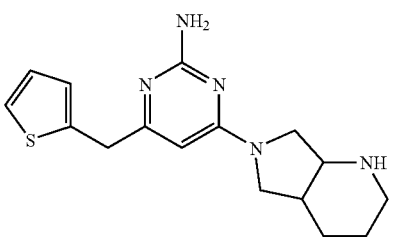

MS (ESI): mass calcd. for $C_{16}H_{21}N_5S$, 315.2; m/z found, 316.2 [M+H]$^+$. $^1$H NMR (CDCl$_3$): 7.14 (dd, J=5.1, 1.1, 1H), 6.92 (dd, J=5.0, 3.5, 1H), 6.89-6.87 (m, 1H), 5.64-5.54 (m, 1H), 5.10 (s, 2H), 3.94 (s, 2H), 3.66-3.08 (m, 5H), 3.02-2.90 (m, 1H), 2.67-2.56 (m, 1H), 2.34-2.15 (m, 1H), 1.77-1.51 (m, 4H), 1.49-1.40 (m, 1H).

Example 218

N$^4$-(2-Amino-ethyl)-6-thiophen-2-ylmethyl-pyrimidine-2,4-diamine

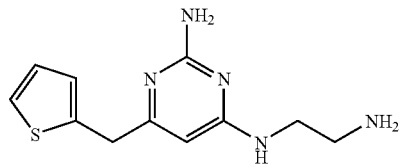

MS (ESI): mass calcd. for $C_{11}H_{15}N_5S$, 249.1; m/z found, 250.1 [M+H]$^+$. $^1$H NMR (CDCl$_3$): 7.19 (dd, J=5.1, 1.1, 1H), 6.93 (dd, J=5.1, 3.5, 1H), 6.90-6.88 (m, 1H), 5.71 (s, 1H), 4.76 (s, 5H), 3.89 (s, 2H), 3.41-3.31 (m, 2H), 2.81 (t, J=6.0, 2H).

Example 219

N$^4$-(2-Amino-ethyl)-6-methoxymethyl-pyrimidine-2,4-diamine

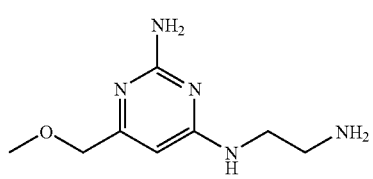

MS (ESI): mass calcd. for $C_8H_{15}N_5O$, 197.1; m/z found, 198.1 [M+H]$^+$.

Example 220

4-(3-Amino-azetidin-1-yl)-6-methoxymethyl-pyrimidin-2-ylamine

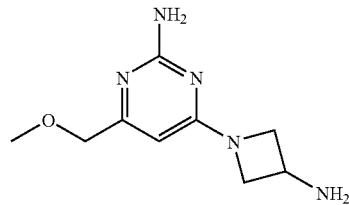

MS (ESI): mass calcd. for $C_9H_{15}N_5O$, 209.1; m/z found, 210.1 [M+H]$^+$. $^1$H NMR (MeOD): 5.77 (s, 1H), 4.25 (t, J=8.2, 2H), 4.18-4.15 (m, 2H), 3.95-3.85 (m, 1H), 3.76-3.68 (m, 2H), 3.41 (s, 3H).

Example 221

(R)-4-Methoxymethyl-6-(3-methylamino-pyrrolidin-1-yl)-pyrimidin-2-ylamine

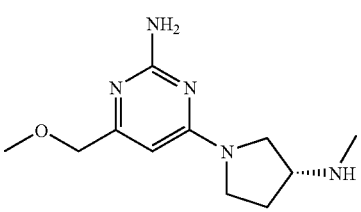

MS (ESI): mass calcd. for $C_{11}H_{19}N_5O$, 237.2; m/z found, 238.1 [M+H]$^+$. $^1$H NMR (MeOD): 5.92 (s, 1H), 4.23-4.15 (m, 2H), 3.84-3.44 (m, 3H), 3.42 (s, 3H), 3.38-3.25 (m, 2H), 2.40 (s, 3H), 2.28-2.13 (m, 1H), 1.96-1.78 (m, 1H).

Example 222

(R)-4-(3-Amino-pyrrolidin-1-yl)-6-methoxymethyl-pyrimidin-2-ylamine

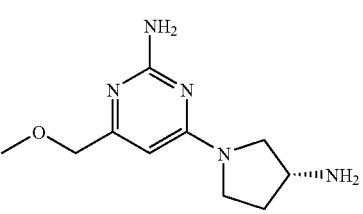

MS (ESI): mass calcd. for $C_{10}H_{17}N_5O$, 223.1; m/z found, 224.1 [M+H]$^+$. $^1$H NMR (MeOD): 6.10 (s, 1H), 4.31 (s, 2H), 3.99 (s, 1H), 3.91-3.81 (m, 1H), 3.80-3.57 (m, 3H), 3.45 (s, 3H), 2.53-2.35 (m, 1H), 2.21-2.09 (m, 1H).

Example 223

4-Methoxymethyl-6-(4-methyl-piperazin-1-yl)-pyrimidin-2-ylamine

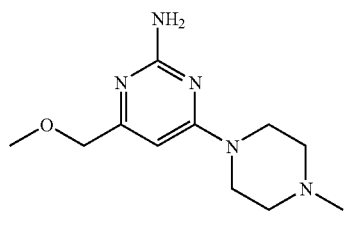

MS (ESI): mass calcd. for C$_{11}$H$_{19}$N$_5$O, 237.2; m/z found, 238.1 [M+H]$^+$. $^1$H NMR (MeOD): 6.15 (s, 1H), 4.19-4.18 (m, 2H), 3.67-3.62 (m, 4H), 3.41 (s, 3H), 2.51-2.41 (m, 4H), 2.31 (s, 3H).

Example 224

4-Methoxymethyl-6-piperazin-1-yl-pyrimidin-2-ylamine

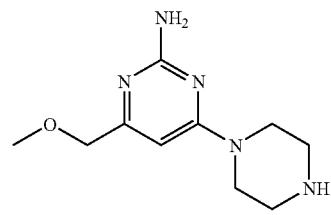

MS (ESI): mass calcd. for C$_{10}$H$_{17}$N$_5$O, 223.1; m/z found, 224.1 [M+H]$^+$. $^1$H NMR (MeOD): 6.13 (s, 1H), 4.19 (s, 2H), 3.64-3.55 (m, 4H), 3.41 (s, 3H), 2.89-2.79 (m, 4H).

Example 225

(R)-4-(3-Amino-piperidin-1-yl)-6-methoxymethyl-pyrimidin-2-ylamine

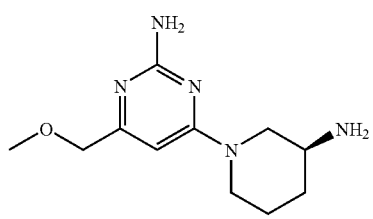

MS (ESI): mass calcd. for C$_{11}$H$_{19}$N$_5$O, 237.2; m/z found, 238.1 [M+H]$^+$. $^1$H NMR (MeOD): 6.17 (s, 1H), 4.31-4.24 (m, 1H), 4.18 (s, 2H), 4.15-4.07 (m, 1H), 3.42 (s, 3H), 3.06-2.97 (m, 1H), 2.90-2.76 (m, 2H), 2.06-1.95 (m, 1H), 1.82-1.71 (m, 1H), 1.58-1.36 (m, 2H).

Example 226

(R,R)-4-Methoxymethyl-6-(octahydro-pyrrolo[3,4-b]pyridin-6-yl)-pyrimidin-2-ylamine

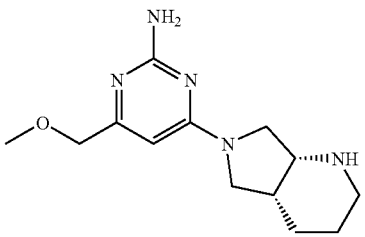

MS (ESI): mass calcd. for C$_{13}$H$_{21}$N$_5$O, 263.2; m/z found, 264.1 [M+H]$^+$. $^1$H NMR (MeOD): 5.94 (s, 1H), 4.19 (s, 2H), 3.72-3.47 (m, 3H), 3.42 (s, 4H), 3.01-2.89 (m, 1H), 2.72-2.61 (m, 2H), 2.54-2.32 (m, 1H), 1.88-1.73 (m, 2H), 1.72-1.58 (m, 1H), 1.56-1.46 (m, 1H).

Example 227

4-(4-Methyl-piperazin-1-yl)-6-(tetrahydro-furan-2-ylmethyl)-pyrimidin-2-ylamine

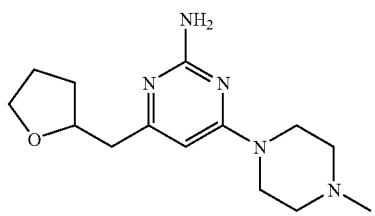

MS (ESI): mass calcd. for C$_{14}$H$_{23}$N$_5$O, 277.2; m/z found, 278.2 [M+H]$^+$. $^1$H NMR (CDCl$_3$): 5.90 (s, 1H), 4.75 (br s, 2H), 4.21 (app p, J=6.4, 1H), 3.90 (dd, J=14.6, 7.2, 1H), 3.74 (dd, J=14.2, 7.9, 1H), 3.60 (t, J=5.0, 4H), 2.64 (dq, J=13.6, 6.4, 2H), 2.42 (t, J=5.1, 4H), 2.3 (s, 3H), 2.05-1.98 (m, 1H), 1.92-1.80 (m, 2H), 1.63-1.52 (m, 1H).

Example 228

(R)-4-(3-Methylamino-pyrrolidin-1-yl)-6-(tetrahydro-furan-2-ylmethyl)-pyrimidin-2-ylamine

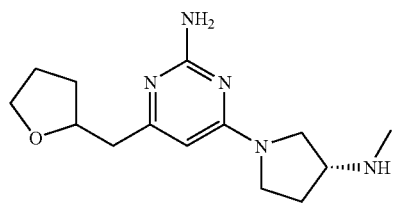

MS (ESI): mass calcd. for $C_{14}H_{23}N_5O$, 277.2; m/z found, 278.2 [M+H]$^+$. $^1$H NMR (CDCl$_3$): 5.70 (s, 1H), 4.75 (br s, 2H), 4.20 (app p, J=6.4, 1H), 3.88 (dd, J=14.6, 7.2, 1H), 3.72 (dd, J=14.2, 7.9, 1H), 3.70-3.20 (m, 5H), 2.64 (ddd, J=19.0, 13.5, 6.5, 2H), 2.42 (s, 3H), 2.18-2.08 (m, 1H), 2.05-1.80 (m, 5H), 1.63-1.52 (m, 1H).

Example 229

4-(cis-5-Methyl-hexahydro-pyrrolo[3,4-c]pyrrol-2-yl)-6-(tetrahydro-furan-2-ylmethyl)-pyrimidin-2-ylamine

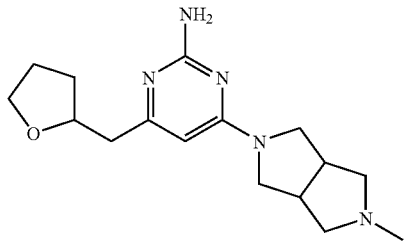

MS (ESI): mass calcd. for $C_{16}H_{25}N_5O$, 303.2; m/z found, 304.2 [M+H]$^+$. $^1$H NMR (CDCl$_3$): 5.70 (s, 1H), 4.80 (br s, 2H), 4.20 (app p, J=6.4, 1H), 3.90 (dd, J=14.2, 7.7, 1H); 3.72 (dd, J=14.2, 7.9, 1H), 3.65-3.55 (m, 2H), 3.40-3.30 (m, 2H), 2.98-2.90 (m, 2H), 2.72-2.55 (m, 3H), 2.42-2.40 (m, 3H), 2.32 (s, 3H), 2.05-1.80 (m, 3H), 1.63-1.52 (m, 1H).

Example 230

4-Piperazin-1-yl-6-(tetrahydro-furan-2-ylmethyl)-pyrimidin-2-ylamine

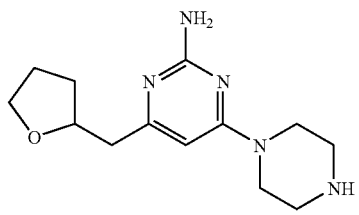

MS (ESI): mass calcd. for $C_{13}H_{21}N_5O$, 263.2; m/z found, 264.2 [M+H]$^+$. $^1$H NMR (CDCl$_3$): 5.90 (s, 1H), 4.72 (br s, 2H), 4.22 (app p, J=6.4, 1H), 3.90 (dd, J=14.6, 7.2, 1H), 3.73 (dd, J=14.2, 7.9, 1H), 3.55 (t, J=5.1, 4H), 2.90 (t, J=5.1, 4H), 2.63 (dq, J=13.6, 6.4, 2H), 2.05-1.80 (m, 3H), 1.63-1.55 (m, 1H).

Example 231

4-(cis-Octahydro-pyrrolo[3,4-b]pyridin-6-yl)-6-(tetrahydro-furan-2-ylmethyl)-pyrimidin-2-ylamine

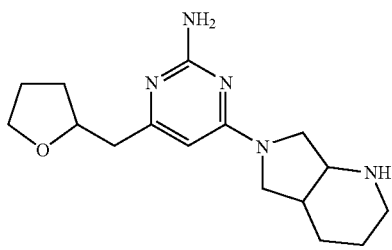

MS (ESI): mass calcd. for $C_{16}H_{25}N_5O$, 303.2; m/z found, 304.2 [M+H]$^+$. $^1$H NMR (CDCl$_3$): 5.70 (br s, 1H), 4.75 (br s, 2H), 4.22 (app p, J=6.4, 1H), 3.90 (dd, J=14.6, 7.2, 1H), 3.73 (dd, J=14.2, 7.9, 1H), 3.55-3.30 (m, 5H), 2.99 (td, J=11.8, 3.4, 1H), 2.70-2.58 (m, 3H), 2.40-2.20 (m, 1H), 2.05-1.40 (m, 8H).

Example 232

4-(4-Chloro-benzyl)-6-(4-methyl-piperazin-1-yl)-pyrimidin-2-ylamine

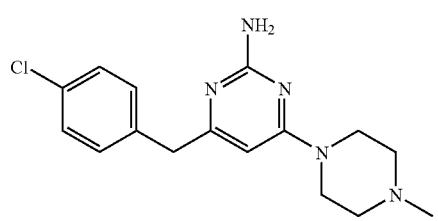

MS (ESI): mass calcd. for $C_{16}H_{20}ClN_5$, 317.1; m/z found, 318.1 [M+H]$^+$. $^1$H NMR (CDCl$_3$): 7.29-7.23 (m, 2H), 7.21-7.16 (m, 2H), 5.70 (s, 1H), 3.74 (s, 2H), 3.57-3.52 (m, 4H), 2.43-2.39 (m, 4H), 2.31 (s, 3H), 1.92-1.85 (m, 2H)

Example 233

4-(4-Chloro-benzyl)-6-piperazin-1-yl-pyrimidin-2-ylamine

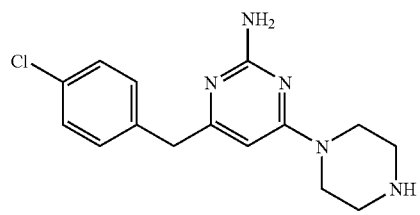

MS (ESI): mass calcd. for $C_{15}H_{18}ClN_5$, 303.13; m/z found, 304.1 [M+H]$^+$. $^1$H NMR (MeOD): 7.42-7.36 (m, 2H), 7.35-7.30 (m, 2H), 6.49 (s, 1H), 4.22 (s, 2H), 3.55-3.52 (m, 4H), 3.39-3.33 (m, 4H)

Example 234

(R)-4-(4-Chloro-benzyl)-6-(3-methylamino-pyrrolidin-1-yl)-pyrimidin-2-ylamine

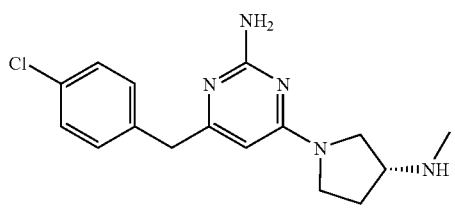

MS (ESI): mass calcd. for $C_{16}H_{20}ClN_5$, 317.1; m/z found, 318.1 [M+H]$^+$. $^1$H NMR (MeOD): 7.30-7.19 (m, 4H), 5.70 (s, 1H), 3.72 (s, 2H), 3.69-3.32 (m, 5H), 2.42 (s, 3H), 2.26-2.13 (m, 1H), 1.93-1.80 (m, 1H).

Example 235

(R)-4-(3-Amino-pyrrolidin-1-yl)-6-(4-chloro-benzyl)-pyrimidin-2-ylamine

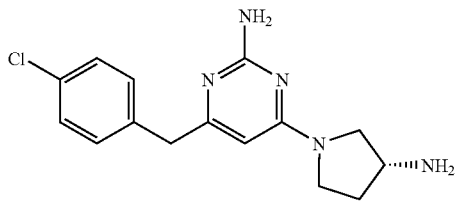

MS (ESI): mass calcd. for $C_{15}H_{18}ClN_5$, 303.79; m/z found, 304.1 [M+H]$^+$.

Example 236

4-(4-Chloro-benzyl)-6-(cis-5-methyl-hexahydro-pyrrolo[3,4-c]pyrrol-2-yl)-pyrimidin-2-ylamine

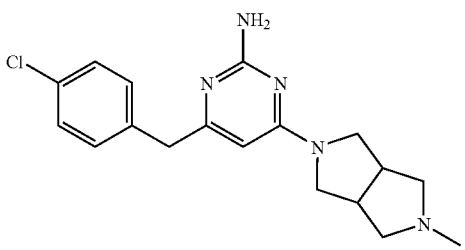

MS (ESI): mass calcd. for $C_{18}H_{22}ClN_5$, 343.14; m/z found, 344.1 [M+H]$^+$.

Example 237

4-(4-Chloro-benzyl)-6-(cis-hexahydro-pyrrolo[3,4-c]pyrrol-2-yl)-pyrimidin-2-ylamine

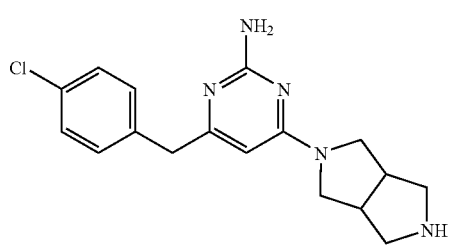

MS (ESI): mass calcd. for $C_{17}H_{20}ClN_5$, 329.14; m/z found, 330.1 [M+H]$^+$.

Example 238

N$^4$-(2-Amino-ethyl)-6-(4-chloro-benzyl)-N$^4$-methyl-pyrimidine-2,4-diamine

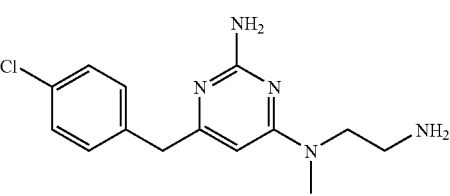

MS (ESI): mass calcd. for $C_{14}H_{18}ClN_5$, 291.13; m/z found, 292.1 [M+H]$^+$.

Example 239

4-Ethyoxymethyl-6-(4-methyl-piperazin-1-yl)-pyrimidin-2-ylamine

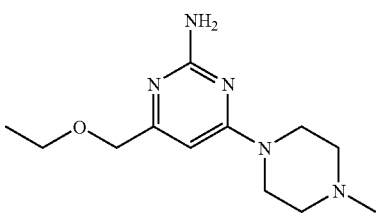

MS (ESI): mass calcd. for $C_{12}H_{21}N_5O$, 251.3; m/z found, 252.2 [M+H]$^+$. $^1$H NMR (MeOD): 6.53 (s, 1H), 4.47 (s, 2H), 4.46-3.70 (m, 4H), 3.64 (q, J=7.0, 2H), 3.47-3.40 (m, 4H), 2.96 (s, 3H), 1.28 (t, J=7.0, 3H).

Example 240

4-Ethoxymethyl-6-piperazin-1-yl-pyrimidin-2-ylamine

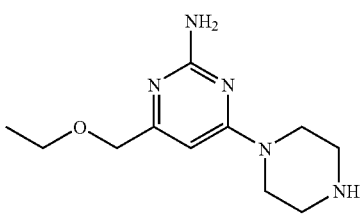

MS (ESI): mass calcd. for $C_{11}H_{19}N_5O$, 237.3; m/z found, 238.2 [M+H]$^+$. $^1$H NMR (MeOD): 6.54 (s, 1H), 4.48 (s, 2H), 4.40-3.91 (m, 4H), 3.64 (q, J=7.0, 2H), 3.60 (m, 4H), 1.27 (t, J=7.0, 3H).

Example 241

(R)-Ethoxymethyl-6-(3-methylamino-pyrrolidin-1-yl)-pyrimidin-2-ylamine

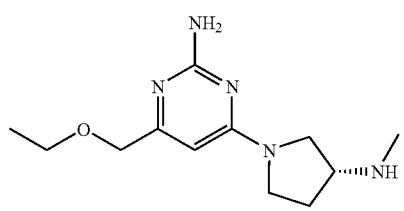

MS (ESI): mass calcd. for $C_{12}H_{21}N_5O$, 251.3; m/z found, 252.2 [M+H]$^+$. $^1$H NMR (MeOD): 6.22 (s, 1H), 4.46 (s, 2H), 4.03-3.88 (m, 3H), 3.82 (m, 1H), 3.74 (m, 0.5H), 3.64 (m, 2H), 3.58-3.39 (m, 0.5H), 2.79 (m, 3H), 2.61-2.19 (m, 2H), 1.28 (t, J=7.0, 3H).

Example 242

(R)-Ethoxymethyl-6-(3-amino-pyrrolidin-1-yl)-pyrimidin-2-ylamine

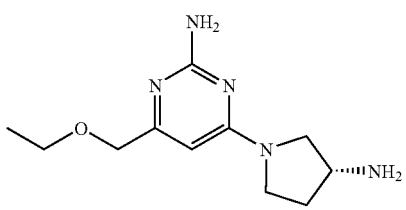

MS (ESI): mass calcd. for $C_{11}H_{19}N_5O$, 237.3; m/z found, 238.2 [M+H]$^+$. $^1$H NMR (MeOD): 6.27 (m, 1H), 4.49 (s, 2H), 4.10 (m, 1H), 3.98 (m, 1H), 3.93-3.70 (m, 3H), 3.66 (s, 1H), 3.65 (q, J=7.0, 2H), 2.55 (m, 1H), 2.28 (m, 1H), 1.28 (t, J=7.0, 3H).

Example 243

Isopropoxymethyl-6-((R)-3-methylamino-pyrrolidin-1-yl)-pyrimidin-2-ylamine

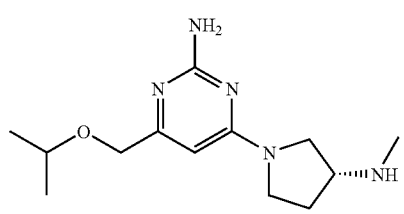

MS (ESI): mass calcd. for $C_{13}H_{23}N_5O$, 265.4; m/z found, 266.3 [M+H]$^+$. $^1$H NMR (MeOD): 6.27 (m, 1H), 4.50 (s, 2H), 4.00 (m, 3H), 3.79 (m, 3H), 3.66 (s, 2H), 2.79 (m, 3H), 2.63-2.22 (m, 2H), 1.25 (m, 6H).

Example 244

4-Isopropoxymethyl-6-piperazin-1-yl-pyrimidin-2-ylamine

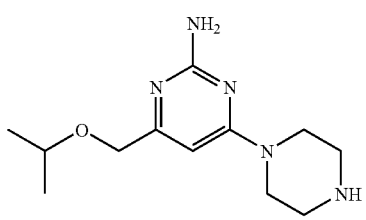

MS (ESI): mass calcd. for $C_{12}H_{21}N_5O$, 251.3; m/z found, 252.2 [M+H]$^+$. $^1$H NMR (MeOD): 5.94 (s, 1H), 4.23 (s, 2H), 3.68 (quintet, J=6.1, 1H), 3.62 (m, 4H), 3.56-3.32 (m, 1H), 3.25-2.90 (m, 1H), 2.50-2.15 (m, 1H), 1.91-1.75 (m, 1H), 1.21 (m, 6H).

Example 245

(R)-Isopropoxymethyl-6-(3-amino-pyrrolidin-1-yl)-pyrimidin-2-ylamine

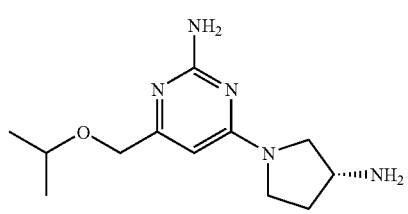

MS (ESI): mass calcd. for $C_{12}H_{21}N_5O$, 251.3; m/z found, 252.2 [M+H]$^+$. $^1$H NMR (MeOD): 6.16 (s, 1H), 4.24 (s, 2H), 3.68 (quintet, J=6.1, 1H), 3.66-3.58 (m, 4H), 3.49-3.38 (m, 1H), 2.82 (m, 4H), 1.23 (m, 6H).

Example 246

4-Isopropoxymethyl-6-(4-methyl-piperazin-1-yl)-pyrimidin-2-ylamine

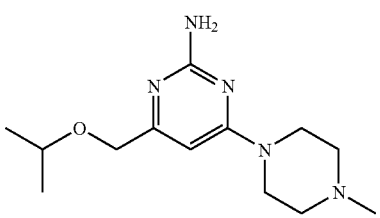

To a solution of 2-amino-6-isopropoxymethyl-3H-pyrimidin-4-one (0.050 g, 0.27 mmol) in acetonitrile (2.37 mL) was added benzotriazol-1-yloxytris(dimethylamino)phosphonium hexafluorophosphate (0.157 g, 0.355 mmol), DBU (0.82 mL, 0.55 mmol), and 1-methyl-piperazine (0.091 ml, 0.82 mmol). The reaction mixture was stirred at rt for 12 h, then at 60° C. for 3 h. The mixture was concentrated and the resultant residue was purified (2 M NH$_3$ in MeOH/CH$_2$Cl$_2$) to yield a white solid (10 mg, 14%). MS (ESI): mass calcd. for C$_{13}$H$_{23}$N$_5$O, 265.4; m/z found, 266.3 [M+H]$^+$. $^1$H NMR (MeOD): 6.55 (s, 1H), 4.49 (s, 2H), 3.78 (quintet, J=6.1, 1H), 3.70-3.00 (m, 8H), 2.95 (s, 3H), 1.25 (d, J=6.1, 6H).

Example 247

4-Phenethyl-6-piperazin-1-yl-pyrimidin-2-ylamine

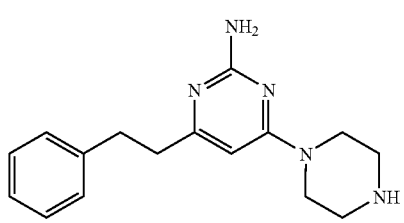

MS (ESI): mass calcd. for C$_{16}$H$_{21}$N$_5$, 283.18; m/z found, 284.2 [M+H]$^+$.

Example 248

4-(3-Amino-azetidin-1-yl)-6-phenethyl-pyrimidin-2-ylamine

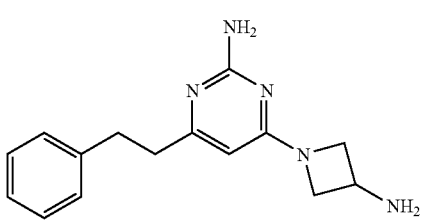

MS (ESI): mass calcd. for C$_{15}$H$_{19}$N$_5$, 269.16; found, 270.2 [M+H]$^+$.

Example 249

(R)-4-(3-Amino-pyrrolidin-1-yl)-6-(tetrahydro-pyran-4-yl)-pyrimidin-2-ylamine

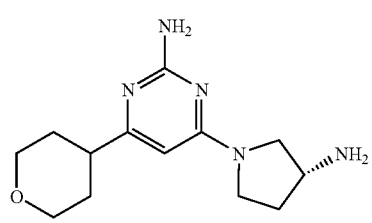

MS (ESI): mass calcd. for C$_{13}$H$_{21}$N$_5$O, 263.17; found, 264.2 [M+H]$^+$.

Example 250

N$^4$-(2-Amino-ethyl)-6-benzyl-N$^4$-methyl-pyrimidine-2,4-diamine

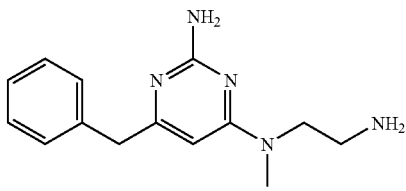

MS (ESI): mass calcd. for C$_{14}$H$_{19}$N$_5$, 257.1; found, 258.2 [M+H]$^+$.

Example 251

4-Indan-2-yl-6-(octahydro-pyrrolo[3,4-b]pyridin-6-yl)-pyrimidin-2-ylamine

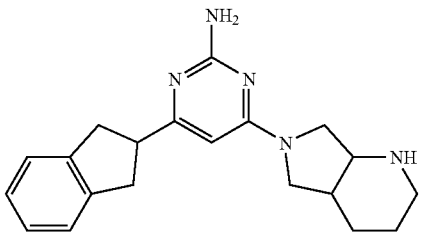

MS (ESI): mass calcd. for C$_{20}$H$_{25}$N$_5$, 335.21; found, 336.2 [M+H]$^+$.

Example 252

4-(3-Amino-azetidin-1-yl)-7,8-dihydro-5H-pyrano[4,3-d]pyrimidin-2-ylamine

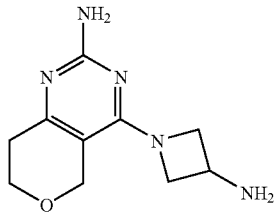

MS (ESI): mass calcd. for C$_{10}$H$_{15}$N$_5$O, 221.1; m/z found, 222.2 [M+H]$^+$.

Example 253

4-(3-Amino-azetidin-1-yl)-5,6,7,8-tetrahydro-quinazolin-2-ylamine

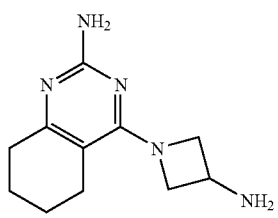

MS (ESI): mass calcd. for C$_{11}$H$_{17}$N$_5$, 219.2; m/z found, 220.2 [M+H]$^+$.

Example 254

4-(cis-5-Methyl-hexahydro-pyrrolo[3,4-c]pyrrol-2-yl)-7,8-dihydro-5H-pyrano[4,3-d]pyrimidin-2-ylamine

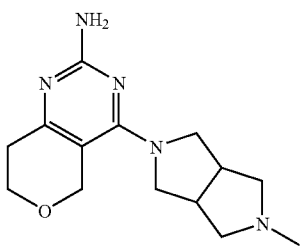

MS (ESI): mass calcd. for $C_{14}H_{21}N_5O$, 275.2; m/z found, 276.3 [M+H].

The compounds in Examples 255-256 were obtained by preparative supercritical fluid chromatography (SFC) of Example 160 by preparative HPLC using a Kromasil Cellucoat 5 micron 250×21.2 (L×I.D.) column, a mobile phase of 15% MeOH with 0.2% isopropylamine and 85% $CO_2$, a flow rate of 40 mL/min, and a back pressure of 150 bar.

Example 255

(R)-4-(3-Methylamino-pyrrolidin-1-yl)-6-(trans-2-phenyl-cyclopropyl)-pyrimidin-2-ylamine (diastereomer 1)

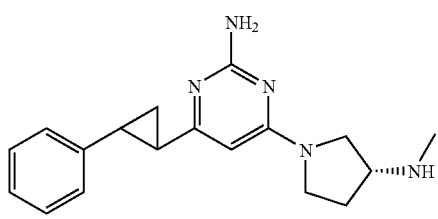

SFC: $R_t$=19.9 min. MS (ESI): mass calcd. for $C_{18}H_{23}N_5$, 309.20; found, 310.2 [M+H]$^+$.

Example 256

(R)-4-(3-Methylamino-pyrrolidin-1-yl)-6-(trans-2-phenyl-cyclopropyl)-pyrimidin-2-ylamine (diastereomer 2)

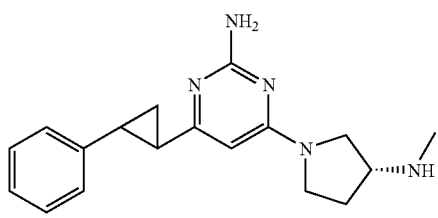

SFC: $R_t$=23.0 min. MS (ESI): mass calcd. for $C_{18}H_{23}N_5$, 309.20; found, 310.2 [M+H]$^+$.

The compounds in Examples 257-258 were obtained by preparative supercritical fluid chromatography of Example 84 using a Chiralpak AD-H 250×21 mm (L×I.D.) column at 25° C., a mobile phase of 6.25 mL/min MeOH with 0.2% TEA and 25 g/min $CO_2$, a back pressure of 150 bar, and UV detection at 214 nm.

Example 257

4-Cyclopentyl-6-(cis-1,7-diaza-spiro[4.4]non-7-yl)-pyrimidin-2-ylamine (enantiomer 1)

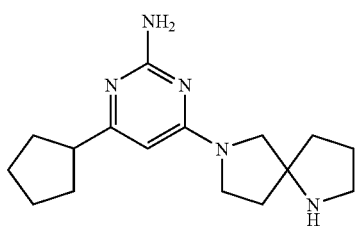

HPLC: $R_t$ = 8.9 min.

Example 258

4-Cyclopentyl-6-(cis-1,7-diaza-spiro[4.4]non-7-yl)-pyrimidin-2-ylamine (enantiomer 2)

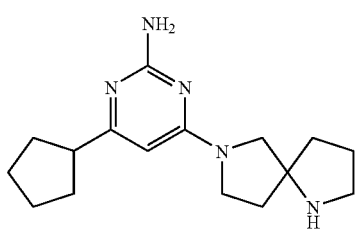

HPLC: $R_t$ = 14.8 min.

The compounds in Examples 259-280 may be prepared using methods analogous to those described for the preceding examples.

Example 259

(R)-4-Isopropoxymethyl-6-(3-methylamino-pyrrolidin-1-yl)-pyrimidin-2-ylamine

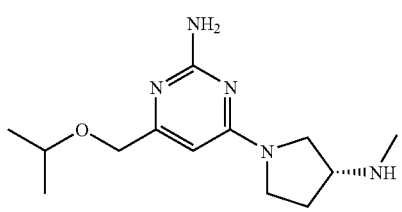

Example 260

(R)-4-(3-Amino-pyrrolidin-1-yl)-6-isopropoxym-
ethyl-pyrimidin-2-ylamine

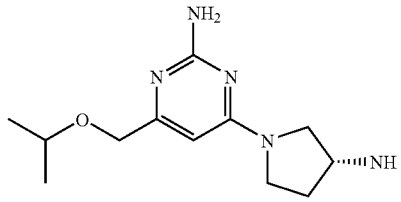

Example 261

4-Isopropoxymethyl-6-piperazin-1-yl-pyrimidin-2-
ylamine

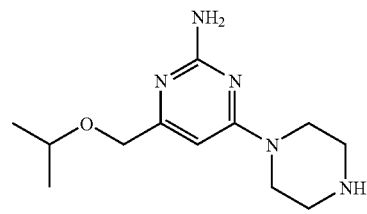

Example 262

4-Isopropoxymethyl-6-(4-methyl-piperazin-1-yl)-
pyrimidin-2-ylamine

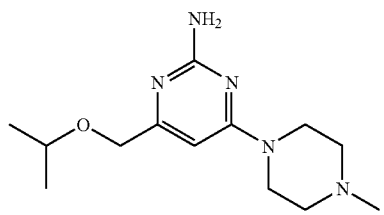

Example 263

4-(3-Amino-azetidin-1-yl)-6-isopropoxymethyl-pyri-
midin-2-ylamine

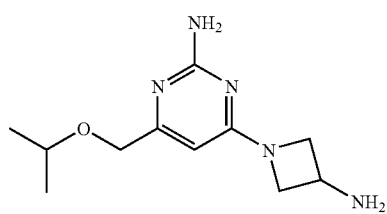

Example 264

4-Isopropoxymethyl-6-(8-methyl-3,8-diaza-bicyclo
[3.2.1]oct-3-yl)-pyrimidin-2-ylamine

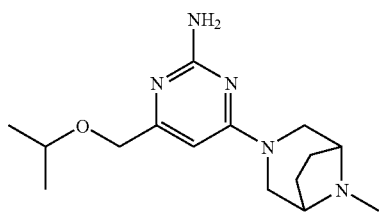

Example 265

(R)-4-Cyclopropoxymethyl-6-(3-methylamino-pyr-
rolidin-1-yl)-pyrimidin-2-ylamine

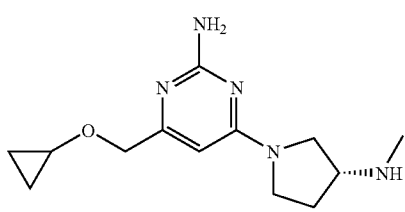

Example 266

(R)-4-(3-Amino-pyrrolidin-1-yl)-6-cyclopropoxym-
ethyl-pyrimidin-2-ylamine

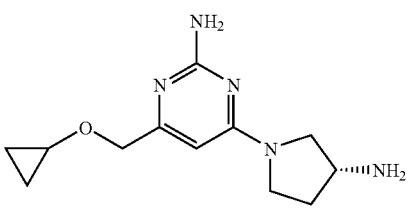

Example 267

4-Cyclopropoxymethyl-6-piperazin-1-yl-pyrimidin-
2-ylamine

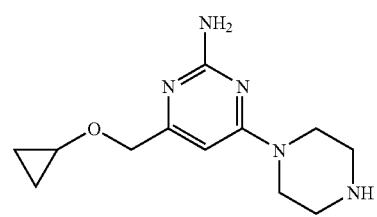

Example 268

4-Cyclopropoxymethyl-6-(4-methyl-piperazin-1-yl)-pyrimidin-2-ylamine

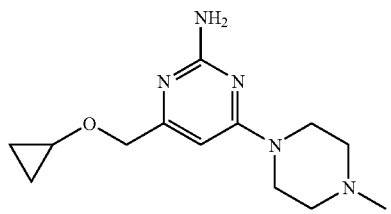

Example 269

4-(3-Amino-azetidin-1-yl)-6-cyclopropoxymethyl-pyrimidin-2-ylamine

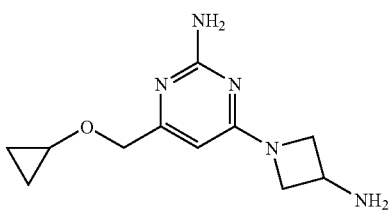

Example 270

4-Cyclopropoxymethyl-6-(8-methyl-3,8-diaza-bicyclo[3.2.1]oct-3-yl)-pyrimidin-2-ylamine

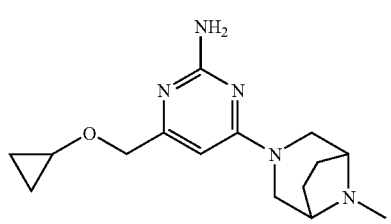

Example 271

(R)-4-tert-Butoxymethyl-6-(3-methylamino-pyrrolidin-1-yl)-pyrimidin-2-ylamine

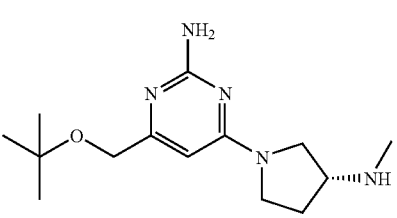

Example 272

(R)-4-(3-Amino-pyrrolidin-1-yl)-6-tert-butoxymethyl-pyrimidin-2-ylamine

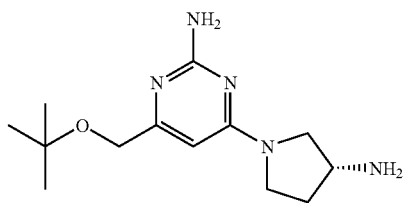

Example 273

4-tert-Butoxymethyl-6-piperazin-1-yl-pyrimidin-2-ylamine

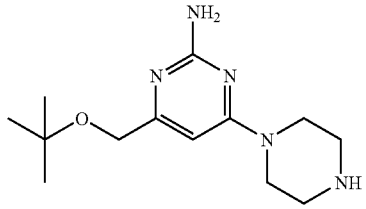

Example 274

4-tert-Butoxymethyl-6-(4-methyl-piperazin-1-yl)-pyrimidin-2-ylamine

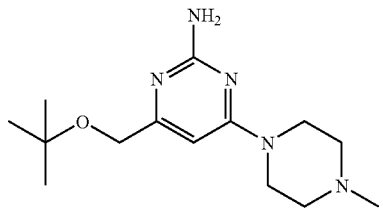

Example 275

4-(3-Amino-azetidin-1-yl)-6-tert-butoxymethyl-pyrimidin-2-ylamine

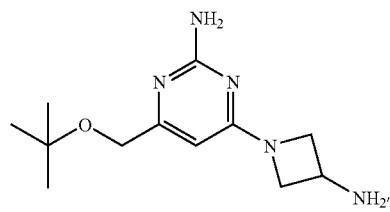

Example 276

4-tert-Butoxymethyl-6-(8-methyl-3,8-diaza-bicyclo[3.2.1]oct-3-yl)-pyrimidin-2-ylamine

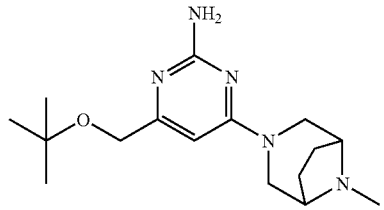

Example 277

4-Ethyl-6-(8-methyl-3,8-diaza-bicyclo[3.2.1]oct-3-yl)-pyrimidin-2-ylamine

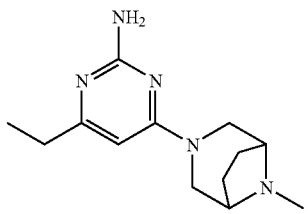

Example 278

4-(8-Methyl-3,8-diaza-bicyclo[3.2.1]oct-3-yl)-6-propyl-pyrimidin-2-ylamine

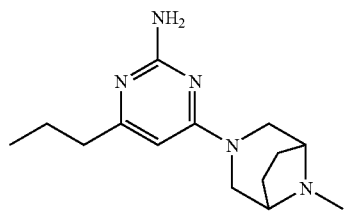

Example 279

4-Isopropyl-6-(8-methyl-3,8-diaza-bicyclo[3.2.1]oct-3-yl)-pyrimidin-2-ylamine

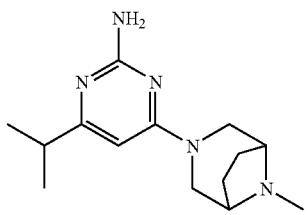

Example 280

4-Cyclopentyl-6-(8-methyl-3,8-diaza-bicyclo[3.2.1]oct-3-yl)-pyrimidin-2-ylamine

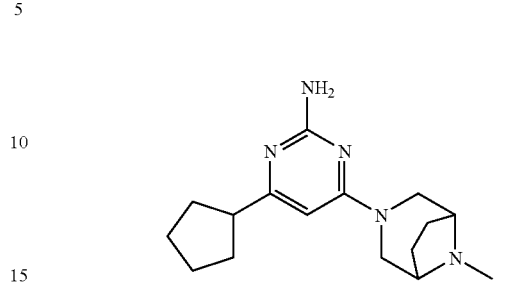

Example 281

Crystal Forms

Bis hydrochloride salts of compounds of Formula (I) were dissolved in methanol (40 mg/mL concentration) and aliquots (125 μL) were dispensed into 96-well plates. The aliquots were evaporated to leave a 5 mg sample of compound in each well. An aliquot (400 μL) of a polar or a non-polar solvent, neat or as a mixture (1:1 or 2.25:1), were added to each well. Plates were covered, sonicated, and heated to 40° C. for 15 min. Solvents were allowed to evaporate. Residual solids were analyzed for crystallinity. Crystalline forms were obtained from polar solvents, including methanol, ethanol, propanol, isopropanol, butanol, ethyl acetate, propyl acetate, butyl acetate, acetone, and 2-butanone, and aqueous mixtures thereof, and from mixtures of polar solvents, including mixtures of methanol, ethanol, propanol, isopropanol, butanol, 2-butanol, methyl acetate, ethyl acetate, propyl acetate, butyl acetate, acetone, and 2-butanone. Crystalline forms were obtained from non-polar solvents, including heptane, methyl ethyl ketone, chlorobenzene, chloroform, dichloromethane, isobutyl acetate, and toluene, and from mixtures of non-polar solvents, including mixtures of methyl tert-butyl ether, isobutyl acetate, toluene, dichlorobenzene, hexane, cyclohexane, heptane, methyl ethyl ketone, acetonitrile, pentane, THF, chloroform, and chlorobenzene.

Binding Assay on Recombinant Human Histamine $H_4$ Receptor.

Cell pellets from SK-N-MC cells stably or transiently transfected with human $H_4$ receptor were used for the binding assays. Cell pellets were homogenized in 50 mM Tris/5 mM EDTA buffer and supernatants from an 800 g spin were collected and recentrifuged at 30,000 g for 30 min. Pellets were rehomogenized in 50 mM Tris/5 mM EDTA buffer. For competition binding studies, cell membranes were incubated with $2 \times K_D$ (10 nM), [$^3$H] histamine (Specific activity: 23 $C_i$/mmol), with or without test compounds for 45 min at 25° C. Compounds were tested in free base, hydrochloride salt, or trifluoroacetic acid form. Nonspecific binding was defined with 100 μM cold histamine. $K_i$ values were calculated based on an experimentally determined appropriate $K_D$ values according to Cheng and Prusoff (*Biochem. Pharmacol.* 1973, 22(23):3099-3108). Membranes were harvested by rapid filtration using the 96 well Brandel system or a cell harvester using a Whatman GF/C filter or filter plates treated with 0.5% polyethylenimine (PEI), and washed 4 times with ice-cold 50 mM Tris/5 mM EDTA buffer. Filters were then dried, mixed with scintillant and radioactive counts were determined.

Results for the compounds tested in theses assays are presented in Tables 1 and 2 as an average of results obtained (NT=not tested). Data marked with an asterisk (*) were obtained by the cell harvester method. Where activity is shown as greater than (>) a particular value, the value is the highest concentration tested.

TABLE 1

| Ex. | $K_i$ (nM) |
| --- | --- |
| 1 | 1 |
| 2 | 1 |
| 3 | 257 |
| 4 | 1 |
| 5 | 30 |
| 6 | 6 |
| 7 | 2 |
| 8 | 3 |
| 9 | 820 |
| 10 | 159 |
| 11 | 12 |
| 12 | 18 |
| 13 | 631 |
| 14 | 673 |
| 15 | 692 |
| 16 | 65 |
| 17 | 59 |
| 18 | 17 |
| 19 | 8 |
| 20 | 18 |
| 21 | 29 |
| 22 | 18 |
| 23 | 77 |
| 24 | 49 |
| 25 | 286 |
| 26 | 177 |
| 27 | >10000 |
| 28 | 357 |
| 29 | >10000 |
| 30 | 530 |
| 31 | 249 |
| 32 | >10000 |
| 33 | 10 |
| 34 | 6 |
| 35 | 21 |
| 36 | 21 |
| 37 | 27 |
| 38 | 559 |
| 39 | 10 |
| 40 | 8 |
| 41 | 28 |
| 42 | 18 |
| 43 | 2 |
| 44 | 1 |
| 45 | 103 |
| 46 | 2 |
| 47 | 11 |
| 48 | 328 |
| 49 | 50 |
| 50 | 3 |
| 51 | 3 |
| 52 | 3 |
| 53 | 3 |
| 54 | 2 |
| 55 | 1 |
| 56 | 20 |
| 57 | 27 |
| 58 | 41 |
| 59 | 29 |
| 60 | 31 |
| 61 | 24 |
| 62 | 30 |
| 63 | 21 |
| 64 | 36 |
| 65 | 47 |
| 66 | 4 |
| 67 | 17 |
| 68 | 115 |
| 69 | 43 |

TABLE 1-continued

| Ex. | $K_i$ (nM) |
| --- | --- |
| 70 | 404 |
| 71 | 5 |
| 72 | 14 |
| 73 | >10000 |
| 74 | 76 |
| 75 | 159 |

TABLE 2

| Ex. | $K_i$ (nM) |
| --- | --- |
| 80 | 1 |
| 81 | 2 |
| 82 | 25 |
| 83 | 3 |
| 84 | 11 |
| 85 | 6 |
| 86 | 56 |
| 87 | 328 |
| 88 | 520 |
| 89 | 19 |
| 90 | 14 |
| 91 | 84 |
| 92 | 281 |
| 93 | 481 |
| 94 | 497 |
| 95 | 8* |
| 96 | 35 |
| 97 | 20 |
| 98 | 298 |
| 99 | 214 |
| 100 | 262 |
| 101 | 30 |
| 102 | 181 |
| 103 | 22* |
| 104 | 96* |
| 105 | 103 |
| 106 | 39* |
| 107 | 104 |
| 108 | 84 |
| 109 | 517* |
| 110 | 80 |
| 111 | 33 |
| 112 | 46 |
| 113 | 136 |
| 114 | 71 |
| 115 | 1431* |
| 116 | 64 |
| 117 | 42 |
| 118 | 242 |
| 119 | 153 |
| 120 | 113 |
| 121 | 3 |
| 122 | 22 |
| 123 | 4 |
| 124 | >10000 |
| 125 | 7 |
| 126 | 23 |
| 127 | 9 |
| 128 | 19 |
| 129 | 46 |
| 130 | 8 |
| 131 | 412* |
| 132 | 356* |
| 133 | 238* |
| 134 | 130 |
| 135 | 4 |
| 136 | 1 |
| 137 | 2 |
| 138 | 44 |
| 139 | 138 |
| 140 | 397 |
| 141 | 84 |
| 142 | 3 |
| 143 | 13 |

TABLE 2-continued

| Ex. | $K_i$ (nM) |
|---|---|
| 144 | 6 |
| 145 | 117 |
| 146 | 3 |
| 147 | 4 |
| 148 | 1 |
| 149 | 3 |
| 150 | 85 |
| 151 | 2 |
| 152 | 6 |
| 153 | 97 |
| 154 | 49 |
| 155 | 82 |
| 156 | 12 |
| 157 | 29 |
| 158 | 8 |
| 159 | 42 |
| 160 | 3 |
| 161 | 24 |
| 162 | 5 |
| 163 | 2 |
| 164 | 4 |
| 165 | 2 |
| 166 | 52 |
| 167 | 78 |
| 168 | 46 |
| 169 | 396 |
| 170 | 5891 |
| 171 | 106 |
| 172 | 932 |
| 173 | 2071 |
| 174 | 138 |
| 175 | 85 |
| 176 | 335 |
| 177 | 1030 |
| 178 | 9 |
| 179 | 6 |
| 180 | 8 |
| 181 | 8 |
| 182 | 20 |
| 183 | 16 |
| 184 | 13 |
| 185 | 300 |
| 186 | 213 |
| 187 | 10 |
| 188 | 18 |
| 189 | 6 |
| 190 | 11 |
| 191 | 12 |
| 192 | 17 |
| 193 | 31 |
| 194 | 49 |
| 195 | 59 |
| 196 | 203 |
| 197 | 204 |
| 198 | 2450 |
| 199 | 69 |
| 200 | 235 |
| 201 | 391 |
| 202 | 515 |
| 203 | 4230 |
| 204 | 45 |
| 205 | 230 |
| 206 | 81 |
| 207 | 2 |
| 208 | 8 |
| 209 | 2 |
| 210 | 12 |
| 211 | 4 |
| 212 | 12 |
| 213 | 4 |
| 214 | 19 |
| 215 | 6 |
| 216 | 32 |
| 217 | 9 |
| 218 | 20 |
| 219 | 890 |
| 220 | NT |
| 221 | 43 |
| 222 | 23 |
| 223 | 15 |
| 224 | 26 |
| 225 | 464 |
| 226 | 14 |
| 227 | 17 |
| 228 | 91 |
| 229 | 360 |
| 230 | 25 |
| 231 | 59 |
| 232 | 8 |
| 233 | 12 |
| 234 | 18 |
| 235 | 140 |
| 236 | 249 |
| 237 | 257 |
| 238 | 1769 |
| 239 | 29 |
| 240 | 25 |
| 241 | 31 |
| 242 | 22 |
| 243 | NT |
| 244 | NT |
| 245 | NT |
| 246 | 32 |
| 247 | 3 |
| 248 | 9 |
| 249 | 87 |
| 250 | 564* |
| 251 | 20* |
| 252 | >10000 |
| 253 | >10000 |
| 254 | >10000 |
| 255 | 34 |
| 256 | 5 |
| 257 | 31 |
| 258 | 34 |

While the invention has been illustrated by reference to examples, it is understood that the invention is intended not to be limited to the foregoing detailed description.

What is claimed is:

1. A compound of formula (I)

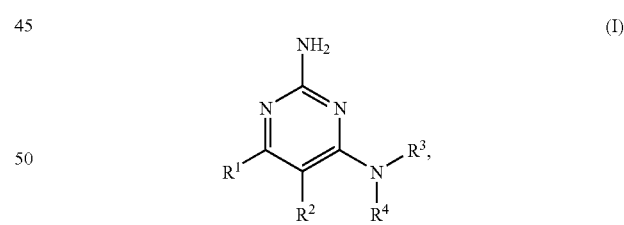

wherein —N($R^3$)$R^4$ is

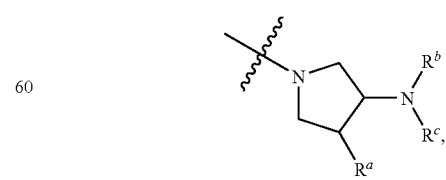

$R^2$ is H, $R^1$ is isopropyl, $R^a$ is H, and $R^b$ and $R^c$ are each H, or a pharmaceutically acceptable salt thereof.

2. The compound (S)-4-(3-Amino-pyrrolidin-1-yl)-6-isopropyl-pyrimidin-2-ylamine or a pharmaceutically acceptable salt thereof.

3. The compound (R)-4-(3-Amino-pyrrolidin-1-yl)-6-isopropyl-pyrimidin-2-ylamine or a pharmaceutically acceptable salt thereof.

4. A pharmaceutical composition comprising an effective amount of a compound of formula (I) according to claim 1 or a pharmaceutically acceptable salt thereof and a pharmaceutically acceptable carrier.

5. A pharmaceutical composition according to claim 4, wherein said compound is selected from the group consisting of:
- (R)-4-(3-Amino-pyrrolidin-1-yl)-6-isopropyl-pyrimidin-2-ylamine; and
- (S)-4-(3-Amino-pyrrolidin-1-yl)-6-isopropyl-pyrimidin-2-ylamine;

and a pharmaceutically acceptable salt thereof.

* * * * *